(12) United States Patent
Tani et al.

(10) Patent No.: US 6,576,785 B1
(45) Date of Patent: Jun. 10, 2003

(54) ω-CYCLOALKYL-PROSTAGLANDIN $E_2$ DERIVATIVES

(75) Inventors: Kousuke Tani, Mishima-gun (JP); Shuichi Ohuchida, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/570,728

(22) Filed: May 12, 2000

Related U.S. Application Data

(62) Division of application No. 09/018,565, filed on Feb. 4, 1998, now Pat. No. 6,110,969.

(30) Foreign Application Priority Data

Feb. 4, 1997 (JP) .............................. 9-035499
Nov. 6, 1997 (JP) .............................. 9-319169

(51) Int. Cl.[7] ........................................... C07C 405/00
(52) U.S. Cl. ...................................... 560/118; 560/231
(58) Field of Search .............................. 560/118, 231; 562/500

(56) References Cited

U.S. PATENT DOCUMENTS 4,061,670 A * 12/1977 Floyd ......................... 260/514
5,698,598 A * 12/1997 Woodward .................. 514/530

\* cited by examiner

Primary Examiner—Robert Gerstl

(74) Attorney, Agent, or Firm—Stevens, Davis, Miller & Mosher, L.L.P.

(57) ABSTRACT

A ω-cycloalkyl-prostaglandin $E_2$ derivatives of the formula (I)

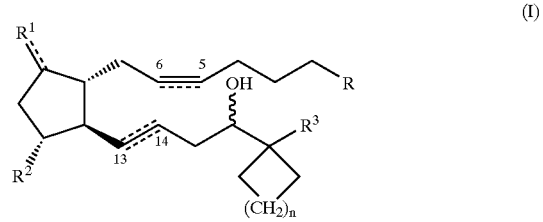

wherein R is carboxy or hydroxymethyl; $R^1$ is oxo, methylene or halogen atom; $R^2$ is H, OH or C1–4 alkoxy; $R^3$ is H, C1–8 alkyl, C2–8 alkenyl, C2–8 alkynyl, C1–8 alkyl, C2–8 alkenyl or C2–8 alkynyl substituted by 1–3 of substituent selected from halogen atom, C1–4 alkoxy, C3–7 cycloalkyl, phenyl, or phenyl substituted by 1–3 of substituent selected from halogen atom, C1–4 alkyl, C1–4 alkoxy, nitro, trifluoromethyl; n is 0–4;

and non-toxic salt thereof, prodrug thereof and cyclodextrin clathrate thereof can strongly bind on $EP_2$ subtype receptor. Therefore, they are useful for prevention and/or treatment of immune disease (autoimmune disease, organ transplantation, etc.), asthma, abnormal bone formation, neuron cell death, liver damage, abortion, premature birth or retina neuropathy of glaucoma etc.

2 Claims, No Drawings

ω-CYCLOALKYL-PROSTAGLANDIN E₂ DERIVATIVES

CROSS-REFERENCE TO RELATED APPLICATIONS this application is a divisional application Ser. No. 09/018,565, filed Feb. 4, 1998 now U.S. Pat. No. 6,110,969.

FIELD OF INVENTION

This invention is related to ω-cycloalkyl-prostaglandin E₂ derivatives. More particularly, this invention is related to:

(1) ω-cycloalkyl-prostaglandin E₂ derivatives of the formula (I)

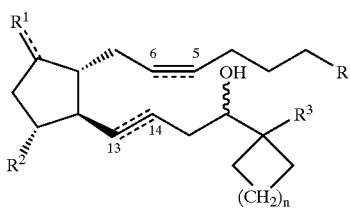

(I)

wherein all the symbols are the same meaning as hereafter defined, non-toxic salt thereof, prodrug thereof and cyclodextrin clathrate thereof.

BACKGROUND

Prostaglandin E₂ (abbreviated as PGE₂ hereafter) has been known as metabolite in the arachidonate cascade. It has been known that PGE₂ has cyto-protective activity, uterine contractile activity, a pain-inducing effect, a promoting effect of digestive peristalsis, an awakening effect, a suppressive effect of gastric acid secretion, hypotensive activity and diuretic activity etc.

In a recent study, it was found that PGE₂ receptor was divided into some subtype which possess different physiological roles from each other. At present four receptor subtypes are known and they are called as $EP_1$, $EP_2$, $EP_3$ and $EP_4$ (Negishi M. et al, J. Lipid Mediators Cell Signaling, 12, 379–391 (1995)).

The present inventors investigated to find new compounds which bind on each receptor specifically, we found that the compounds of the present invention could bind strongly on $EP_2$ subtype receptor and achieved the present invention.

The compounds of the formula (I) of the present invention possess a binding activity for $EP_2$ subtype receptor strongly. Therefore, they are useful for prevention and/or treatment of immunologic diseases (autoimmune diseases, organ transplantation, etc.), asthma, abnormal bone formation, neuronal cell death, liver damage, abortion, premature birth or retina neuropathy of glaucoma etc.

Among the compounds of the present invention of the formula (I), compounds which bind weakly on receptor subtypes except for $EP_2$ and another arachidonic acid metabolism receptor (thromboxane receptor, $PGI_2$ receptor, etc.) do not exhibit other effects and therefore, it is thought that such compounds will be useful as medical agents which have less side-effects.

On the other hand, many patent applications of PG derivatives are known. The following application is mentioned for example.

In the specification of U.S. Pat. No. 4,132,738, a compound of the formula (A)

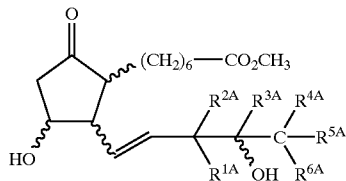

(A)

wherein $R^{1A}$ and $R^{2A}$ is hydrogen atom;

$R^{3A}$ is hydrogen atom, or together with $R^{4A}$ is a methylene chain of 4 carbon atoms such that a cycloalkyl of 6 carbon atoms inclusive is formed, or together with $R^{4A}$ is a bicycloalkenyl or bicycloalkyl moiety having the formula

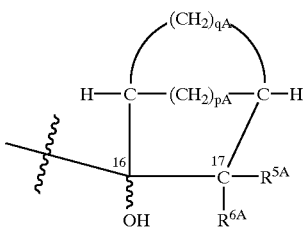

(in which pA is an integer having a value of from 0 to 1 and qA is an integer having a value of from 2 to 3 and wherein the double bond of such bicycloalkenyl is in the qA bridge);

$R^{4A}$ together with $R^{3A}$ forms a cycloalkyl or bicycloalkyl or bicycloalkenyl as defined above, or together with $R^{5A}$ is a methylene chain of 3 carbon atoms such that a cycloalkyl of 4 carbon atoms inclusive is formed;

$R^{5A}$ is hydrogen atom, or together with $R^{4A}$ forms a cycloalkyl as defined above; and $R^{6A}$ is hydrogen atom or straight-chain alkyl having from 1 to 8 carbon atoms; are disclosed as having an inhibitory activity on prostaglandin like.

DISCLOSURE OF THE INVENTION

The present invention is related to (1) ω-cycloalkyl-prostaglandin E₂ derivatives of the formula (I)

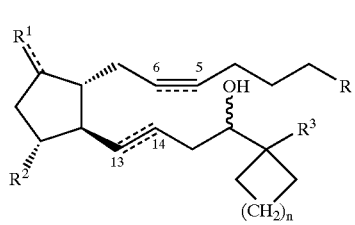

(I)

wherein

R is carboxy or hydroxymethyl;

$R^1$ is oxo, methylene or halogen atom;

$R^2$ is hydrogen atom, hydroxy or C1–4 alkoxy;

$R^3$ is (i) hydrogen atom, (ii) C1–8 alkyl, (iii) C2–8 alkenyl, (iv) C2–8 alkynyl or (v) C1–8 alkyl, C2–8 alkenyl or C2–8 alkynyl, each substituted by 1–3 substituents, being same or different, selected from (1)–(5);

(1) halogen atom,
(2) C1–4 alkoxy,
(3) C3–7 cycloalkyl,
(4) phenyl, or
(5) phenyl substituted by 1–3 substituents selected from halogen atom, C1–4 alkyl, C1–4 alkoxy, nitro or trifluoromethyl;

n is 0–4;

⸺ is single bond or double bond;

⸺ is double bond or triple bond;

⸺ is single bond, double bond or triple bond;
with the proviso that,
1) when 5–6 position is triple bond, 13–14 position is not triple bond,
2) when 13–14 position is double bond represent E or Z form; non-toxic salt thereof, prodrug thereof and cyclodextrin clathrate thereof,
(2) processes for the preparation thereof, and
(3) pharmaceutical agents containing such a derivative as an active ingredient.

In the present invention, prodrug means
1) for compounds of formula (I) of the present invention, those in which R represent $COOR^{10}$ (in which $R^{10}$ is C1–6 alkyl), i.e., the compounds of formula (IA)

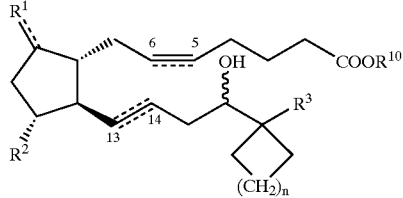

(IA)

wherein all symbols are the same meaning as hereinbefore defined 2) for compounds of formula (I) of the present invention, those in which R represent $CONR^2R^{13}$ (in which $R^{12}$ and $R^{13}$ each, independently, is hydrogen atom or C1–6 alkyl), i.e., the compounds of formula (IB)

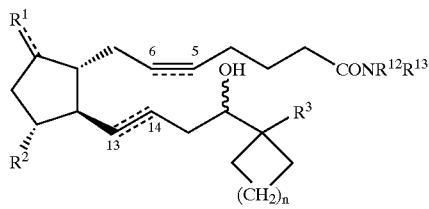

(IB)

wherein all symbols are the same meaning as hereinbefore defined, or 3) for compounds of formula (I) of the present invention, those in which R represent $COOR^{10}$ (in which $R^{10}$ is the same meaning as hereinbefore defined), $R^1$ represent $R^{11}$—COO (in which $R^{11}$ is C1–4 alkyl, C1–4 alkoxy, phenyl, phenyl-C1–4 alkyl, $R^{14}$—OOC—C1–4 alkyl or $R^{14}$—OOC—C2–4 alkenyl (in which $R^{14}$ is hydrogen atom or C1–4 alkyl) 8–9 position is double bond), i.e., the compounds of formula (IC)

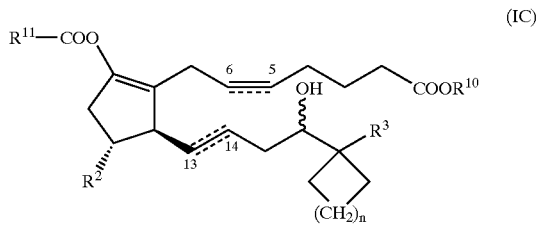

(IC)

wherein all symbols are the same meaning as hereinbefore defined.

In formula (I) or (IC), C1–4 alkyl represented by $R^3$, $R^{11}$, and $R^{14}$ means methyl, ethyl, propyl, butyl and isomers thereof.

In formula (I), (IA) or (IB), C1–6 alkyl represented by $R^{10}$, $R^{12}$ and $R^{13}$ means methyl, ethyl, propyl, butyl, pentyl, hexyl and isomers thereof.

In formula (I), C1–8 alkyl represented by $R^3$ means methyl, ethyl, propyl, butyl, pentyl, hexyl, heptyl, octyl and isomers thereof.

In formula (I), C2–4 alkenyl represented by $R^{11}$ means vinyl, propenyl, butenyl and isomers thereof.

In formula (I), C2–8 alkenyl represented by $R^3$ means vinyl, propenyl, butenyl, pentenyl, hexenyl, heptenyl, octenyl and isomers thereof.

In formula (I), C2–8 alknyl represented by $R^3$ means ethynyl, propynyl, butynyl, pentynyl, hexynyl, heptynyl, octynyl and isomers thereof.

In formula (I), or (IC), C1–4 alkoxy represented by $R^2$, $R^{11}$ and $R^3$ means methoxy, ethoxy, propoxy, butoxy and isomers thereof.

In formula (I), C3–7 cycloalkyl represented by $R^3$ means cyclopropyl, cyclobutyl, cyclopentyl, cyclohexyl, and cycloheptyl.

In formula (I), a halogen atom represented by $R^1$ and $R^3$ means fluorine, chlorine, bromine and iodine.

In the present invention, it may be easily understood by those skilled in the art, unless otherwise specified, the symbol:

indicates that the substituent attached thereto is in front of the sheet, unless otherwise specified, the symbol:

indicates that the substituent attached thereto is behind the sheet, unless otherwise specified, the symbol:

 or 

indicates that the substituent attached thereto is a mixture of in front of and behind the sheet or may be in front of or behind the sheet.

Unless otherwise specified, all isomers are included in the present invention. For example, the alkyl, alkenyl and alkynyl groups include straight-chain and also branched-chain ones. The double bond in alkenyl group include E, Z and EZ mixture ones. Isomers generated by the existence of asymmetric carbon atom(s) e.g. in are included in branched-chain alkyl are included in the present invention.

Preferred compounds of the present invention of the formula (I) are listed in examples, Table 1–14 or prodrug thereof.

TABLE 1

(Ia)
| No. | n | R³ |
|---|---|---|
| 1 | 0 | 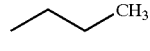 |
| 2 | 0 | 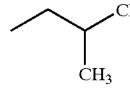 |
| 3 | 0 | 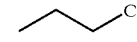 |
| 4 | 0 | 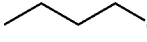 |
| 5 | 0 | 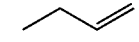 |
| 6 | 0 | 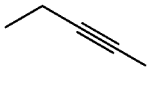 |
| 7 | 0 | 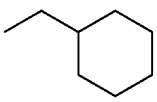 |
| 8 | 0 | 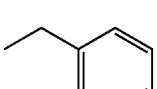 |
| 9 | 0 | 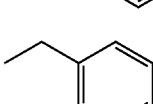 |
| 10 | 0 | 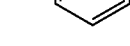 |
| 11 | 1 | 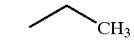 |
| 12 | 1 | 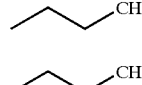 |
| 13 | 1 |  |
| 14 | 1 | 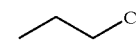 |
| 15 | 1 | 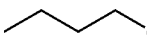 |
| 16 | 1 | 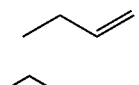 |
| 17 | 1 | 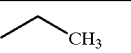 |
| 18 | 1 | 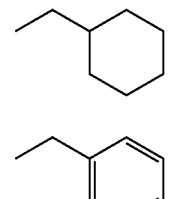 |
| 19 | 1 | 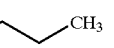 |
| 20 | 1 | 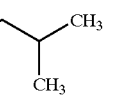 |
TABLE 2
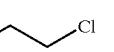
(Ib)
| No. | n | R³ |
|---|---|---|
| 1 | 0 | 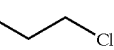 |
| 2 | 0 | 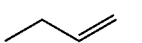 |
| 3 | 0 | 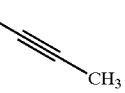 |
| 4 | 0 | 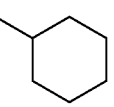 |
| 5 | 0 | 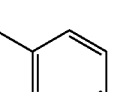 |
| 6 | 0 | 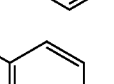 |
| 7 | 0 | 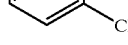 |
| 8 | 0 |  |
| 9 | 0 | 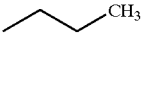 |
| 10 | 0 |  |
| 11 | 1 |  |
| 12 | 1 | |

TABLE 2-continued
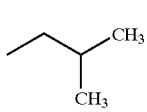
(Ib)
| No. | n | R³ |
|---|---|---|
| 13 | 1 |  |
| 14 | 1 |  |
| 15 | 1 |  |
| 16 | 1 | 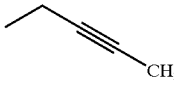 |
| 17 | 1 | 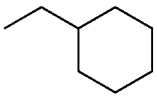 |
| 18 | 1 | 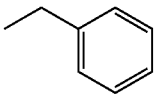 |
| 19 | 1 | 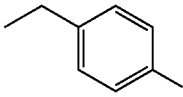 |
| 20 | 1 | 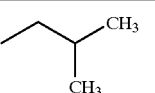 |
TABLE 3
(Ic)
| No. | n | R³ |
|---|---|---|
| 1 | 0 |  |
| 2 | 0 | 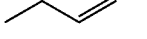 |
TABLE 3-continued
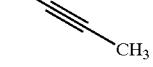
(Ic)
| No. | n | R³ |
|---|---|---|
| 3 | 0 | 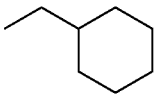 |
| 4 | 0 | 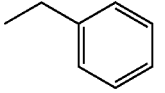 |
| 5 | 0 | 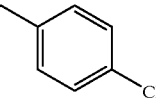 |
| 6 | 0 | 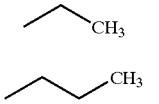 |
| 7 | 0 |  |
| 8 | 0 | 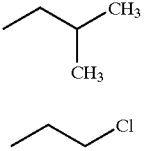 |
| 9 | 0 |  |
| 10 | 0 | 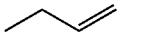 |
| 11 | 1 |  |
| 12 | 1 |  |
| 13 | 1 | 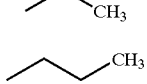 |
| 14 | 1 |  |
| 15 | 1 | |
| 16 | 1 | |
| 17 | 1 | |

TABLE 3-continued
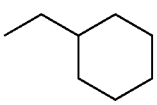
(Ic)
| No. | n | R³ |
|---|---|---|
| 18 | 1 | 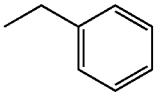 |
| 19 | 1 | 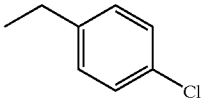 |
| 20 | 1 | 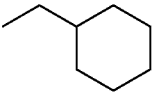 |
TABLE 4
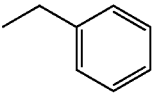
(Id)
| No. | n | R³ |
|---|---|---|
| 1 | 0 | 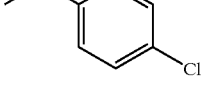 |
| 2 | 0 | 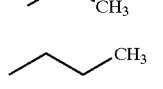 |
| 3 | 0 | 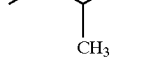 |
| 4 | 0 | 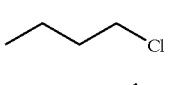 |
| 5 | 0 | 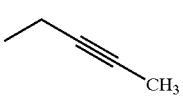 |
| 6 | 0 | 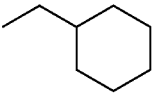 |
| 7 | 0 | 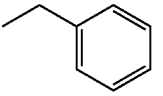 |
TABLE 4-continued
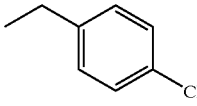
(Id)
| No. | n | R³ |
|---|---|---|
| 8 | 0 | 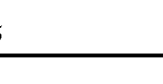 |
| 9 | 0 |  |
| 10 | 0 |  |
| 11 | 1 |  |
| 12 | 1 | 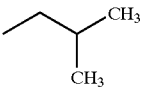 |
| 13 | 1 |  |
| 14 | 1 |  |
| 15 | 1 | 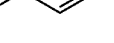 |
| 16 | 1 | 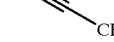 |
| 17 | 1 | 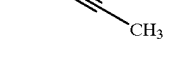 |
| 18 | 1 | 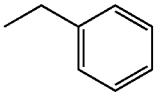 |
| 19 | 1 | 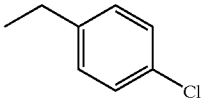 |
| 20 | 1 | 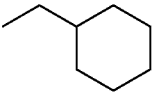 |
TABLE 5
(Ie)

11
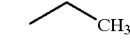
| No. | n | R³ |
|---|---|---|
| 1 | 0 | 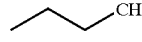 |
| 2 | 0 | 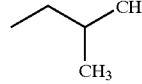 |
| 3 | 0 | 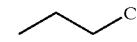 |
| 4 | 0 | 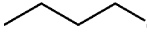 |
| 5 | 0 | 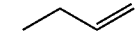 |
| 6 | 0 | 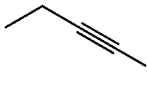 |
| 7 | 0 | 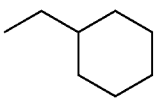 |
| 8 | 0 | 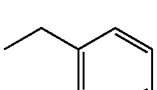 |
| 9 | 0 | 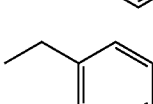 |
| 10 | 0 | 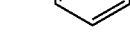 |
| 11 | 1 | 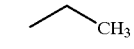 |
| 12 | 1 | 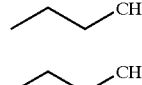 |
| 13 | 1 |  |
| 14 | 1 | 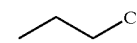 |
| 15 | 1 | 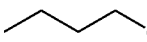 |
| 16 | 1 | 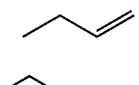 |
| 17 | 1 | 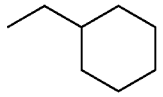 |
12
| No. | n | R³ |
|---|---|---|
| 18 | 1 | 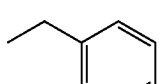 |
| 19 | 1 | 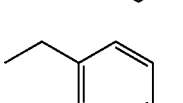 |
| 20 | 1 |  |
TABLE 6
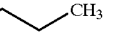 (If)
| No. | n | R³ |
|---|---|---|
| 1 | 0 | 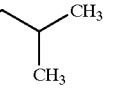 |
| 2 | 0 | 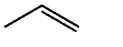 |
| 3 | 0 | 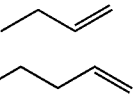 |
| 4 | 0 | 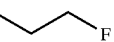 |
| 5 | 0 | 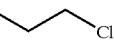 |
| 6 | 0 | 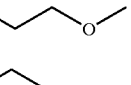 |
| 7 | 0 |  |
| 8 | 0 | 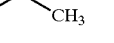 |
| 9 | 0 | 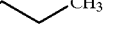 |
| 10 | 0 | 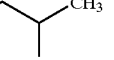 |
| 11 | 1 | 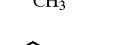 |
| 12 | 1 |  |
| 13 | 1 |  |
| 14 | 1 |  |

TABLE 6-continued (If)

| No. | n | R³ |
|-----|---|-----|
| 15 | 1 | CH₂=CHCH₂CH₂- (allyl-type chain) |
| 16 | 1 | CH₂=CH(CH₂)₃- |
| 17 | 1 | F(CH₂)₄- |
| 18 | 1 | Cl(CH₂)₄- |
| 19 | 1 | MeO(CH₂)₄- |
| 20 | 1 | cyclopropyl-CH₂CH₂- |

TABLE 7

(Ig)

| No. | n | R³ |
|-----|---|-----|
| 1 | 0 | -CH₂CH₂CH₃ |
| 2 | 0 | -(CH₂)₃CH₃ |
| 3 | 0 | -CH₂CH(CH₃)CH₃ (isobutyl) |
| 4 | 0 | -CH₂CH=CH₂ |
| 5 | 0 | -CH₂CH₂CH=CH₂ |
| 6 | 0 | -(CH₂)₃CH=CH₂ |
| 7 | 0 | -(CH₂)₄F |
| 8 | 0 | -(CH₂)₄Cl |
| 9 | 0 | -(CH₂)₄OMe |

TABLE 7-continued (Ig)

| No. | n | R³ |
|-----|---|-----|
| 10 | 0 | cyclopropyl-CH₂- |
| 11 | 1 | -CH₂CH₂CH₃ |
| 12 | 1 | -(CH₂)₃CH₃ |
| 13 | 1 | -CH₂CH(CH₃)CH₃ |
| 14 | 1 | -CH₂CH=CH₂ |
| 15 | 1 | -CH₂CH₂CH=CH₂ |
| 16 | 1 | -(CH₂)₃CH=CH₂ |
| 17 | 1 | -(CH₂)₄F |
| 18 | 1 | -(CH₂)₄Cl |
| 19 | 1 | -(CH₂)₄OMe |
| 20 | 1 | cyclopropyl-CH₂CH₂- |

TABLE 8

(Ih)

| No. | n | R³ |
|-----|---|-----|
| 1 | 0 | -CH₂CH₂CH₃ |
| 2 | 0 | -(CH₂)₃CH₃ |
| 3 | 0 | -CH₂CH(CH₃)CH₃ |

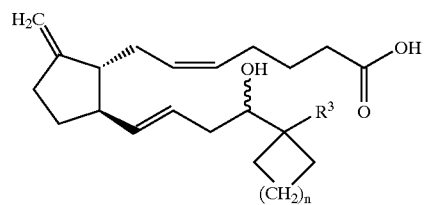

TABLE 8-continued (Ih)

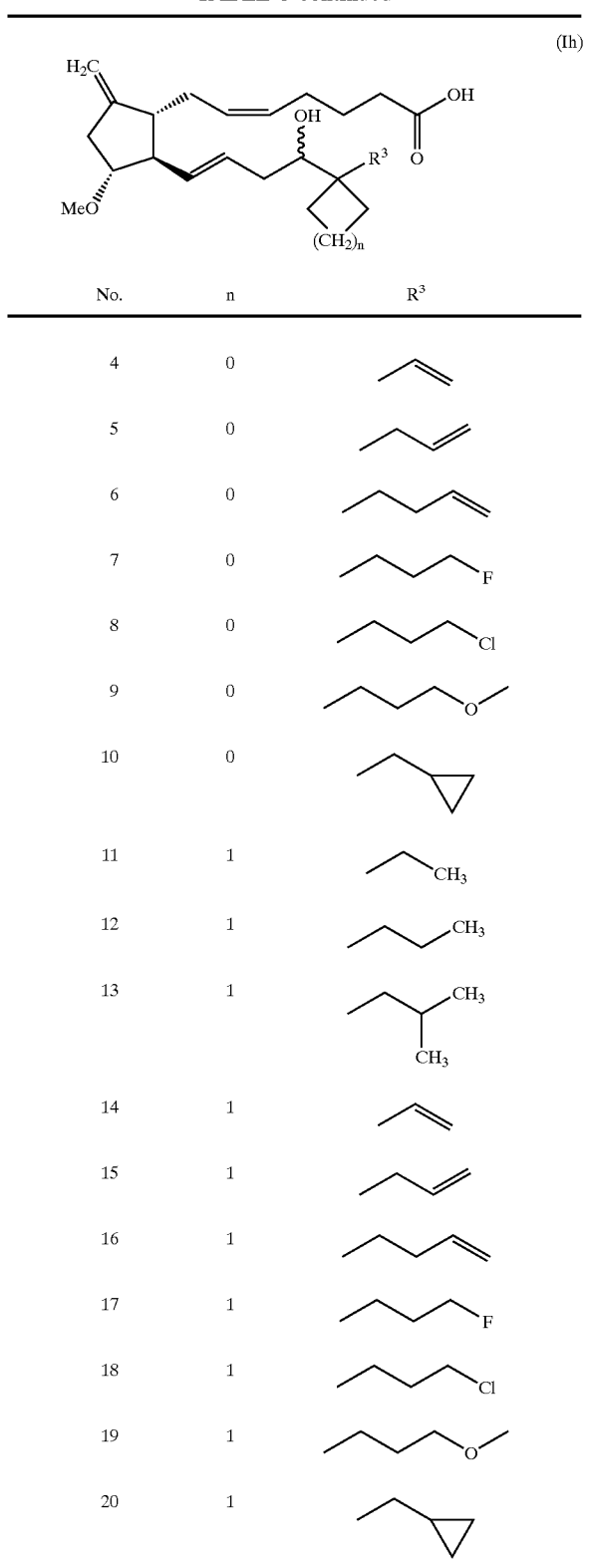

| No. | n | R³ |
|---|---|---|
| 4 | 0 | CH₂=CH-CH₂- |
| 5 | 0 | CH₂=CH-CH₂-CH₂- |
| 6 | 0 | CH₂=CH-CH₂-CH₂-CH₂- |
| 7 | 0 | F-(CH₂)₄- |
| 8 | 0 | Cl-(CH₂)₄- |
| 9 | 0 | MeO-(CH₂)₄- |
| 10 | 0 | cyclopropyl-CH₂- |
| 11 | 1 | CH₃-CH₂-CH₂- |
| 12 | 1 | CH₃-(CH₂)₃- |
| 13 | 1 | (CH₃)₂CH-CH₂- |
| 14 | 1 | CH₂=CH-CH₂- |
| 15 | 1 | CH₂=CH-CH₂-CH₂- |
| 16 | 1 | CH₂=CH-(CH₂)₃- |
| 17 | 1 | F-(CH₂)₄- |
| 18 | 1 | Cl-(CH₂)₄- |
| 19 | 1 | MeO-(CH₂)₄- |
| 20 | 1 | cyclopropyl-CH₂- |

TABLE 9

(Ii)

| No. | n | R³ |
|---|---|---|
| 1 | 0 | CH₃-CH₂-CH₂- |
| 2 | 0 | CH₃-(CH₂)₃- |
| 3 | 0 | (CH₃)₂CH-CH₂- |
| 4 | 0 | CH₂=CH-CH₂- |
| 5 | 0 | CH₂=CH-CH₂-CH₂- |
| 6 | 0 | CH₂=CH-(CH₂)₃- |
| 7 | 0 | F-(CH₂)₄- |
| 8 | 0 | Cl-(CH₂)₄- |
| 9 | 0 | MeO-(CH₂)₄- |
| 10 | 0 | cyclopropyl-CH₂- |
| 11 | 1 | CH₃-CH₂-CH₂- |
| 12 | 1 | CH₃-(CH₂)₃- |
| 13 | 1 | (CH₃)₂CH-CH₂- |
| 14 | 1 | CH₂=CH-CH₂- |
| 15 | 1 | CH₂=CH-CH₂-CH₂- |
| 16 | 1 | CH₂=CH-(CH₂)₃- |
| 17 | 1 | F-(CH₂)₄- |
| 18 | 1 | Cl-(CH₂)₄- |
| 19 | 1 | MeO-(CH₂)₄- |
| 20 | 1 | cyclopropyl-CH₂- |

TABLE 10

| | | 17 | | | | 18 | |
|---|---|---|---|---|---|---|---|
| | | | (Ij) | | | | (Ik) |
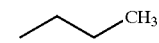
| No. | n | R³ | | No. | n | R³ |
|---|---|---|---|---|---|---|
| 1 | 0 | ⁓CH₃ | | 1 | 0 | ⁓CH₃ |
| 2 | 0 | ⁓CH₃ | | 2 | 0 | ⁓CH₃ |
| 3 | 0 | ⁓CH(CH₃)₂ | | 3 | 0 | ⁓CH(CH₃)₂ |
| 4 | 0 | ⁓= | | 4 | 0 | ⁓= |
| 5 | 0 | ⁓⁓= | | 5 | 0 | ⁓⁓= |
| 6 | 0 | ⁓⁓⁓= | | 6 | 0 | ⁓⁓⁓= |
| 7 | 0 | ⁓⁓F | | 7 | 0 | ⁓⁓F |
| 8 | 0 | ⁓⁓Cl | | 8 | 0 | ⁓⁓Cl |
| 9 | 0 | ⁓⁓O⁓ | | 9 | 0 | ⁓⁓O⁓ |
| 10 | 0 | ⁓▷ | | 10 | 0 | ⁓▷ |
| 11 | 1 | ⁓CH₃ | | 11 | 1 | ⁓CH₃ |
| 12 | 1 | ⁓CH₃ | | 12 | 1 | ⁓CH₃ |
| 13 | 1 | ⁓CH(CH₃)₂ | | 13 | 1 | ⁓CH(CH₃)₂ |
| 14 | 1 | ⁓= | | 14 | 1 | ⁓= |
| 15 | 1 | ⁓⁓= | | 15 | 1 | ⁓⁓= |
| 16 | 1 | ⁓⁓⁓= | | 16 | 1 | ⁓⁓⁓= |
| 17 | 1 | ⁓⁓F | | 17 | 1 | ⁓⁓F |
| 18 | 1 | ⁓⁓Cl | | 18 | 1 | ⁓⁓Cl |
| 19 | 1 | ⁓⁓O⁓ | | 19 | 1 | ⁓⁓O⁓ |
| 20 | 1 | ⁓▷ | | 20 | 1 | ⁓▷ |
TABLE 11

TABLE 12
(II)
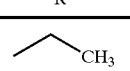
| No. | n | R³ |
|---|---|---|
| 1 | 0 |  |
| 2 | 0 | 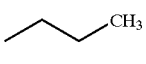 |
| 3 | 0 |  |
| 4 | 0 | 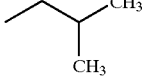 |
| 5 | 0 |  |
| 6 | 0 | 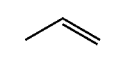 |
| 7 | 0 |  |
| 8 | 0 | 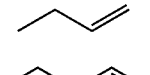 |
| 9 | 0 |  |
| 10 | 0 | 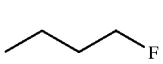 |
| 11 | 1 |  |
| 12 | 1 | 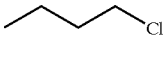 |
| 13 | 1 |  |
| 14 | 1 | 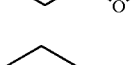 |
| 15 | 1 |  |
| 16 | 1 | 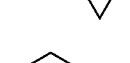 |
| 17 | 1 |  |
| 18 | 1 | 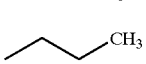 |
| 19 | 1 |  |
| 20 | 1 | 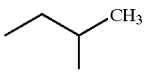 |
TABLE 13
(Im)
| No. | n | R³ |
|---|---|---|
| 1 | 0 | 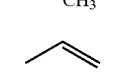 |
| 2 | 0 |  |
| 3 | 0 | 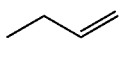 |
| 4 | 0 |  |
| 5 | 0 | 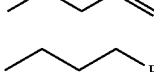 |
| 6 | 0 |  |
| 7 | 0 | 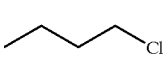 |
| 8 | 0 |  |
| 9 | 0 | 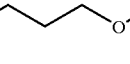 |
| 10 | 0 |  |
| 11 | 1 |  |
| 12 | 1 |  |
| 13 | 1 |  |
| 14 | 1 |  |
| 15 | 1 |  |
| 16 | 1 |  |
| 17 | 1 | |
| 18 | 1 | |
| 19 | 1 | |
| 20 | 1 | |

TABLE 14

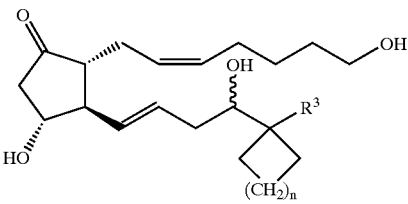

(In)

| No. | n | R³ |
|---|---|---|
| 1 | 0 | ~~CH₃ |
| 2 | 0 | ~~CH₃ |
| 3 | 0 | ~~CH(CH₃)₂ |
| 4 | 0 | CH₂=CH– |
| 5 | 0 | allyl |
| 6 | 0 | butenyl |
| 7 | 0 | ~~F |
| 8 | 0 | ~~Cl |
| 9 | 0 | ~~O–CH₃ |
| 10 | 0 | cyclopropylmethyl |
| 11 | 1 | ~~CH₃ |
| 12 | 1 | ~~CH₃ |
| 13 | 1 | ~~CH(CH₃)₂ |
| 14 | 1 | CH₂=CH– |
| 15 | 1 | allyl |
| 16 | 1 | butenyl |
| 17 | 1 | ~~F |
| 18 | 1 | ~~Cl |
| 19 | 1 | ~~O–CH₃ |
| 20 | 1 | cyclopropylmethyl |

Salts

The compounds of formula(I) of the present invention may be converted into a corrresponding non-toxic salt by methods known per se. Non toxic and water-soluble salts are preferable. Suitable salts, for example, are salts of an alkaline metal (potassium, sodium, etc.), salts of an alkaline earth metal (calcium, magnesium, etc.), ammonium salts and salts of pharmaceutically-acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.).

Cyclodextrin Clathrates

Cyclodextrin clathrates of ω-cycloalkyl-prostaglandin $E_2$ derivatives of the formula (I) may be prepared by the method described in the specification of GB 1351238, which is herein incorporated by reference, using α-, β- or γ-cyclodextrins or a mixture thereof. Converting into their cyclodextrin clathrates serves to increase the stability and solubility in water of the compounds, and is therefore, useful in the use of pharmaceuticals.

Process for the Preparation

1) For compounds of formula (I) of the present invention, those in which R is carboxy, i.e., the compounds of formula (I-1)

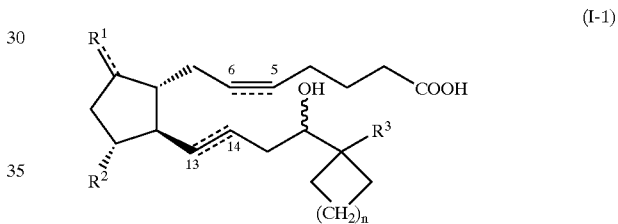

(I-1)

wherein all the symbols are the same meaning hereinbefore defined may be prepared by hydrolysis using enzyme or hydrolysis in an alkaline condition of a compound of formula (IA)

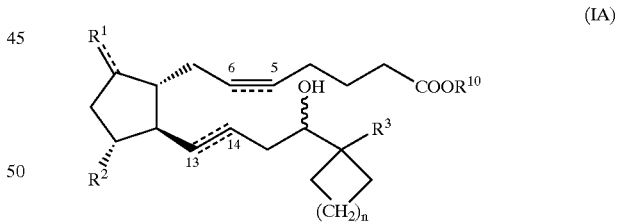

(IA)

wherein all the symbols are the same meaning hereinbefore defined.

The hydrolysis using enzyme is known. For example, hydrolysis may be carried out in the mixture of a water-miscible organic solvent (ethanol, dimethylsulfoxide etc.) and water, in the presence or absence of buffer, using an ester cleaving enzyme (esterase, lipase etc.), at a temperature of from 0° C. to 50° C.

The hydrolysis in an alkaline condition is known. For example, hydrolysis may be carried out in a water-miscible organic solvent (ethanol, tetrahydrofuran, dioxan etc.), using aqueous solution of an alkali (sodium hydroxide, potassium hydroxide, potassium carbonate etc.), at a temperature of from −10 to 90° C.

2) For compounds of formula (I) of the present invention, those in which R is hydroxymethyl, i.e., in the compounds of formula (I-2),

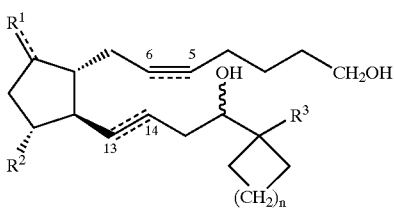
(I-2)

wherein all the symbols are the same meaning as hereinbefore defined;
those in which $R^1$ is oxo, i.e., the compounds of formula (I-2A)

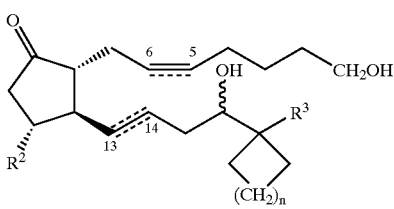
(I-2A)

wherein all the symbols are the same meaning as hereinbefore defined;
may be prepared by subjecting to elimination of the protecting group in an acidic condition of a compound of formula (IIA)

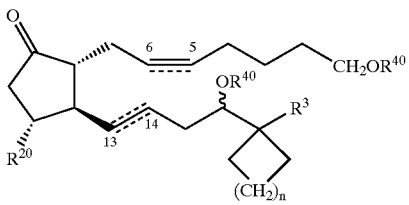
(IIA)

wherein $R^{20}$ is hydrogen atom, hydroxy protecting group to elimination in an acidic condition or C1–4 alkoxy, $R^{40}$ is hydroxy protecting group to remove in an acid condition, the other symbols are the same meaning as herein before defined.

The hydroxy protecting group to elimination in an acidic condition include, for example, t-butyldimethylsiliyl, triphenylmethyl, tetrahydropyran-2-yl etc.

The hydrolysis in an acidic condition is known. For example, hydrolysis may be carried out in a water-miscible organic solvent (tetrahydrofuran, methanol, ethanol, dimethoxyethane, acetonitrile or mixture thereof etc.), using an inorganic acid (hydrochloric acid, phosphoric acid, hydrofluoric acid or hydrogen fluoride-pyridine etc.), or organic acid (acetic acid, p-toluenesulfonic acid, trichloroacetc acid, etc.) at a temperature of from 0 to 50° C.

3) For compounds of formula (I) of the present invention, those in which R is hydroxymethyl, i.e., in the compounds of formula (I-2),

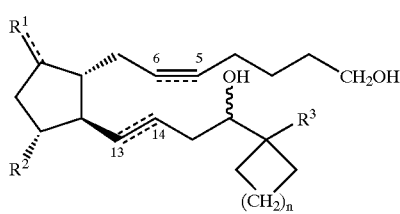
(I-2)

wherein all the symbols are the same meaning as hereinbefore defined;
those in which $R^1$ is methylene, i.e., the compounds of formula (I-2B)

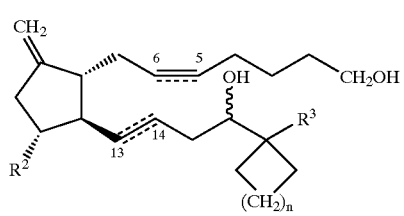
(I-2B)

wherein all the symbols are the same meaning as hereinbefore defined,
may be prepared by subjecting reduction of a compound of formula (IA-4)

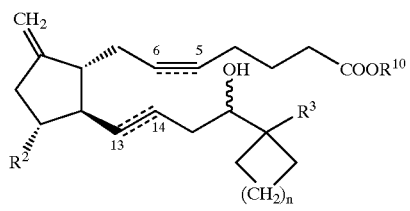
(IA-4)

wherein all the symbols are the same meaning as hereinbefore defined.

The reduction is known. For example, reduction may be carried out in an inert organic solvent (tetrahydrofuran (THF), hexane, toluene, etc.), using diisobutylaluminum hydride at a temperature of from –80 to 0° C.

4) For compounds of formula (I) of the present invention, those in which R is hydroxymethyl, i.e., in the compounds of formula (I-2),

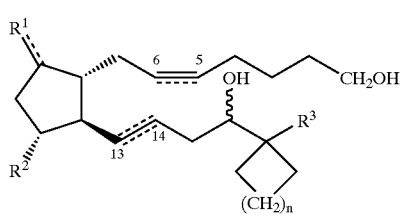
(I-2)

wherein all the symbols are the same meaning as hereinbefore defined;
those in which $R^1$ is halogen atom, i.e., the compounds of formula (I-2C)

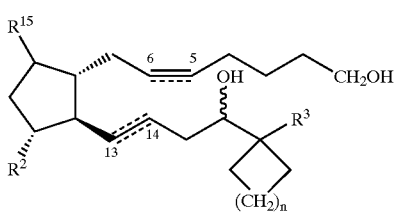

(I-2C)

wherein $R^{15}$ is halogen atom, the other symbols are the same meaning as hereinbefore defined;
may be prepared by subjecting reduction of a compound of formula (IA-5)

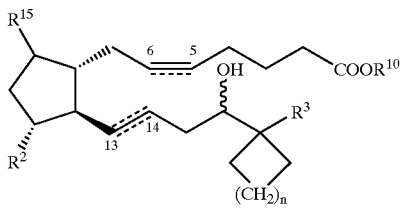

(IA-5)

wherein all the symbols are the same meaning as hereinbefore defined.

The reduction may be carried out by the same method as hereinbefore described.

5) For prodrug compounds of formula (IA) of the present invention, those in which $R^2$ is hydrogen atom or hydroxy, i.e., the compounds of formula (IA-1)

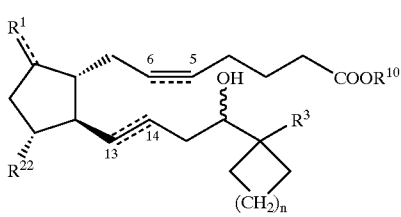

(IA-1)

wherein $R^{22}$ is hydrogen atom or hydroxy, the other symbols are the same meaning as hereinbefore defined;
may be prepared by subjecting hydrolysis in an acidic condition of a compound of formula (III)

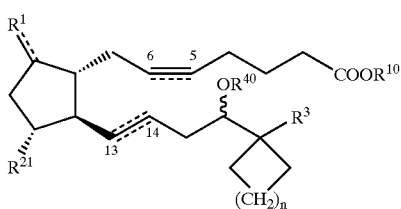

(III)

wherein $R^{21}$ is hydrogen atom or hydroxy protecting group to elimination in an acid condition, the other symbols are the same meaning as hereinbefore defined.

The hydrolysis in an acidic condition may be carried out by the same method as hereinbefore described.

6) For prodrug compounds of formula (IA) of the present invention, those in which $R^2$ is C1–4 alkoxy, i.e., the compounds of formula (IA-2)

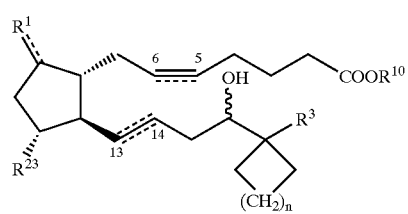

(IA-2)

wherein $R^{23}$ is C1–4 alkoxy, the other symbols are the same meaning as hereinbefore defined;
may be prepared by subjecting O-alkylation of the compounds of the formula (IA-1) those in which $R^{22}$ is hydroxy, i.e., a compound of formula (IA-3)

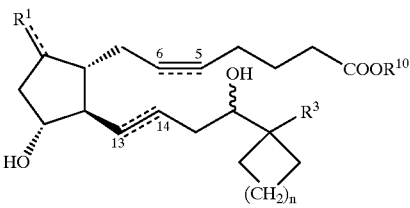

(IA-3)

wherein all the symbols are the same meaning as hereinbefore defined.

O-alkylation is known. For example, O-alkylation may be carried out in an inert organic solvent (THF, diethyl ether, etc.), using diazoalkane at a temperature of from −30 to 40° C. or in an inert organic solvent (acetonitrile, etc.), in the presence of silver oxide, using alkyl iodide at a temperature of from 0 to 40° C.

7) The prodrug compounds of formula (IB) of the present invention may be prepared by subjecting amidation of the compounds of the formula (I-1)

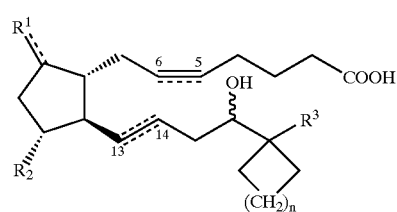

(I-1)

wherein all the symbols are the same meaning as hereinbefore defined;
with the compounds of the formula (IV)

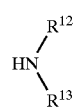

(IV)

wherein all the symbols are the same meaning as hereinbefore defined.

Amidation is known. For example, amidation may be carried out in an inert organic solvent (THF, dichloromethane, benzene, acetone, acetonitrile or mixture thereof etc.), in the presence or absence of tertiary amine (dimethylaminopyridine, pyridine, triethylamine, etc.), using condensing agent (1,3-dicyclohexylcarbodiimide (DCC), 1-ethyl-3-[3-(dimethylamino)propyl]carbodiimide (EDC), etc.) at a temperature of from 0 to 50° C.

8) The prodrug compounds of formula (IC) of the present invention may be prepared by subjecting hydrolysis in an acidic condition of the compounds of the formula (V)

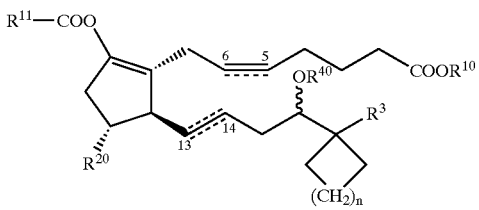

wherein all the symbols are the same meaning as hereinbefore defined.

The hydrolysis in an acidic condition may be carried out by the same method as hereinbefore described.

The compound of the formula (IIA) may be prepared by according to the reaction of the following Scheme (J).

The compound of the formula (V) may be prepared by according to the reaction of the following Scheme (K).

The compound of the formula (III) may be separated according to the type of $R^1$ and $R^{21}$ into the following six types of compounds. That is, 1) $R^1$ is oxo, $R^{21}$ is hydroxy protecting group to elimination in an acidic condition, i.e., the compound of formula (IIIA)

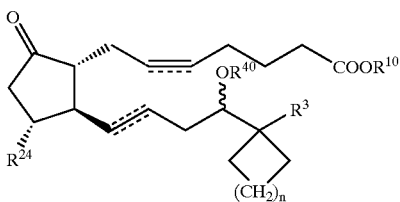

wherein $R^{24}$ is hydroxy protecting group to elimination in an acidic condition, the other symbols are the same meaning as hereinbefore defined, 2) $R^1$ is methylene, $R^{21}$ is hydroxy protecting group to elimination in an acidic condition, i.e., the compound of formula (IIIB)

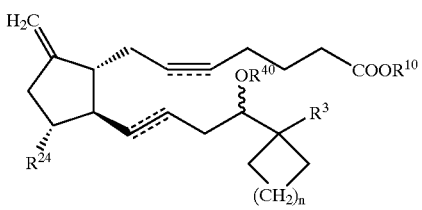

wherein all symbols are the same meaning as hereinbefore defined,

3) $R^1$ is halogen atom, $R^{24}$ is hydroxy protecting group to elimination in an acidic condition, i.e., the compound of formula (IIIC)

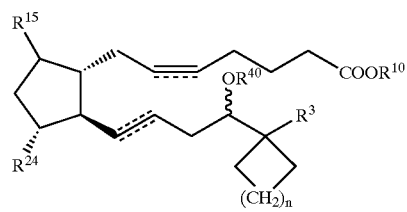

wherein $R^{15}$ is halogen atom, the other symbols are the same meaning as hereinbefore defined, 4) $R^1$ is oxo, $R^{21}$ is hydrogen atom, i.e., the compound of formula (IIID)

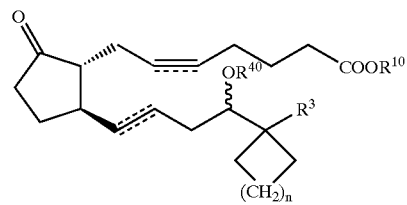

wherein all symbols are the same meaning as hereinbefore defined,

5) $R^1$ is methylene, $R^{21}$ is hydrogen atom, i.e., the compound of formula (IIIE)

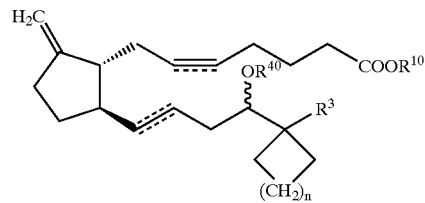

wherein all symbols are the same meaning as hereinbefore defined,

6) $R^1$ is halogen atom, $R^{21}$ is hydrogen atom, i.e., the compound of formula (IIIF)

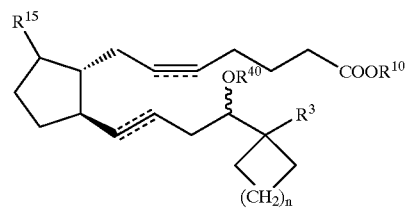

wherein all symbols are the same meaning as hereinbefore defined.

The compound of the formula (IIIB) may be prepared from the compound of the formula (IIIA) according to the reaction of the following Scheme (A).

The compound of the formula (IIIC) may be prepared from the compound of the formula (IIIA) according to the reaction of the following Scheme (B), (C) or (D).

The compound of the formula (IIID) may be prepared from the compound of the formula (IIIA) according to the reaction of the following Scheme (E).

The compound of the formula (IIIE) may be prepared from the compound of the formula (IIID) according to the same reaction of the following Scheme (A).

The compound of the formula (IIIF) may be prepared from the compound of the formula (IIID) according to the same reaction of the following Scheme (B), (C) or (D).

The compound of the formula (IIIA) may be prepared by according to the reaction of the following Scheme (F), (G) or (H).

In the Scheme, the symbols represent meanings as follow, or the same meaning as hereinbefore described.

Ts is p-toluenesulfonyl;
Ac is acetyl;
Ph is phenyl;
AIBN is 2,2'-azobisisobutylonitrile;
DIBAL is diisobutylaluminum hydride;
t-Bu is t-butyl;
n-Bu is normal butyl;
c-Hex is cyclohexyl;
Et is ethyl;
EE is ethoxyethyl;
D-(−)-DIPT is D-(−)-diisopropyl tartarate;
L-(+)-DIPT is L-(+)-diisopropyl tartarate;
Ti(OiPr)$_4$ is titanium (IV) isopropoxide;
TBHP is t-butylhydroperoxide;
Cp$_2$ZrClH is bis(cyclopentadienyl)zirconium chloride hydride.

Scheme (A)

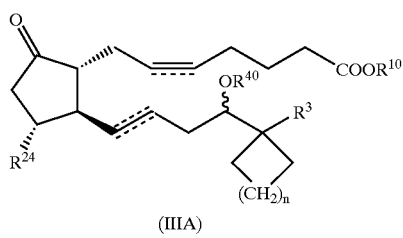

(IIIA)

| Zn, CH$_2$Br$_2$
| TiCl$_4$
↓

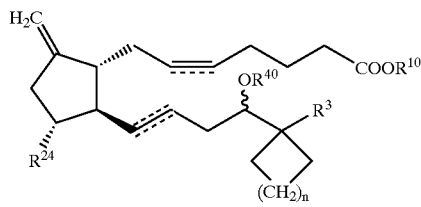

(IIIB)

Scheme (B)

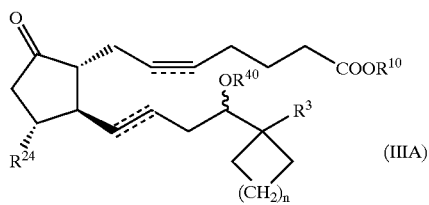

(IIIA)

| LiBH(sec-C$_4$H$_9$)$_3$
↓

-continued

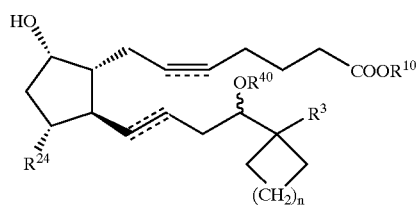

| Glacial acetic acid
↓

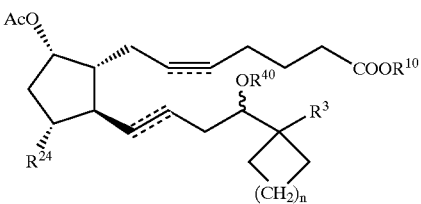

| 1) Elimination of protecting group
| 2) Separation of 16α or β
↓

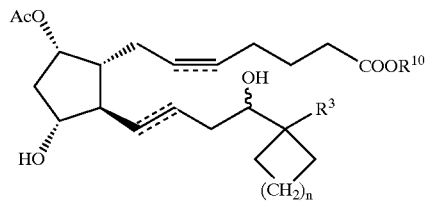

| Protection
↓

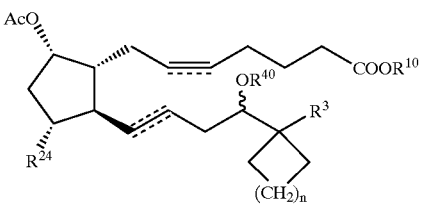

| K$_2$CO$_3$
↓

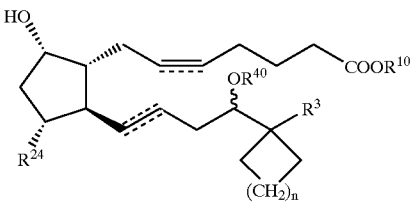

| Halogenation
↓

-continued
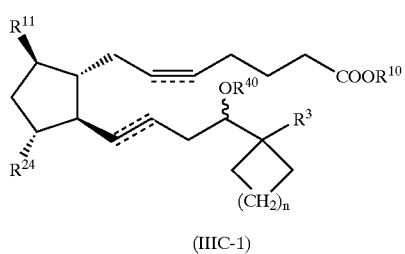
(IIIC-1)
Scheme (C)
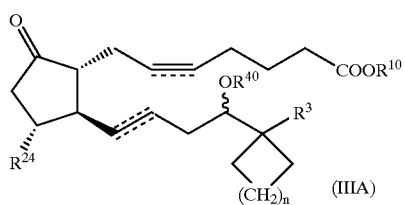
(IIIA)
↓ LiBH(sec-C₄H₉)₃
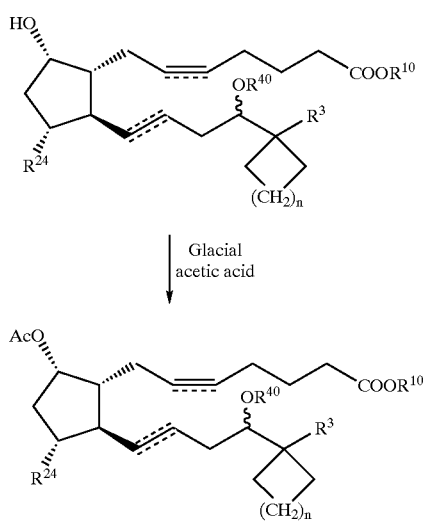
↓ Glacial acetic acid
1) Elimination of protecting group
2) Separation of 16α or β
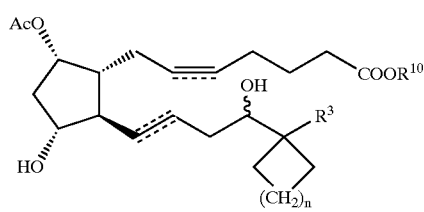
↓ Protection
-continued
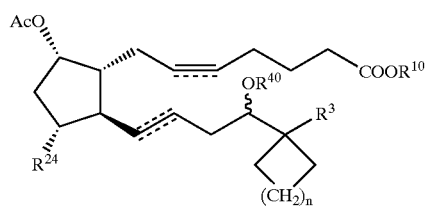
↓ $K_2CO_3$
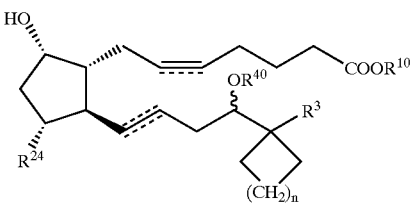
↓ TsCl
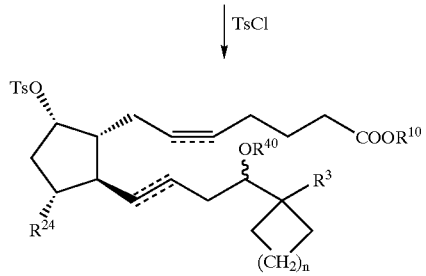
↓ Halogenation
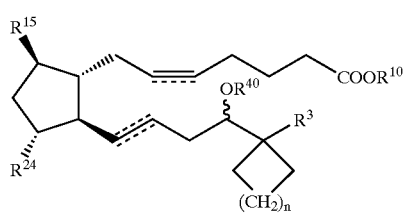
(IIIC-2)
Scheme (D)
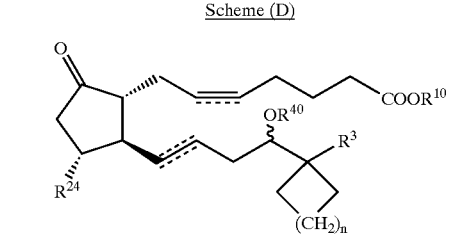
(IIIA)
↓ LiBH(sec-C₄H₉)₃

-continued
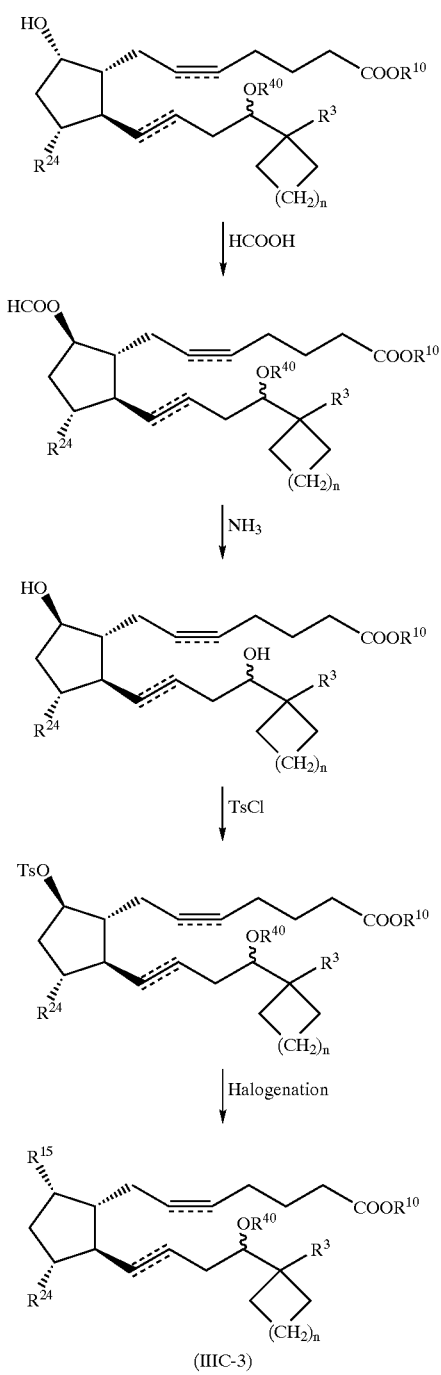
(IIIC-3)
Scheme (E)
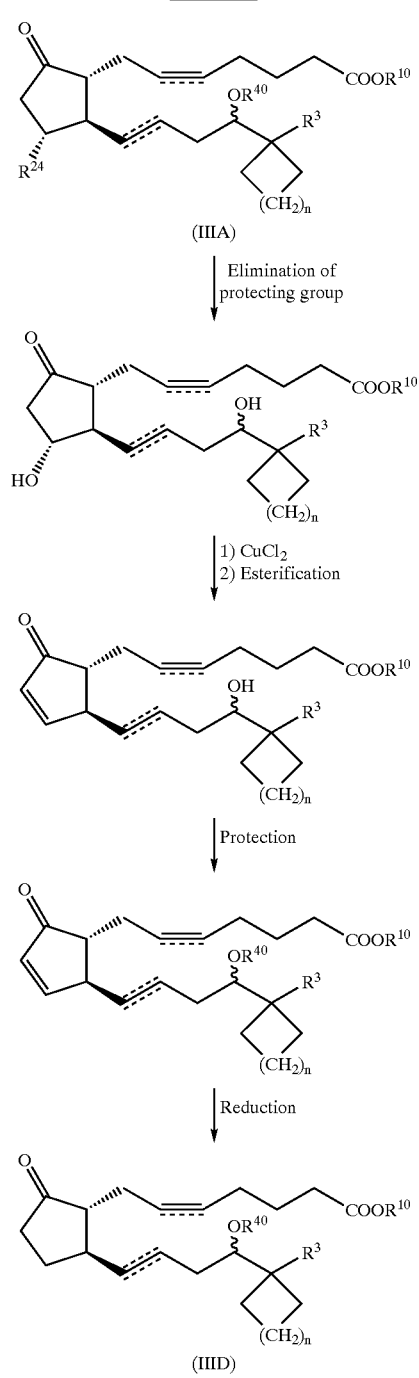
(IIID)

Scheme (F)
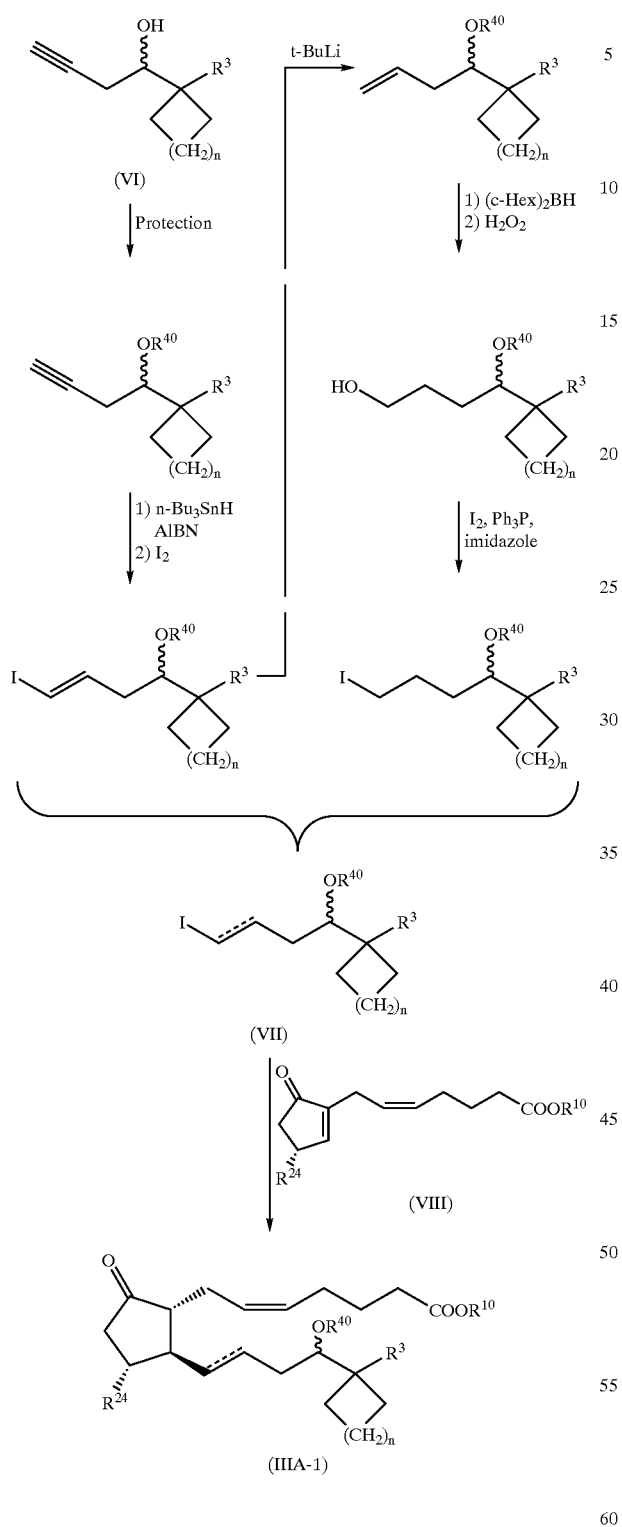
Scheme (G)
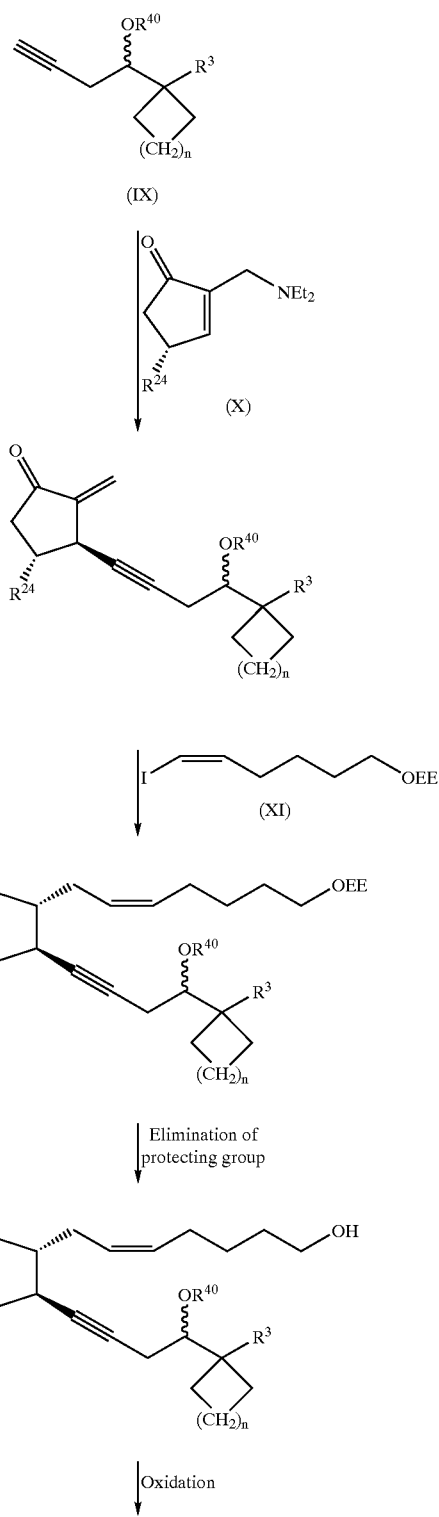

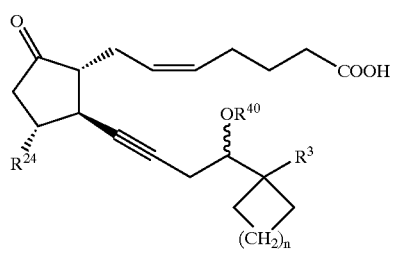
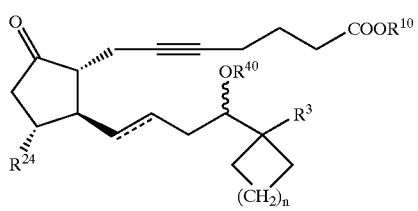
(IIIA-3)
Esterification
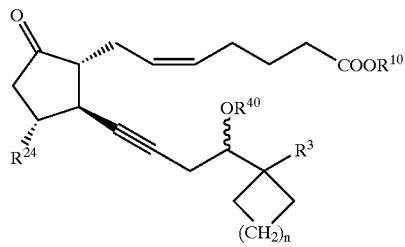
(IIIA-2)
Scheme (H)
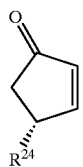
(XII)
1) 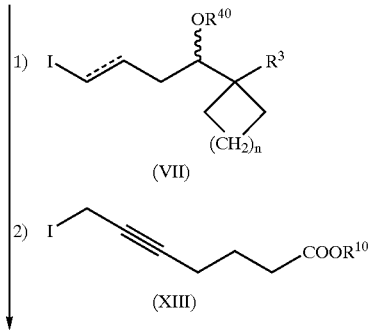
(VII)
2) I~~~~~COOR^{10}
(XIII)

Scheme (J)
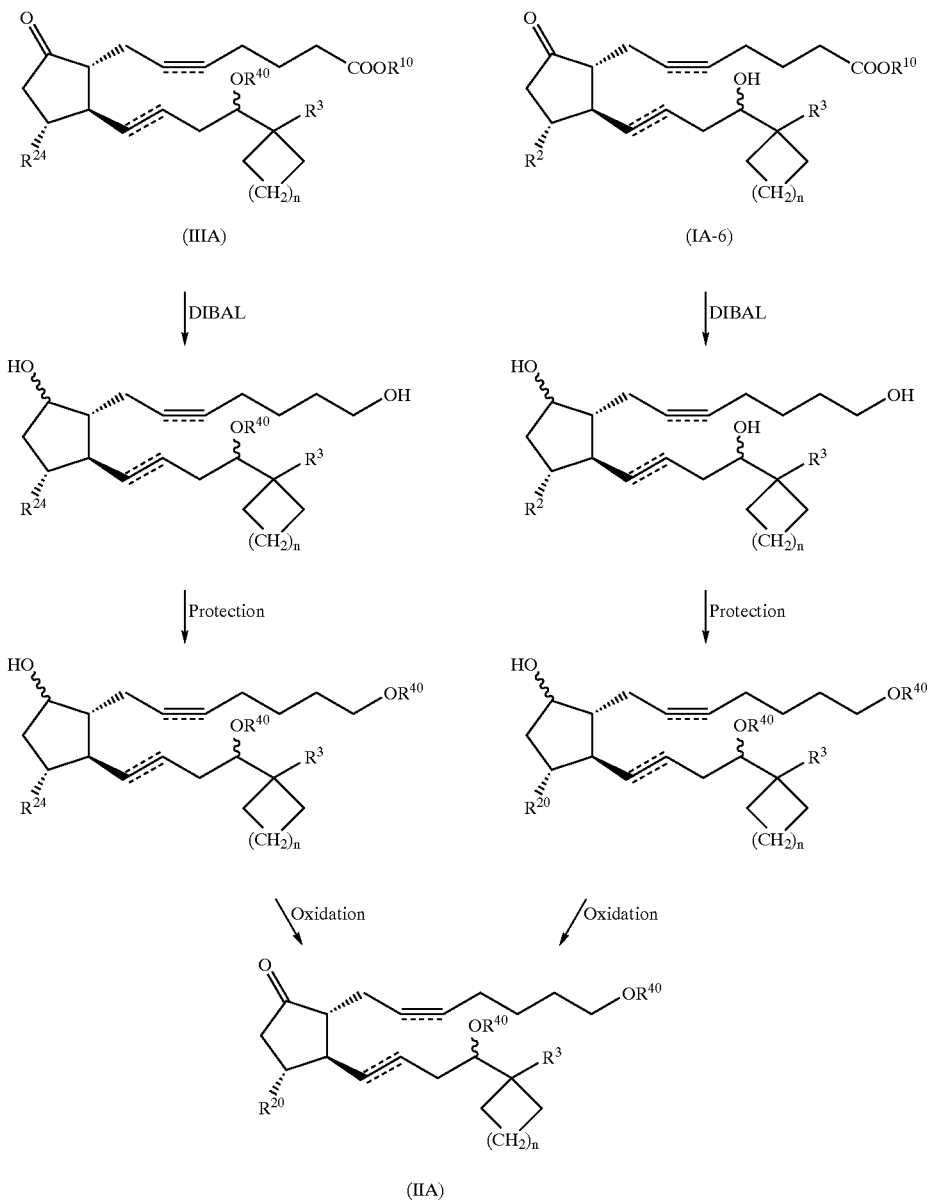

Scheme (K)
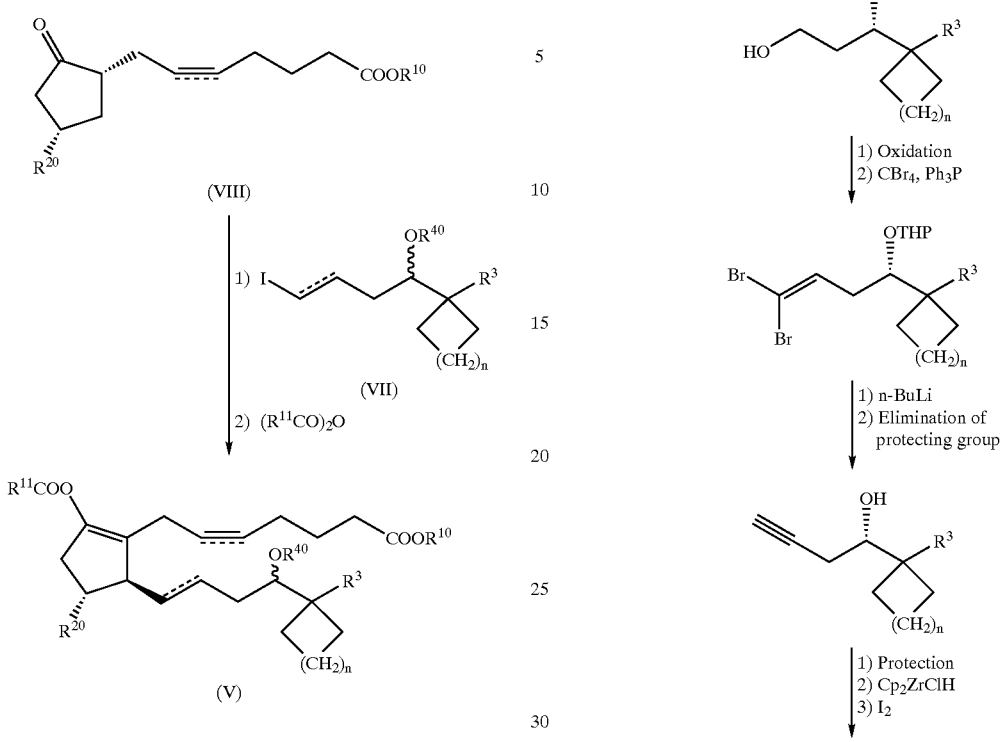
Scheme (L)
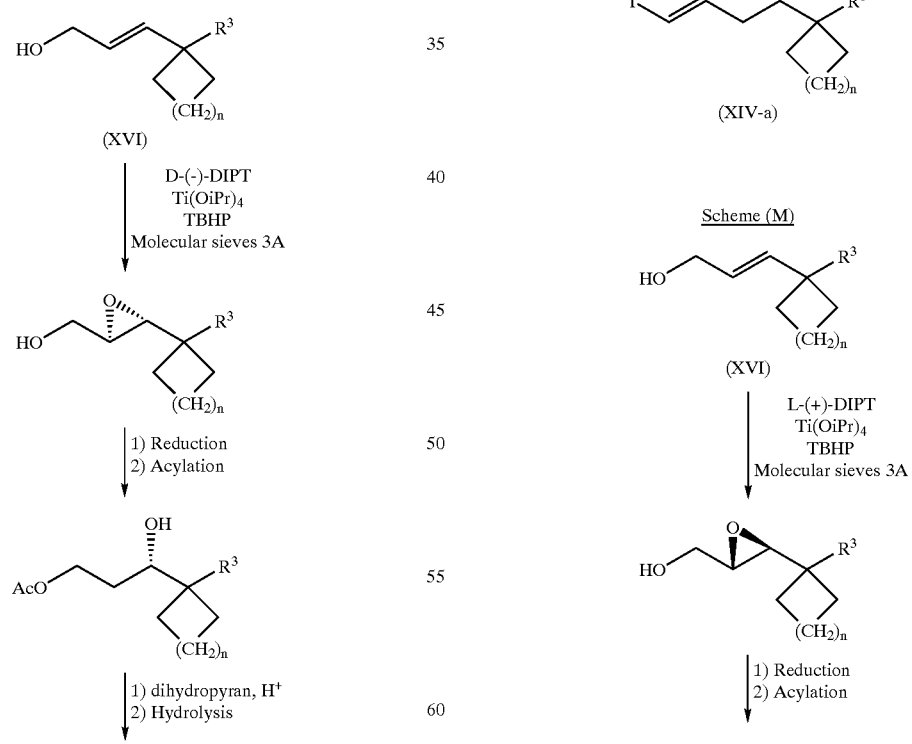
Scheme (M)
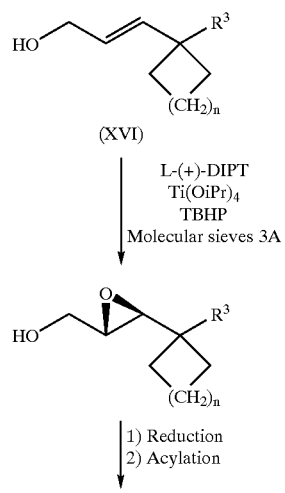

-continued

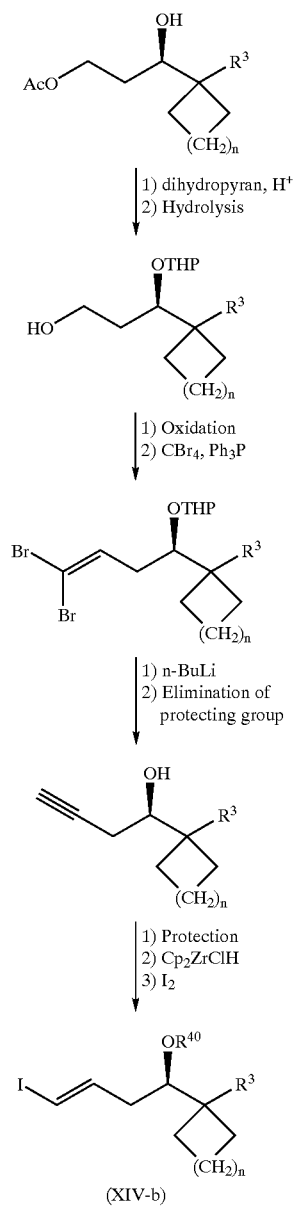

Scheme (N)

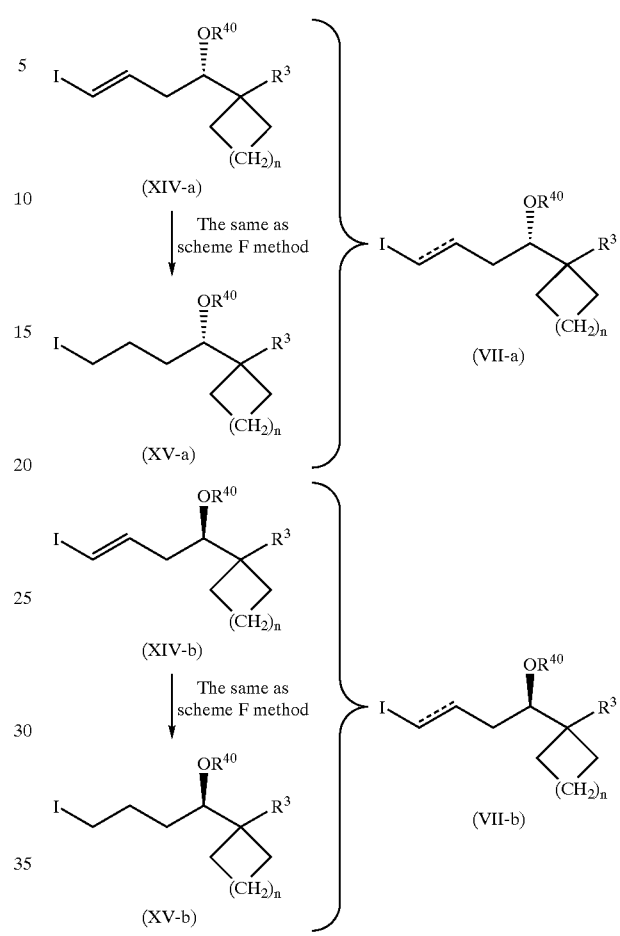

Each reaction of hereinbefore described reaction Scheme may be carried out known methods. In the reaction Scheme, The compound of formula (VI), (VIII), (X), (XII), (XIII), (XI) and (XVI) as starting materials are known per se or may be prepared by known methods.

For example, in the compound of formula (VI), (4RS)-5,5-propanooct-1-yn-4-ol is known compound described in the specification of U.S. Pat. No. 4,132,738.

In the compound of formula (VII), (5Z)-7-((3R)-3-t-butyldimethylsilyloxy-5-oxocyclopent-1-ene)hept-5-enoic acid methylester and in the compound of formula (X), (4R)-2-(diethylaminomethyl)-4-t-butyldimethylsilyloxy-2-cyclopenten-1-one is known compound described in the literature of J. Org. Chem., 53, 5590–5592 (1988).

In the compound of formula (XII), (4R)-4-t-butyldimethylsilyloxy-2-cyclopenten-1-one and in the compound of formula (XIII), 7-iodohept-5-ynoic acid methylester is known compound described in the literature of J. Am. Chem. Soc., 110, No. 14, 4718–4726 (1988).

The compound of formula (XI) is known compound described in the literature of J. Am. Chem. Soc., 97, 4745–4746 (1975).

The starting materials and reagents in the present invention are known per se or may be prepared by known methods.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activities

The compounds of the present invention of the formula (I) bind and act on $EP_2$ receptor which is a subtype of of $PGE_2$ receptor.

For example, in standard laboratory test, the effects of the compounds of the present invention were confirmed by binding assay using expression cell of prostanoide receptor subtype.

Binding Assay Using Expression Cell of Prostanoide Receptor Subtype

The preparation of membrane fraction was carried out according to the method of Sugimoto et. al. [J. Biol. Chem. 267, 6463–6466 (1992)], using expression CHO cell of the prostanoide receptor subtype (mouse $EP_1$, $EP_2$, $EP_{3\alpha}$, $EP_4$).

The standard assay mixture contained membrane fraction (0.5 mg/ml), and [$^3$H]-$PGE_2$ in a final volume of 200 μl was incubated for 1 hour at room temperature. The reaction was terminated by the addition of 3 ml of ice-cold buffer. The mixture was rapidly filtered through a GF/B glass filter. The radioactivity associated with the filter was measured by liquid scintillation counting.

Kd and Bmax values were determined from Scatchard plots [Ann. N.Y. Acad. Sci., 51, 660 (1949)]. Non-specific binding was calculated as the bound in the presence of an excess (2.5 μM) of unlabeled $PGE_2$. In the experiment for competition of specific $^3$H-PGE2 binding by the compounds of the present inventions 2.5 nM of $^3$H-PGE2 and various concentrations of compounds of the present invention were added. The following buffer was used in all reactions.

Buffer: 10 mM potassium phosphate (pH 6.0), 1 mM EDTA, 10 mM $MgCl_2$, 0.1 M NaCl In the example compounds, all of values were shown the more polar compounds.

The dissociation constant (Ki) of each compound was calculated by the following equation.

$$Ki=IC_{50}/(1+([C]/Kd))$$

The results were shown in Table 15.

TABLE 15

| Example No. | ki (μM) | | | |
|---|---|---|---|---|
| | $EP_1$ | $EP_2$ | $EP_{3\alpha}$ | $EP_4$ |
| 4 | >10 | 0.092 | >10 | >10 |
| 4(5) | >10 | 0.032 | >10 | >10 |
| 4(10) | >10 | 0.030 | >10 | >10 |
| 6(1) | >10 | 0.036 | >10 | >10 |
| 6(5) | >10 | 0.076 | >10 | >10 |
| 10 | >10 | 0.034 | >10 | >10 |
| 12 | >10 | 0.37 | >10 | >10 |
| 16(1) | >10 | 0.096 | >10 | >10 |
| 17(2) | 1.10 | 0.0009 | 2.70 | 0.40 |

Toxicity

The toxicity of the compounds of the present invention are very low and therefore, it is confirmed that these compounds are safe for pharmaceutical use.

Application for Pharmaceuticals

The compounds of the present invention of the formula (I) bind strongly and act on $PGE_2$ receptor, especially on $EP_2$ subtype receptor and therefore are useful for prevention and/or treatment of immunologic diseases (autoimmune diseases, organ transplantation, etc.), asthma, abnormal bone formation, neuronal cell death, liver damage, abortion, premature birth or retina neuropathy of glaucoma etc.

Among the compounds of the present invention of the formula (I), compounds which bind weakly on to receptor subtypes except for $EP_2$ receptors and another arachidonic acid metabolism receptors (thromboxane receptor, $PGI_2$ receptor, etc.) do not express other effects and therefore it is thought that such compounds will be a medical agent which have less side-effects.

For the purpose above described, the compounds of the formula (I), (IA), (IB) and (IC), prodrug thereof, non-toxic salts thereof and cyclodextrin clathrate thereof may be normally administered systematically or partially, usually by oral or parenteral administration. To convert prodrug, they have merit of non-stimulant, good-absorbability, good-solubility, etc.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

When administering the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules contain hard capsules and soft capsules.

In such compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate. The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluents for injection immediately before used.

Other compositions for parenteral administration include liquids for external use, and endemic liniments, ointment, suppositories and pessaries which comprise one or more of the active compound(s) and may be prepared by know methods.

REFERENCE EXAMPLES AND EXAMPLES

The following reference examples and examples are intended to illustrate, but not limit, the present invention. The solvents in parentheses show the developing or eluting solvents and the ratios of the solvents used are by volume in chromatographic separations. NMR in the parentheses show measured solvents. In the example, TBS is t-butyldimethylsilyl, THP is tetrahydropyranyl, Ac is acetyl, EE is ethoxyethyl.

Reference Example 1

(4RS)-4-t-butyldimethylsilyloxy-5,5-propanoocta-1-yne

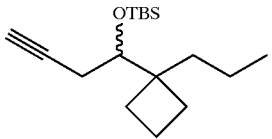

To the mixture solution of (4RS)-5,5-propanoocta-1-yne-4-ol (4.0 g) and imidazole (4.9 g) in dimethylformamide (50 ml) was added t-butyldimethylsilylchloride (5.4 g) under cooling with ice. The reaction mixture was stirred at 60° C. for 7 hours. The reaction mixture was quenched by addition of water, extracted with ethyl acetate. The extract was washed with a saturated aqueous solution of sodium chloride, dried over anhydrous magnesium sulfate and concentrated. The residue was purified by column chromatography on silica gel (hexane→hexane:ethyl acetate=10:1) to give the tittle compound (6.8 g) having the following physical data.

TLC: Rf 0.64 (hexane);

NMR (CDCl$_3$): δ3.75 (1H, t, J=5.8 Hz), 2.28 (1H, ddd, J=17, 5.0, 2.5 Hz), 2.16 (1H, ddd, J=17, 6.0, 2.5 Hz), 2.10–1.94 (1H, m), 1.92 (1H, t, J=2.5 Hz), 1.90–1.20 (9H, m), 0.90 (3H, t, J=6.0 Hz), 0.89 (9H, s), 0.12 (3H, s), 0.07 (3H, s).

Reference Example 2

(1E,4RS)-1-iodo-4-t-butyldimethylsilyloxy-5,5-propanoocta-1-ene

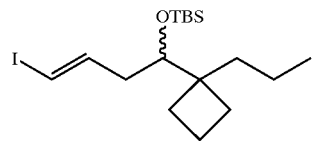

To the mixture of the compound prepared in reference example 1 (3.0 g) and tributyltinhydride (3.7 ml) was added azobisisobutylonitrile (35 mg). The mixture was stirred at 80° C. for 1.5 hours. After the mixture was cooled to room temperature, to the mixture was added dropwise iodine (4.1 g) in dichloromethane (70 ml). The reaction mixture was stirred for 10 min. To the reaction mixture was added a saturated aqueous solution of sodium thiosulfate, ethyl acetate and a saturated aqueous solution of sodium chloride, stirred, filtered, and extracted. The water layer was extracted with ethyl acetate. The organic layer was washed with a saturated aqueous solution of sodium chloride, dried over anhydrous magnesium sulfate and concentrated. The residue was purified by column chromatography on silica gel (hexane) to give the tittle compound (3.9 g) having the following physical data.

TLC: Rf 0.77 (hexane);

NMR (CDCl$_3$): δ6.49 (1H, dt, J=14.5, 7.5 Hz), 5.97 (1H, d, J=14.5 Hz), 3.58 (1H, t, J=6.0 Hz), 2.20–1.20 (12H, m), 0.91 (3H, t, J=6.0 Hz), 0.91 (9H, s) 0.06 (3H, s), 0.05 (3H, s).

Reference Example 3

(5Z,11α,13E,16RS)-11,16-bis(t-butyldimethylsilyloxy)-9-oxo-17,17-propanoprosta-5,13-dienoic acid.methylester

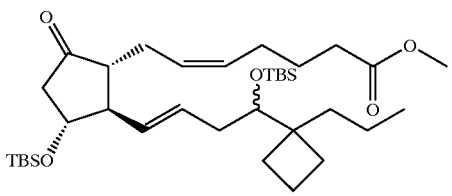

To a solution of (1E,4RS)-1-iodo-4-t-butyldimethylsilyloxy-5,5-propanoocta-1-ene (368 mg) in ether (6 ml) was added dropwise 1.7 M t-butyllithium in pentane solution (1.06 ml) at −78° C. After the mixture was stirred for 45 min, to the mixture was added 0.25 M lithium 2-thienylcyanocuprate in tetrahydrofuran (4.33 ml). After the mixture was stirred for 20 min at same temperature, to the mixture was added dropwise a solution of (5Z)-7-((3R)-3-t-butyldimethylsilyloxy-5-oxocyclopenta-1-ene)hepta-5-enoic acid.methylester (290 mg) in ether (4 ml). The reaction mixture was warmed up to 0° C. for 1 hour. The reaction mixture was quenched by addition of a saturated aqueous solution of sodium ammonium, extracted with ethyl acetate. The extract was washed with a saturated aqueous solution of ammonium chloride and a saturated aqueous solution of sodium chloride, successively, dried over anhydrous magnesium sulfate and concentrated. The residue was purified by column chromatography on silica gel (hexane:ethyl acetate=25:1) to give the tittle compound (332 mg) having the following physical data.

TLC: Rf 0.37 (hexane:ethyl acetate=10:1);

NMR (CDCl$_3$): δ5.75–5.45 (1H, m), 5.45–5.20 (3H, m), 4.01 (1H, q, J=7.0 Hz), 3.66 (3H, s), 3.57 (1H, t, J=4.5 Hz), 2.60 (1H, dd, J=17.5, 6.5 Hz) 2.54–2.24 (3H, m), 2.30 (2H, t, J=7.0 Hz), 2.24–1.96 (6H, m), 1.96–1.20 (12H, m), 0.95 (3H, m), 0.91 (9H, s), 0.88 (9H, s), 0.06 (3H, s), 0.05 (3H, s), 0.04 (3H, s), 0.03 (3H, s).

Reference Example 4

(4RS)-4-t-butyldimethylsilyloxy-5,5-propanoocta-1-ene

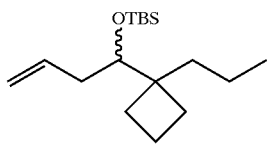

To a solution of the compound prepared in reference example 2 (629 mg) in anhydrous ether (10 ml) was added dropwise 1.57 M t-butyllithium in pentane solution (1.96 ml) at −78° C. The reaction mixture was stirred for 1 hour. The reaction mixture was quenched by addition of a saturated aqueous solution of ammonium chloride (20 ml), extracted with hexane (×2). The extract was washed with a saturated aqueous solution of sodium chloride, dried over anhydrous magnesium sulfate and concentrated. The residue was purified by column chromatography on silica gel (hexane) to give the tittle compound (434 mg) having the following physical data.

TLC: Rf 0.75 (hexane);

NMR (CDCl$_3$): δ5.83 (1H, ddt, J=17, 9.8, 7.4 Hz), 5.06–4.92 (2H, m), 3.59 (1H, dd, J=6.0, 4.6 Hz), 2.20–2.00 (2H, m), 2.00–1.20 (10H, m), 0.90 (3H, t, J=5.0 Hz), 0.83 (9H, s), 0.03 (6H, s).

Reference Example 5

(4RS)-4-t-butyldimethylsilyloxy-5,5-propanooctan-1-ol

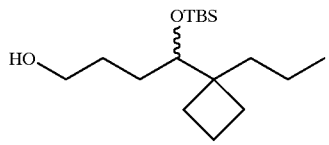

To a borane-tetrahydrofuran complex (2.3 ml, 1.0 M tetrahydrofuran solution) was added dropwise cyclohexene (468 μl) at 0° C. under an atmosphere of argon. The mixture was stirred for 1.5 hours. To the mixture was added dropwise a solution of the compound prepared in reference example 4 (434 mg) in tetrahydrofuran (10 ml) at 0° C. The reaction mixture was stirred for 30 min at same temperature, and stirred for 30 min at room temperature. To the reaction was added 1N aqueous solution of sodium hydroxide and 31% aqueous solution of hydroperoxide (3 ml). The mixture was stirred at room temperature for 30 min. The reaction mixture was quenched by addition of a saturated aqueous solution of sodium thiosulfate (5 ml), extracted with ether. The extract was washed with a saturated aqueous solution of sodium thiosulfate and a saturated aqueous solution of sodium chloride, successively, dried over anhydrous magnesium sulfate and concentrated. The residue was purified by column chromatography on silica gel (hexane→ethyl acetate) to give the tittle compound (439 mg) having the following physical data.

TLC: Rf 0.52 (hexane:ethyl acetate=4:1);

NMR (CDCl$_3$): δ3.61 (2H, t, J=6.2 Hz), 3.55 (1H, t, J=4.6 Hz), 2.18–1.20 (14H, m), 0.95–0.85 (12H, m), 0.05 (6H, s).

Reference Example 6

(4RS)-4-t-butyldimethylsilyloxy-1-iodo-5,5-propanooctane

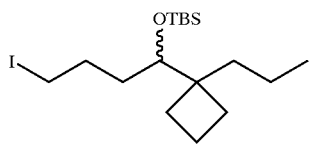

To a solution of the compound prepared in reference example 5 (430 mg) in anhydrous benzene (10 ml) was successively added imidazole (243 mg), triphenylphosphine (936 mg) and iodine (726 mg). The reaction mixture was stirred for 15 min. The reaction mixture was quenched by addition of a saturated aqueous solution of sodium thiosulfate, extracted with benzene (×2). The extract was washed with a saturated aqueous solution of sodium chloride (×2), dried over anhydrous magnesium sulfate and concentrated. The residue was purified by column chromatography on silica gel (hexane) to give the tittle compound (553 mg) having the following physical data.

TLC: Rf 0.63 (hexane);

NMR (CDCl$_3$): δ3.54 (1H, t, J=5.0 Hz), 3.16 (2H, t, J=6.8 Hz), 2.17–1.22 (14H, m), 0.95–0.85 (12H, m), 0.09 (3H, s).

Reference Example 7

(3R,4R)-4-t-butyldimethylsilyloxy-2-methyliden-3-((4RS)-4-t-butyldimethylsilyloxy-5,5-propanoocta-1-yne-1-yl)cyclopentanone

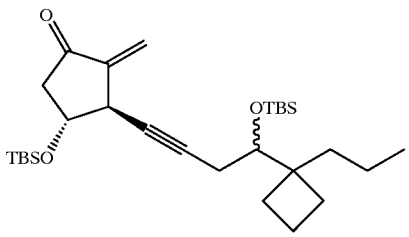

To a solution of (4RS)-t-butyldimethylsilyloxy-5,5-propanoocta-1-yne (730 mg) in toluene (5 ml) was added dropwise 1.6 M n-butyllithium in hexane solution (1.6 ml). After the mixture was stirred for 30 min, to the mixture was added dropwise 0.95 M diethylaluminum chloride in hexane solution (2.95 ml). After the mixture was stirred for 30 min, to the mixture was added dropwise a solution of (4R)-2-(diethylaminomethyl)-4-t-butyldimethylsilyloxy-2-cyclopenten-1-one (595 mg) in toluene (8 ml). The reaction mixture was stirred at room temperature for 15 min. The reaction mixture was quenched by addition of a saturated aqueous solution Of ammonium chloride and 2N aqueous solution of hydrochloric acid, extracted with hexane the extract was washed with a saturated aqueous solution of sodium hydrogencarbonate, dried over anhydrous magnesium sulfate and concentrated. The residue was purified by column chromatography on silica gel (hexane:ethyl acetate= 100:1) to give the tittle compound (364 mg) having the following physical data.

TLC: Rf 0.77(hexane:ethyl acetate=10:1);

NMR (CDCl$_3$): δ6.12 (1H, d, J=3.0 Hz), 5.53 (1H, d, J=3.0 Hz), 4.25 (1H, m), 3.71 (1H, t, J=5.3 Hz), 3.50–3.40 (1H, m), 2.70 (1H, dd, J=18.0, 6.4 Hz), 2.40–1.20 (13H, m), 0.95–0.82 (21H, m), 0.18–0.02 (12H, m).

Reference Example 8

(2R,3R,4R)-4-t-butyldimethylsilyloxy-2-((2Z)-7-(1-ethoxyethoxy)-hepta-2-en-1-yl)-3-((4RS)-4-t-butyldimethylsilyloxy-5,5-propanoocta-1-yne-1-yl)cyclopentanone

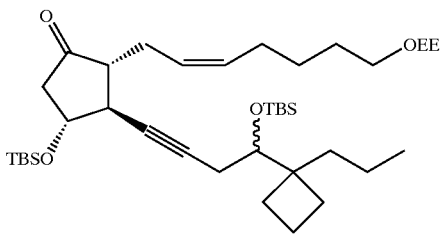

To a solution of (1Z)-1-iodo-6-(1-ethoxyethoxy)hexa-1-ene (537 mg) in ether (5 ml) was added dropwise 1.57 M t-butyllithium in pentane solution (2.30 ml) at −78° C. After the mixture was stirred for 1.5 hours, to the mixture was added 0.25 M lithium 2-thienylcyanocuprate in tetrahydrofuran (8.00 ml). After the mixture was stirred for 30 min at same temperature, to the mixture was added dropwise a solution of the compound prepared in reference example 7 (606 mg) in ether (10 ml). The reaction mixture was warmed up to 0° C. for 1 hour. The reaction mixture was quenched by addition of a saturated aqueous solution of sodium ammonium, extracted with hexane. The extract was washed with a saturated aqueous solution of sodium chloride, dried over anhydrous magnesium sulfate and concentrated. The residue was purified by column chromatography on silica gel (hexane:ethyl acetate=60:1→30:1) to give the tittle compound (585 mg) having the following physical data.

TLC: Rf 0.57 (hexane:ethyl acetate=6:1);

NMR (CDCl$_3$): δ5.57–5.28 (2H, m), 465 (1H, q, J=5.0 Hz), 4.32–4.03 (1H, m), 3.73–3.35 (5H, m), 2.74–2.60 (2H, m), 2.47–1.18 (28H, m), 0.96–0.80 (21H, m), 0.13–0.05 (12H, m).

Reference Example 9

(5Z, 11α, 16RS)-11,16-bis(t-butyldimethylsilyloxy)-9-oxo-17,17-propanoprosta-5-ene-13-yne-1-ol

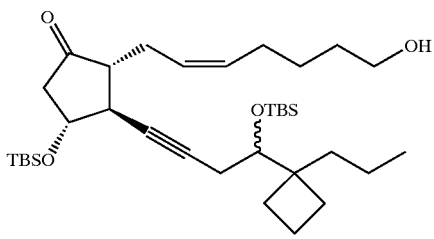

To a solution of the compound prepared in reference example 8 (643 mg) in methanol (14 ml) was added pyridinium p-toluenesulfonate (24 mg) at 0° C. The reaction mixture was stirred at room temperature for 5 hours. The reaction mixture was quenched by addition of a saturated aqueous solution of sodium hydrogencarbonate, extracted with ethyl acetate. The extract was washed with a saturated aqueous solution of sodium chloride, dried over anhydrous magnesium sulfate and concentrated. The residue was purified by column chromatography on silica gel (hexane:ethyl acetate=10:1) to give the tittle compound (399 mg) having the following physical data.

TLC: Rf 0.37 (hexane:ethyl acetate=4:1);

NMR (CDCl$_3$): δ5.60–5.30 (2H, m), 4.32–4.22 (1H, m), 3.70 (1H, t, J=6.0 Hz), 3.64 (2H, t, J=7.0 Hz),2.72–2.60 (1H, m), 2.66 (1H, dd, J=17.8, 6.6 Hz), 2.47–1.32 (23H, m), 0.95–0.83 (21H, m), 0.18–0.03 (12H, m).

Reference Example 10

(5Z,11α,16RS)-11,16-bis(t-butyldimethylsilyloxy)-9-oxo-17,17-propanoprosta-5-ene-13-ynoic acid.methylester

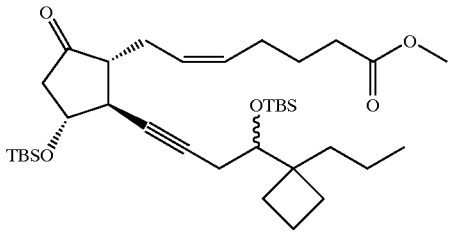

To a solution of the compound prepared in reference example 9 (369 mg) in acetone (10 ml) was added dropwise Jones reagent (a aqueous solution of chromium (VI) oxide and sulfuric acid, 2.0 M containing as chromic acid, 1.0 ml) at −30° C. The reaction mixture was stirred for 1 hour. To the reaction mixture added isopropyl alcohol (3 ml), diluted with water, extracted with ethyl acetate. The extract was washed with a saturated aqueous solution of sodium chloride, dried over anhydrous magnesium sulfate and concentrated until the volume of 50 ml. To the residue solution was added a solution of diazomethane in ether until the reaction solution changed yellow color. The reaction mixture was concentrated under reduced pressure. The residue was purified by column chromatography on silica gel (hexane:ethyl acetate=100:1) to give the tittle compound (257 mg) having the following physical data.

TLC: Rf 0.76 (hexane:ethyl acetate=4:1);

NMR (CDCl$_3$): δ5.49–5.35 (2H, m), 4.32–4.22 (1H, m), 3.69 (1H, t, J=4.8 Hz), 3.66 (3H, s), 2.73–2.61 (12H, m), 2.44–1.32 (20H, m), 2.31 (2H, t, J=7.6 Hz), 0.95–0.82 (21H, m), 0.13–0.06 (12H, m).

Reference Example 11

(11α,13E,16RS)-11,16-bis(t-butyldimethylsilyloxy)-9-oxo-17,17-propanoprosta-13-ene-5-ynoic acid.methylester

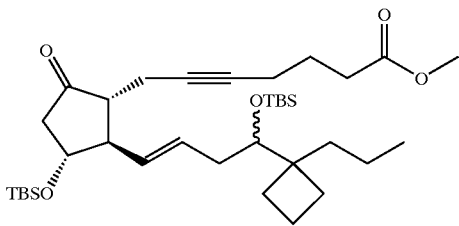

To a solution of (1E,4RS)-1-iodo-4-t-butyldimethylsilyloxy-5,5-propanoocta-1-ene (265 mg) in ether (2 ml) was added dropwise 1.7 M t-butyllithium in pentane solution (0.83 ml) at −78° C. After the mixture was stirred for 1 hour, to the mixture was added 0.25 M lithium 2-thienylcyanocuprate in tetrahydrofuran (3.12 ml). After the mixture was stirred for 20 min at same temperature, to the mixture was added dropwise a solution of (4R)-4-t-butyldimethylsilyloxy-2-cyclopenten-1-one (106 mg) in tetrahydrofuran (4 ml). The reaction mixture was warmed up to −20° C. for 30 min. To the reaction mixture was added dropwise a solution of 7-iodohepta-5-ynoic acid methylester (665 mg) in tetrahydrofuran (5 ml). The reaction mixture was stirred for 3 hours. The reaction mixture was quenched by addition of a saturated aqueous solution of ammonium chloride extracted with hexane. The extract was washed with a saturated aqueous solution of sodium chloride, dried over anhydrous magnesium sulfate and concentrated. The residue was purified by column chromatography on silica gel (hexane:ethyl acetate=50:1→20:1) to give the tittle compound (44 mg) having the following physical data.

TLC: Rf 0.36(hexane:ethyl acetate=9:1);

NMR (CDCl$_3$): δ5.78–5.55 (1H, m), 5.40–5.23 (1H, m), 4.10–3.95 (1H, m), 3.66 (3H, s), 3.63–3.53 (1H, m), 2.80–2.50 (2H, m), 2.50–1.20 (22H, m), 1.00–0.80 (3H, m), 0.91, 0.90 and 0.88 (18H, 3s), 0.09, 0.05 and 0.04 (12H, 3s).

Example 1

(5Z,11α,13E)-11,16-dihydroxy-9-oxo-17,17-propanoprosta-5,13-dienoic acid.methylester

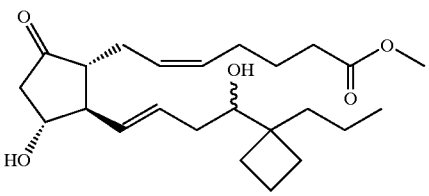

To a solution of the compound prepared in reference example 3 (330 mg) in acetonitrile (7 ml) was added pyridine (3 ml) and 47% a aqueous solution of hydrofluoric acid (6 ml). The reaction mixture was stirred at room temperature for 5 hours. The reaction mixture quenched by addition of water, extracted with ethyl acetate. The extract was washed with a saturated aqueous solution of sodium hydrogencarbonate and a saturated aqueous solution of sodium chloride, successively, dried over anhydrous magnesium sulfate and concentrated. The residue was purified by column chromatography on silica gel (hexane:ethyl acetate=1:1) to give the present invention each stereomer on 16-position less polar compound (55 mg) and more polar compound (55 mg)

Less Polar

TLC: Rf 0.37 (hexane:ethyl acetate=2:3);

NMR (CDCl$_3$): δ5.71 (1H, ddd, J=15.3, 7.6, 6.3 Hz), 5.54–5.26 (3H, m), 4.18–4.00 (1H, m), 3.67 (3H, s), 3.55 (1H, dd, J=10.0, 2.4 Hz), 2.75 (1H, ddd J=18.6, 7.2, 1.0 Hz), 2.85–2.65 (1H, br), 2.50–1.50 (19H, m), 2.32 (2H, t, J=7.5 Hz), 1.50–1.20 (3H, m), 0.94 (3H, t, J=6.9 Hz).

More Polar

TLC: Rf 0.29 (hexane:ethyl acetate=2:3);

NMR (CDCl$_3$): δ5.69 (1H, ddd, J=15.4, 8.2, 5.4 Hz), 5.49–5.25 (3H, m), 4.12–3.98 (1H, m), 3.67 (3H, s), 3.65–3.20 (1H, br), 3.55 (1H, dd, J=10.2, 2.4 Hz), 2.74 (1H, ddd, J=18.4, 7.4, 1.0 Hz), 2.50–1.50 (19H, m), 2.31 (2H, t, J=7.3 Hz), 1.50–1.20 (3H, m), 0.94 (3H, t, J=6.9 Hz).

Example 1(1)~1(2)

By the same procedure as provided in example 1, using the compound prepared in reference example 10 or reference example 11, compounds of the present invention having the following physical data were obtained.

Example 1(1)

(5Z,11α,16RS)-11,16-dihydroxy-9-oxo-17,17-propanoprosta-5-ene-13-ynoic acid.methylester

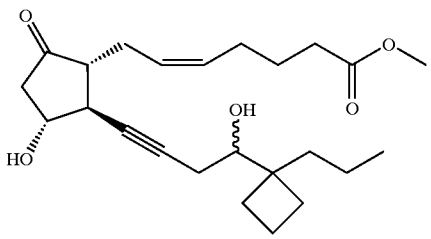

mixture
TLC: Rf 0.57 (hexane:ethyl acetate=1:2);
NMR (CDCl$_3$): δ5.54–5.31 (2H, m), 4.39–4.27 (1H, m), 3.70–3.63 (1H, m), 3.67 (3H, s), 3.40–3.30 (1H, brs), 2.75 (1H, dd, J=18.4, 7.2 Hz), 2.72–1.20 (24H, m), 0.93 (3H, t, J=7.0 Hz).

Example 1(2)

(11α,13E)-11,16-dihydroxy-9-oxo-17,17-propanoprosta-13-ene-5-ynoic acid.methylester

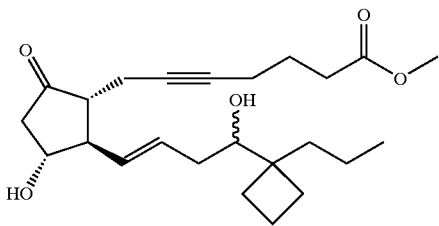

Less Polar
TLC: Rf 0.33 (hexane:ethyl acetate=1:2);
NMR (CDCl$_3$): δ5.80 (1H, ddd, J=15.4, 7.6, 6.2 Hz), 5.52 (1H, dd, J=15.4, 8.2 Hz), 4.22–4.06 (1H, m), 3.68 (3H, s), 3.59 (1H, dd, J=9.8, 2.8 Hz), 2.90–2.55 (3H, m), 2.50–1.20 (21H, m), 2.43 (2H, t, J=7.6 Hz), 0.94 (3H, t, J=6.8 Hz).

More Polar
TLC: Rf 0.24 (hexane:ethyl acetate=1:2);
NMR (CDCl$_3$): δ5.76 (1H, ddd, J=15.4, 8.2, 5.4 Hz), 5.46 (1H, dd, J=15.4, 8.6 Hz), 4.19–4.03 (1H, m), 3.68 (3H, s), 3.58 (1H, dd, J=10.0, 2.2 Hz), 2.90–2.55 (3H, m), 2.50–1.20 (21H, m), 2.43 (2H, t, J=7.4 Hz), 0.94 (3H, t, J=6.8 Hz).

Example 2

(5Z,11α,16RS)-11,16-dihydroxy-9-oxo-17,17-propanoprosta-5-enoic acid methylester

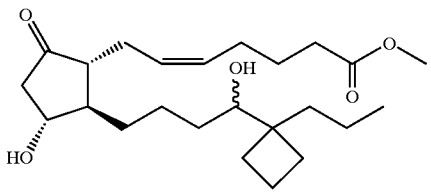

By the same procedure as provided in reference example 3→example 1, using the compound prepared in reference example 6, compound of the present invention having the following physical data was obtained.

mixture
TLC: Rf 0.34 (hexane:ethyl acetate=1:2);
NMR (CDCl$_3$): δ5.51–5.28 (2H, m), 4.28–4.16 (1H, m), 3.67 (3H, s), 3.55–3.50 (1H. m), 2.68 (1H, ddd, J=19, 7, 3 Hz), 2.50–1.20 (25H, m), 2.33 (2H, t, J=7 Hz), 0.93 (3H, t, J=7 Hz).

Example 3~3(9)

By the same procedure as provided in reference example 1→reference example 2→reference example 3→example 1, using corresponding acetylene derivatives instead of (4RS)-5,5-propanoocta-1-yne-4-ol as starting material in reference example 1, compounds of the present invention having the following physical data were obtained.

Example 3

(5Z,11α,13E)-11,16-dihydroxy-20-methyl-9-oxo-17,17-propanoprosta-5,13-dienoic acid.methylester

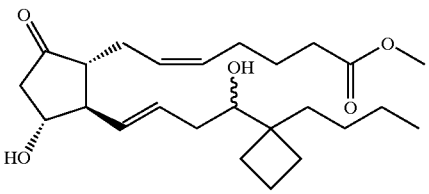

Less Polar
TLC: Rf 0.32 (hexane:ethyl acetate=1:1);
NMR (CDCl$_3$): δ5.71 (1H, ddd, J=15, 8, 6 Hz), 5.52–5.27 (3H, m), 4.17–4.03 (1H, m), 3.67 (3H, s), 3.54 (1H, dd, J=10, 2 Hz), 2.75 (1H, dd, J=19, 8 Hz), 2.50–1.90 (9H, m), 2.30 (2H, t, J=7 Hz), 1.90–1.20 (14H, m), 0.90 (3H, t, J=7 Hz).

More Polar
TLC: Rf 0.28 (hexane:ethyl acetate=1:1);
NMR (CDCl$_3$): δ5.71 (1H, ddd, J=15, 8, 6 Hz), 5.50–5.27 (3H, m), 4.17–4.00 (1H, m), 3.66 (3H, s), 3.56 (1H, dd, J=10, 2 Hz), 2.74 (1H, dd, J=17, 6 Hz), 2.48–1.20 (23H, m), 2.30 (2H, t, J=7 Hz), 0.92 (3H, t, J=7 Hz).

Example 3(1)

(5Z,11α,13E)-11,16-dihydroxy-20-ethyl-9-oxo-17,17-propanoprosta-5,13-dienoic acid.methylester

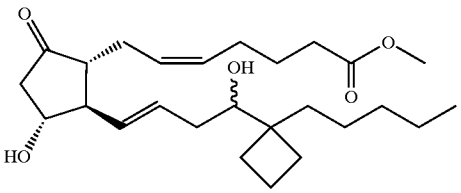

Less Polar
TLC: Rf 0.31 (hexane:ethyl acetate=1:1);
NMR (CDCl$_3$): δ5.71 (1H, ddd, J=15, 8, 6 Hz), 5.52–5.27 (3H, m), 4.15–4.02 (1H, m), 3.67 (3H, s), 3.54 (1H, dd, J=10, 2 Hz), 2.75 (1H, dd, J=19, 8 Hz) 2.50–1.90 (9H, m), 2.32 (2H, t, J=7 Hz), 1.90–1.20 (16H, m), 0.90 (3H, t, J=7 Hz).

More Polar
TLC: Rf 0.27 (hexane:ethyl acetate=1:1);
NMR (CDCl$_3$): δ5.72 (1H, ddd, J=15, 8, 6 Hz), 5.49–5.27 (3H, m), 4.12–3.99 (1H, m), 3.66 (3H, s), 3.55 (1H, dd, J=10, 2 Hz), 2.75 (1H, dd, J=19, 8 Hz), 2.50–1.90 (9H, m), 2.33 (2H, t, J=7 Hz), 1.90–1.10 (16H, m), 0.90 (3H, t, J=7 Hz).

Example 3(2)

(5Z,11α,13E)-20-chloro-11,16-dihydroxy-9-oxo-17, 17-propanoprosta-5,13-dienoic acid.methylester

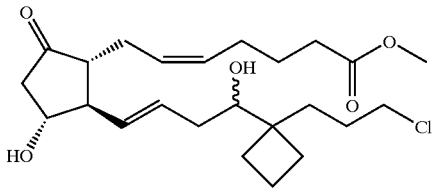

Less Polar

TLC: Rf 0.24 (hexane:ethyl acetate=1:2);

NMR (CDCl₃): δ5.70 (1H, ddd, J=15, 8, 6 Hz), 5.53–5.26 (3H, m), 4.17–4.03 (1H, m), 3.67 (3H, s), 3.59–3.53 (3H, m), 2.76 (1H, dd, J=18, 8 Hz), 2.50–1.45 (21H, m), 2.30 (2H, t, J=7 Hz).

More Polar

TLC: Rf 0.18 (hexane:ethyl acetate=1:2);

NMR (CDCl₃): δ5.70 (1H, ddd, J=15, 8, 6 Hz), 5.50–5.26 (3H, m), 4.17–4.00 (1H, m), 3.66 (3H, s), 3.59–3.53 (3H, m), 2.74 (1H, dd, J=19, 7 Hz), 2.50–1.50 (21H, m), 2.30 (2H, t, J=7 Hz).

Example 3(3)

(5Z,11α,13E)-11,16-dihydroxy-9-oxo-18-phenyl-17, 17-propano-19,20-dinorprosta-5,13-dienoic acid.methylester

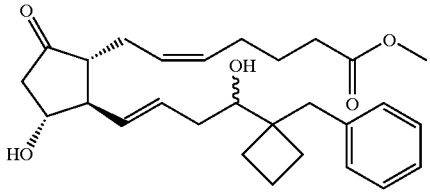

Less Polar

TLC: Rf 0.29 (hexane:ethyl acetate=1:2);

NMR (CDCl₃): δ7.33–7.20 (5H, m), 5.70 (1H, ddd, J=15, 8, 6 Hz), 5.54–5.27 (3H, m), 4.18–4.03 (1H, m), 3.66 (3H, s), 3.57 (1H, dd, J=10, 2 Hz), 2.92 (1H, d, J=13 Hz), 2.76 (1H, dd, J=19, 7 Hz), 2.65 (1H, d, J=13 Hz), 2.50–1.45 (17H, m), 2.30 (2H, t, J=7 Hz).

More Polar

TLC: Rf 0.21 (hexane:ethyl acetate=1:2);

NMR (CDCl₃): δ7.36–7.18 (5H, m), 5.70 (1H, ddd, J=15, 8, 6 Hz), 5.49–5.26 (3H, m), 4.18–3.99 (1H, m), 3.65 (3H, s), 3.57 (1H, dd, J=10, 2 Hz), 2.91 (1H, d, J=14 Hz), 2.73 (1H, dd, J=18, 7 Hz), 2.66 (1H, d, J=14 Hz), 2.50–1.45 (17H, m), 2.30 (2H, t, J=7 Hz).

Example 3(4)

(5Z,11α,13E)-11,16-dihydroxy-9-oxo-17,17-propanoprosta-5,13,19-trienoic acid.methylester

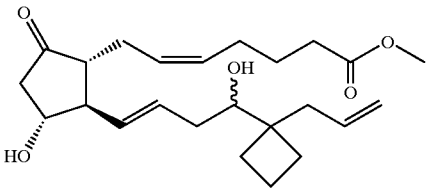

Less Polar

TLC: Rf 0.44 (hexane:ethyl acetate=1:2);

NMR (CDCl₃): δ5.95 (1H, ddt, J=17.0, 10.0, 7.4 Hz), 5.71 (1H, ddd, J=15.4, 7.7, 5.9 Hz), 5.60–5.25 (3H, m), 5.20–5.05 (2H, m), 4.16–4.02 (1H, m), 3.67 (3H, s), 3.56 (1H, dd, J=9.6, 2.0 Hz), 2.76 (1H, ddd, J=18.3, 7.3, 1.4 Hz), 2.50–1.55 (21H, m), 2.32 (2H, t, J=7.5 Hz).

More Polar

TLC: Rf 0.34 (hexane:ethyl acetate=1:2);

NMR (CDCl₃): δ5.95 (1H, ddt, J=17.2, 10.0, 7.4 Hz), 5.70 (1H, ddd, J=15.4, 7.6, 5.6 Hz), 5.57–5.25 (3H, m), 5.20–5.05 (2H, m), 4.14–3.98 (1H, m), 3.67 (3H, s), 3.56 (1H, dd, J=10.2, 2.3 Hz), 3.00–2.70 (1H, br), 2.74 (1H, ddd, J=18.2, 7.4, 1.4 Hz), 2.50–1.55 (20H, m), 2.32 (2H, t, J=7.5 Hz).

Example 3(5)

(5Z,11α,13E)-11,16-dihydroxy-20-methyl-9-oxo-17, 17-propanoprosta-5,13-diene-19-ynoic acid.methylester

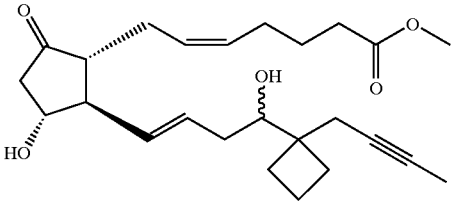

Less Polar

TLC: Rf 0.43 (hexane:ethyl acetate=1:2);

NMR (CDCl₃): δ5.83–5.66 (1H, m), 5.55–5.25 (3H, m), 4.18–4.00 (1H, m), 3.75–3.60 (1H, m), 3.67 (3H, s), 2.75 (1H, ddd, J=18.4, 7.4, 1.4 Hz), 2.50–1.55 (21H, m), 2.32 (2H, t, J=7.4 Hz), 1.80 (3H, t, J=2.6 Hz).

More Polar

TLC: Rf 0.33 (hexane:ethyl acetate=1:2);

NMR (CDCl₃): δ5.72 (1H, ddd, J=15.0, 7.8, 5.8 Hz), 5.52–5.25 (3H, m), 4.15–3.98 (1H, m), 3.73–3.62 (1H, m), 3.67 (3H, s), 2.74 (1H, ddd, J=18.4, 7.2, 1.4 Hz), 2.50–1.50 (21H, m), 2.32 (2H, t, J=7.2 Hz), 1.80 (3H, t, J=2.6 Hz).

Example 3(6)

(5Z,11α,13E)-17,17-butano-11,16-dihydroxy-9-oxoprosta-5,13-dienoic acid.methylester

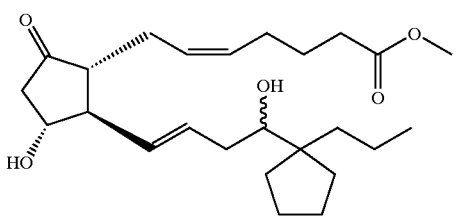

Less Polar

TLC: Rf 0.43 (hexane:ethyl acetate=2:3);

NMR (CDCl$_3$): δ5.71 (1H, ddd, J=15.2, 7.9, 5.7 Hz), 5.54–5.25 (3H, m), 4.14–4.01 (1H, m), 3.67 (3H, s), 3.47 (1H, dd, J=10.2, 2.0 Hz), 2.75 (1H, ddd, J=18.4, 7.4, 1.0 Hz), 2.50–1.80 (10H, m), 2.32 (2H, t, J=7.4 Hz), 1.80–1.50 (9H, m), 1.50–1.20 (6H, m), 0.90 (3H, t, J=6.8 Hz).

More Polar

TLC: Rf 0.34 (hexane:ethyl acetate=2:3);

NMR (CDCl$_3$): δ5.67 (1H, ddd, J=15.2, 8.2, 5.2 Hz), 5.48–5.25 (3H, m), 4.12–3.96 (1H, m), 3.70–3.40 (1H, br), 3.67 (3H, s), 3.48 (1H, dd, J=10.2, 2.0 Hz), 2.75 (1H, ddd, J=18.4, 7.6, 1.0 Hz), 2.50–1.80 (10H, m), 2.31 (2H, t, J=7.5 Hz), 1.80–1.50 (8H, m), 1.50–1.20 (6H, m), 0.90 (3H, t, J=6.6 Hz).

Example 3(7)

(5Z,11α,13E)-11,16-dihydroxy-9-oxo-17,17-pentanoprosta-5,13-dienoic acid.methylester

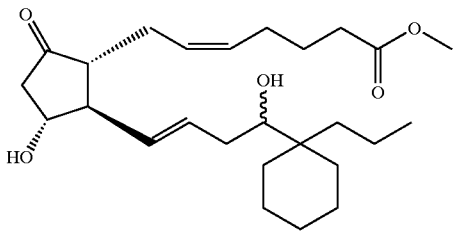

Less Polar

TLC: Rf 0.47 (hexane:ethyl acetate=2:3);

NMR (CDCl$_3$): δ5.71 (1H, ddd, J=15.4, 8.0, 5.6 Hz), 5.53–5.25 (3H, m), 4.16–4.01 (1H, m), 3.67 (3H, s), 3.47 (1H, dd, J=10.6, 2.0 Hz), 2.75 (1H, ddd, J=18.6, 7.4, 1.2 Hz), 2.50–2.00 (10H, m), 2.32 (2H, t, J=7.4 Hz), 2.00–1.15 (17H, m), 0.91 (3H, t, J=6.5 Hz).

More Polar

TLC: Rf 0.38 (hexane:ethyl acetate=2:3);

NMR (CDCl$_3$): δ5.69 (1H, ddd, J=15.4, 8.0, 5.6 Hz), 5.48–5.25 (3H, m), 4.12–3.96 (1H, m), 3.67 (3H, s), 3.60–3.00 (1H, br), 3.47 (1H, dd, J=10.5, 1.7 Hz), 2.73 (1H, ddd, J=18.4, 7.4, 1.0 Hz), 2.50–1.95 (10H, m), 2.31 (2H, t, J=7.4 Hz), 1.80–1.15 (16H, m), 0.91 (3H, t, J=6.7 Hz).

Example 3(8)

(5Z,11α,13E)-18-cyclohexyl-11,16-dihydroxy-9-oxo-17,17-propano-19,20-dinorprosta-5,13-dienoic acid.methylester

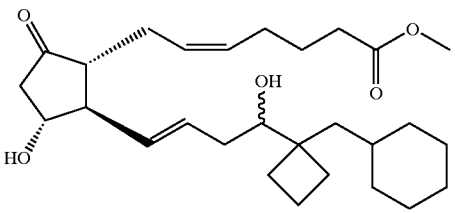

Less Polar

TLC: Rf 0.40 (hexane:ethyl acetate=2:3);

NMR (CDCl$_3$): δ5.74 (1H, ddd, J=15.2, 8.0, 6.0 Hz), 5.60–5.25 (3H, m), 4.18–4.02 (1H, m), 3.67 (3H, s), 3.67–3.56 (1H, m), 2.76 (1H, dd, J=18.2, 7.8 Hz), 2.60–1.95 (13H, m), 2.33 (2H, t, J=7.6 Hz), 1.95–1.45 (12H, m), 1.45–0.85 (7H, m).

More Polar

TLC: Rf 0.35 (hexane:ethyl acetate=2:3);

NMR (CDCl$_3$): δ5.72 (1H, ddd, J=15.4, 8.2, 5.2 Hz), 5.50–5.25 (3H, m), 4.14–3.98 (1H, m), 3.67 (3H, s), 3.61 (1H, dd, J=10.2, 2.0 Hz), 3.49 (1H, br), 2.74 (1H, ddd, J=18.4, 7.4, 1.0 Hz), 2.60–1.95 (12H, m), 2.32 (2H, t, J=7.6 Hz), 1.95–1.45 (12H, m), 1.45–0.85 (7H, m).

Example 3(9)

(5Z,11α,13E)-11,16-dihydroxy-9-oxo-17,17-propano-20-norprosta-5,13-dienoic acid.methylester

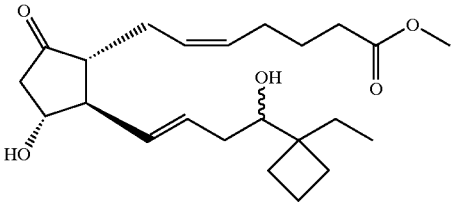

Less Polar

TLC: Rf 0.35 (hexane:ethyl acetate=1:2);

NMR (CDCl$_3$): δ5.71 (1H, ddd, J=15, 8, 6 Hz), 5.52–5.24 (3H, m), 4.15–4.03 (1H, m), 3.67 (3H, s), 3.56 (1H, dd, J=10, 2 Hz), 2.75 (1H, ddd, J=19, 7, 1 Hz), 2.50–1.35 (19H, m), 2.34 (2H, t, J=7 Hz), 0.92 (3H, t, J=7 Hz).

More Polar

TLC: Rf 0.26 (hexane:ethyl acetate=1:2);

NMR (CDCl$_3$): δ5.71 (1H, ddd, J=15, 8, 6 Hz), 5.48–5.26 (3H, m), 4.12–3.99 (1H, m), 3.66 (3H, s), 3.56 (1H, dd, J=10, 2 Hz), 2.73 (1H, ddd, J=19, 7, 1 Hz), 2.48–1.47 (19H, m), 2.34 (2H, t, J=7 Hz), 0.92 (3H, t, J=7 Hz).

Example 4

(5Z,11α,13E)-11,16-dihydroxy-9-oxo-17,17-propanoprosta-5,13-dienoic acid

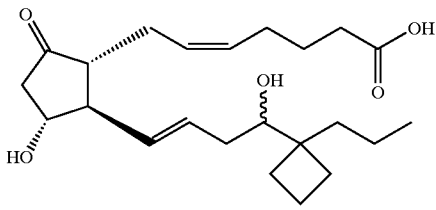

To the mixture of the less polar compound prepared in example 1 (55 mg) in ethanol (0.4 ml) and phosphate buffer (pH 7.4, 4 ml) was added PLE (pig liver esterase, 20 μl) at room temperature. The reaction mixture was stirred for 3 hours. The reaction mixture was quenched by addition of a saturated aqueous solution of ammonium sulfate, extracted with ethyl acetate. The extract was washed with 1N aqueous solution of hydrochloric acid and a saturated aqueous solution of sodium chloride, successively, dried over anhydrous magnesium sulfate and concentrated. The residue was purified by column chromatography on silica gel (hexane:ethyl acetate=1:1→ethyl acetate) to give the present invention compound (33 mg) having the following physical data. By the same procedure as provided in the above method, using the more polar compound prepared in example 1, compound (29 mg) of the present invention having the following physical data were obtained.

Less Polar
  TLC: Rf 0.41 (ethyl acetate:hexane:acetic acid=16:8:1);
  NMR (CDCl$_3$): δ5.74 (1H, dt, J=15.0, 6.0 Hz), 5.55–5.25 (3H, m), 4.08 (1H, q, J=7.5 Hz), 3.64 (1H, dd, J=10.5, 2.5 Hz), 2.75 (1H, dd, J=18.0, 7.5 Hz), 2.50–2.20 (7H, m), 2.20–1.20 (18H, m), 0.94 (3H, t, J=7.0 Hz).
More Polar
  TLC: Rf 0.36 (ethyl acetate:hexane:acetic acid=16:8:1);
  NMR (CDCl$_3$): δ5.71 (1H, ddd, J=14.0, 8.0, 6.0 Hz), 5.54–5.30 (3H, m), 4.05 (1H, q, J=8.5 Hz), 3.61 (1H, dd, J=10.0, 2.5 Hz), 2.74 (1H, dd, J=19.0, 8.0 Hz), 2.50–2.20 (7H, m), 2.20–1.20 (18H, m), 0.95 (3H, t, J=6.5 Hz).

Example 4(1)–4(13)

By the same procedure as provided in example 4, using the compound prepared in example 3–3(9), example 2 or example 1(1)–1(2), compounds of the present invention having the following physical data were obtained.

Example 4(1)

(5Z,11α,13E)-11,16-dihydroxy-20-methyl-9-oxo-17,17-propanoprosta-5,13-dienoic acid

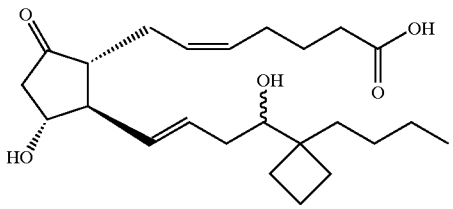

Less Polar
  TLC: Rf 0.74 (ethyl acetate:acetic acid=50:1);
  NMR (CDCl$_3$): δ5.72 (1H, dt, J=16, 7 Hz), 5.52–5.31 (3H, m), 5.10–4.50 (3H, brs), 4.14–4.01 (1H, m), 3.60 (1H, dd, J=16, 2 Hz), 2.74 (1H, dd, J=18, 7 Hz), 2.45–1.15 (25H, m), 0.90 (3H, t, J=7 Hz).
More Polar
  TLC: Rf 0.67 (ethyl acetate:acetic acid=50:1);
  NMR (CDCl$_3$): δ5.90–4.80 (7H, m), 4.10–3.98 (1H, m), 3.56 (1H, d, J=9 Hz), 2.72 (1H, dd, J=18, 7 Hz), 2.47–1.15 (23H, m), 2.30 (2H, t, J=7 Hz), 0.90 (3H, t, J=7 Hz).

Example 4(2)

(5Z,11α,13E)-11,16-dihydroxy-20-ethyl-9-oxo-17,17-propanoprosta-5,13-dienoic acid

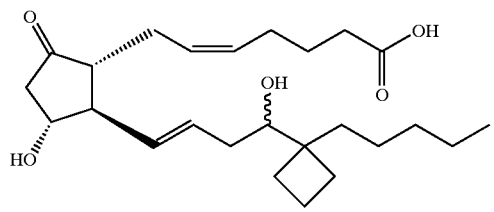

Less Polar
  TLC: Rf 0.80 (ethyl acetate:acetic acid=50:1);
  NMR (CDCl$_3$): δ5.72 (1H, dt, J=15, 7 Hz), 5.52–5.31 (3H, m), 5.60–4.40 (3H, brs), 4.14–4.01 (1H, m), 3.60 (1H, dd, J=11, 2 Hz), 2.74 (1H, dd, J=18, 8 Hz), 2.45–1.18 (25H, m), 2.34 (2H, t, J=7 Hz), 0.90 (3H, t, J=7 Hz).
More Polar
  TLC: Rf 0.73 (ethyl acetate:acetic acid=50:1);
  NMR (CDCl$_3$): δ5.76–5.61 (1H, m), 5.49–5.32 (3H, m), 4.80–4.20 (3H, brs), 4.11–3.98 (1H, m), 3.59 (1H, dd, J=10, 1Hz), 2.73 (1H, dd, J=18, 8 Hz), 2.45–1.15 (25H, m), 2.35 (2H, t, J=7 Hz), 0.90 (3H, t, J=7 Hz).

Example 4(3)

(5Z, 11α,13E)-20-chloro-11,16-dihydroxy-9-oxo-17,17-propanoprosta-5,13-dienoic acid

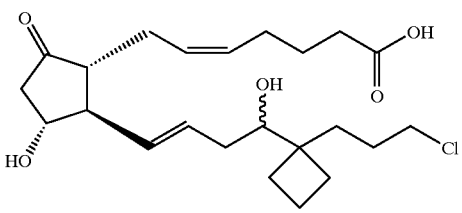

Less Polar
  TLC: Rf 0.50 (ethyl acetate:acetic acid, 50:1)
  NMR (CDCl$_3$): δ5.80–5.65 (1H, m), 5.54–5.38 (3H, m), 4.20–3.00 (3H, br), 4.17–4.02 (1H, m), 3.63 (1H, dd, J=10, 2 Hz), 3.56 (2H, t, J=6.2 Hz), 2.76 (1H, dd, J=17.8, 6.8 Hz), 2.46–1.48 (2 3H, m).
More Polar
  TLC: Rf 0.44 (ethyl acetate:acetic acid=50:1);
  NMR (CDCl$_3$): δ5.68 (1H, ddd, J=15, 7, 5 Hz), 5.50–5.29 (3H, m), 4.80–4.00 (3H, br), 4.12–3.99 (1H, m), 3.63–3.53 (3H, m), 2.74 (1H, dd, J=18, 7 Hz), 2.45–1.50 (21H, m), 2.30 (2H, t, J=7 Hz).

Example 4(4)

(5Z,11α,13E)-11,16-dihydroxy-9-oxo-18-phenyl-17,17-propano-19,20-dinorprosta-5,13-dienoic acid

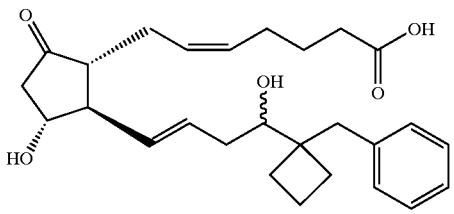

Less Polar

TLC: Rf 0.52 (ethyl acetate:acetic acid=50:1);

NMR (CDCl$_3$): δ7.37–7.18 (5H, m), 5.72 (1H, ddd, J=15, 7, 6 Hz), 5.54–5.40 (3H, m), 4.14–4.01 (1H, m), 3.67 (1H, dd, J=10, 2 Hz), 3.50–2.90 (3H, brs), 2.90 (1H, d, J=14 Hz), 2.75 (1H, dd, J=19, 8 Hz), 2.66 (1H, d, J=14 Hz), 2.47–1.45 (17H, m), 2.31 (2H, t, J=7 Hz).

More Polar

TLC: Rf 0.43 (ethyl acetate:acetic acid=50:1);

NMR (CDCl$_3$): δ7.37–7.18 (5H, m), 5.67 (1H, ddd, J=15, 8, 6 Hz), 5.49–5.28 (3H, m), 5.20–4.60 (3H, brs), 4.18–3.98 (1H, m), 3.62 (1H, brd, J=10 Hz), 2.87 (1H, d, J=14 Hz), 2.73 (1H, dd, J=18, 8 Hz), 2.65 (1H, d, J=14 Hz), 2.45–1.42 (19H, m).

Example 4(5)

(5Z,11α,13E)-11,16-dihydroxy-9-oxo-17,17-propanoprosta-5,13–19-trienoic acid

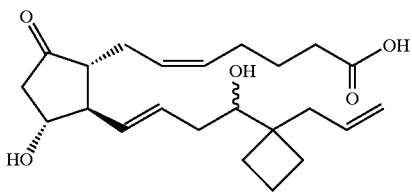

Less Polar

TLC: Rf 0.28 (hexane:ethyl acetate:acetic acid=1:2:0.03);

NMR (CDCl$_3$): δ5.94 (1H, ddt, J=17.0, 10.0, 7.4 Hz), 5.72 (1H, ddd, J=15.0, 7.8, 6.2 Hz), 5.60–5.30 (3H, m), 5.20–5.05 (2H, m), 5.00–4.00 (3H, br), 4.16–4.00 (1H, m), 3.63 (1H, dd, J=10.2, 2.4 Hz), 2.75 (1H, ddd, J=18.2, 7.4, 1.0 Hz), 2.50–1.60 (21H, m).

More Polar

TLC: Rf 0.21 (hexane:ethyl acetate:acetic acid=1:2:0.03);

NMR (CDCl$_3$): δ5.94 (1H, ddt, J=17.2, 10.2, 7.2 Hz), 5.66 (1H, ddd, J=15.2, 8.0, 5.6 Hz), 5.53–5.25 (3H, m), 5.30–4.50 (3H, br), 5.20–5.00 (2H, m), 4.12–3.96 (1H, m), 3.58 (1H, dd, J=10.2, 1.8 Hz), 2.72 (1H, dd, J=18.2, 7.2 Hz), 2.50–1.60 (21H, m).

Example 4(6)

(5Z,11α,13E)-11,16-dihydroxy-20-methyl-9-oxo-17,17-propanoprosta-5,13-diene-19-ynoic acid

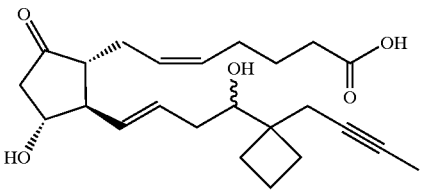

Less Polar

TLC: Rf 0.26 (hexane:ethyl acetate:acetic acid=1:2:0.03);

NMR (CDCl$_3$): δ5.84–5.66 (1H, m), 5.56–5.32 (3H, m), 4.80–3.60 (3H, br), 4.18–4.00 (1H, m), 3.77 (1H, dd, J=10.0, 2.6 Hz), 2.76 (1H, ddd, J=18.4, 7.4, 1.0 Hz), 2.50–1.60 (21H, m), 1.81 (3H, t, J=2.5 Hz).

More Polar

TLC: Rf 0.20 (hexane:ethyl acetate:acetic acid=1:2:0.03);

NMR (CDCl$_3$): δ5.71 (1H, ddd, J=15.0, 7.6, 5.8 Hz), 5.52–5.28 (3H, m), 5.30–4.20 (3H, br), 4.13–3.95 (1H, m), 3.72 (1H, dd, J=10.2, 2.2 Hz), 2.74 (1H, ddd, J=18.4, 7.4, 1.0 Hz), 2.50–1.60 (21H, m), 1.81 (3H, t, J=2.5 Hz).

Example 4(7)

(5Z,11α,13E)-17,17-butano-11,16-dihydroxy-9-oxoprosta-5,13-dienoic acid

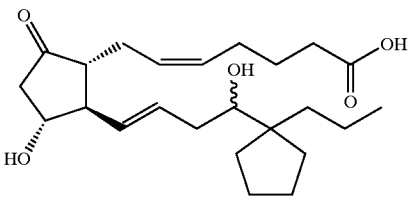

Less Polar

TLC: Rf 0.33 (hexane:ethyl acetate:acetic acid=2:3:0.05);

NMR (CDCl$_3$): δ5.82–5.65 (1H, m), 5.55–5.30 (3H, m), 5.40–4.60 (3H, br), 4.16–3.98 (1H, m), 3.55 (1H, dd, J=10.6, 2.0Hz), 2.75 (1H, dd, J=18.0, 7.0 Hz), 2.50–1.90 (11H, m), 1.80–1.10 (14H, m), 0.90 (3H, t, J=6.4 Hz).

More Polar

TLC: Rf 0.26 (hexane:ethyl acetate:acetic acid=2:3:0.05);

NMR (CDCl$_3$): δ5.75–5.57 (1H, m), 5.50–5.30 (3H, m), 5.80–4.80 (3H, br), 4.12–3.94 (1H, m), 3.51 (1H, d, J=9.4 Hz), 2.73 (1H, dd, J=18.0, 7.0 Hz), 2.50–1.95 (11H, m), 1.80–1.10 (14H, m), 0.90 (3H, t, J=6.4 Hz).

Example 4(8)

(5Z,11α,13E)-11,16-dihydroxy-9-oxo-17,17-pentanoprosta-5,13-dienoic acid

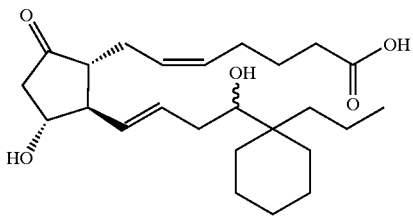

Less Polar

TLC: Rf 0.35 (hexane:ethyl acetate:acetic acid=2:3:0.05);

NMR (CDCl$_3$): δ5.81–5.63 (1H, m), 5.55–5.30 (3H, m), 5.40–4.50 (3H, br), 4.15–3.98 (1H, m), 3.53 (1H, d, J=10.2 Hz), 2.75 (1H, dd, J=18.2, 7.0 Hz) 2.50–1.90 (11H, m), 1.80–1.10 (16H, m), 0.90 (3H, t, J=6.4 Hz).

More Polar

TLC: Rf 0.28 (hexane:ethyl acetate:acetic acid=2:3:0.05);

NMR (CDCl$_3$): δ5.75–5.57 (1H, m), 5.50–5.30 (3H, m), 5.80–5.00 (3H, br), 4.11–3.95 (1H, m), 3.50 (1H, d, J=10.0 Hz), 2.73 (1H, dd, J=18.4, 7.0 Hz) 2.50–1.90 (11H, m), 1.80–1.10 (16H, m), 0.90 (3H, t, J=6.4 Hz).

Example 4(9)

(5Z,11α,13E)-18-cyclohexyl-11,16-dihydroxy-9-oxo-17,17-propano-19,20-dinorprosta-5,13-dienoic acid

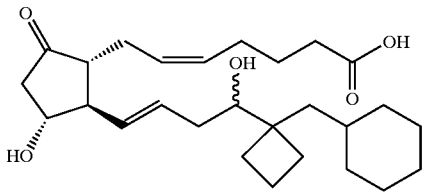

Less Polar

TLC: Rf 0.36 (hexane:ethyl acetate:acetic acid=1:2:0.03);

NMR (CDCl$_3$): δ5.75 (1H, ddd, J=15.2, 7.4, 6.0 Hz), 5.55–5.30 (3H, m), 5.40–4.40 (3H, br), 4.17–4.02 (1H, m), 3.68 (1H, dd, J=10.2, 2.2 Hz), 2.76 (1H, dd, J=18.2, 7.0 Hz), 2.50–1.90 (14H, m ), 1.90–1.40 (11H, m) 1.40–0.80 (7H, m).

More Polar

TLC: Rf 0.26 (hexane:ethyl acetate:acetic acid=1:2:0.03);

NMR (CDCl$_3$): δ5.73 (1H, ddd, J=15.0, 7.7, 6.1 Hz), 5.55–5.30 (3H, m), 4.80–3.60 (3H, br), 4.15–3.98 (1H, m), 3.66 (1H, dd, J=10.2, 2.0 Hz), 2.74 (1H, dd, J=18.2, 6.8 Hz), 2.50–1.90 (14H, m), 1.90–1.40 (11H, m) 1.40–0.80 (7H, m).

Example 4(10)

(5Z,11α,13E)-11,16-dihydroxy-9-oxo-17,17-propano-20-norprosta-5,13-dienoic acid

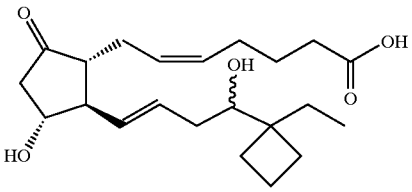

Less Polar

TLC: Rf 0.43 (ethyl acetate:acetic acid=50:1);

NMR (CDCl$_3$): δ5.73 (1H, ddd, J=16, 8, 7 Hz), 5.53–5.38 (3H, m), 4.90–4.10 (3H, brs), 4.14–4.02 (1H, m), 3.63 (1H, dd, J=10, 3 Hz), 2.75 (1H, ddd, J=19, 8, 1 Hz), 2.45–1.30 (19H, m), 2.33 (2H, t, J=7 Hz), 0.92 (3H, t, J=7 Hz).

More Polar

TLC: Rf 0.39 (ethyl acetate:acetic acid=50:1);

NMR (CDCl$_3$): δ5.71(1H, ddd, J=15, 8, 6 Hz), 5.49–5.29 (3H, m), 5.20–4.40 (3H, brs), 4.11–3.98 (1H, m), 3.60 (1H, dd, J=10, 2 Hz), 2.73 (1H, ddd, J=18, 7, 1 Hz), 2.45–1.35 (19H, m), 2.33 (2H, t, J=7 Hz), 0.92 (3H, t, J=7 Hz).

Example 4(11)

(5Z,11α,16RS)-11,16-dihydroxy-9-oxo-17,17-propanoprosta-5-enoic acid

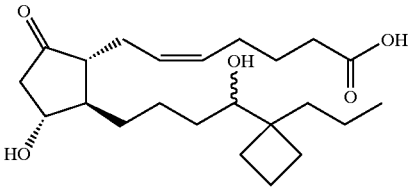

Mixture

TLC: Rf 0.62 (ethyl acetate:acetic acid=50:1);

NMR (CDCl$_3$): δ5.50–5.20 (2H, m), 5.20–4.60 (3H, brs), 4.20–4.10 (1H, m), 3.58–3.52 (1H, m), 2.75–2.61(1H, dd, J=18, 7 Hz), 2.50–1.20 (25H, m), 2.32 (2H, t, J=7 Hz), 0.92 (3H, t, J=7 Hz).

Example 4(12)

(5Z,11α,16RS)-11,16-dihydroxy-9-oxo-17,17-propanoprosta-5-ene-13-ynoic acid

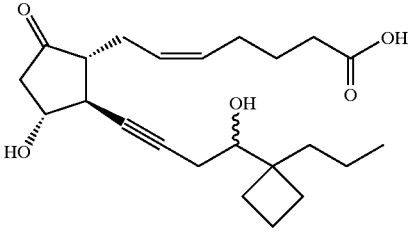

Mixture

TLC: Rf 0.45 (ethyl acetate:acetic acid=50:1);

NMR (CDCl$_3$): δ6.00–5.20 (3H, brs), 5.50–5.30 (2H, m), 4.37–4.21(1H, m), 3.75–3.65 (1H, m), 2.73 (1H, dd, J=18.2, 6.6 Hz), 2.70–1.20 (23H, m), 0.93 (3H, t, J=7.0 Hz).

Example 4(13)

(11α,13E)-11,16-dihydroxy-9-oxo-17,17-propanoprosta-13-ene-5-ynoic acid

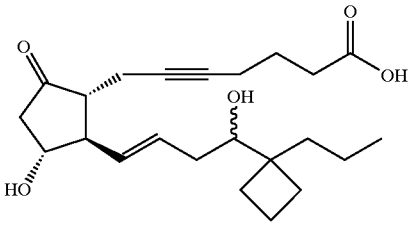

Less Polar

TLC: Rf 0.30 (hexane:ethyl acetate:acetic acid=1:3:0.04);

NMR (CDCl₃): δ5.83 (1H, dt, J=15.4, 6.8 Hz), 5.48 (1H, dd, J=15.4, 8.2 Hz), 5.50–4.50 (3H, br), 4.22–4.05 (1H, m), 3.60 (1H, dd, J=10.0, 2.4 Hz), 2.88–2.62 (3H, m), 2.49 (2H, t, J=7.1 Hz), 2.40–1.20 (19H, m), 0.94 (3H, t, J=6.7 Hz).

More Polar

TLC: Rf 0.25 (hexane:ethyl acetate:acetic acid=1:3:0.04);

NMR (CDCl₃): δ6.00–4.80 (3H, br), 5.71 (1H, ddd, J=15.0, 9.2, 4.4 Hz), 5.41(1H, dd, J=15.0, 8.5 Hz), 4.20–4.03 (1H, m), 3.61(1H, d, J=10.0 Hz), 2.88–2.65 (3H, m), 2.50 (2H, t, J=7.0 Hz), 2.40–1.20 (19H, m), 0.94 (3H, t, J=6.7 Hz).

Example 5

(5Z,11α,13E)-17,17-propano-19,20-methano-11,16-dihydroxy-9-oxoprosta-5,13-dienoic acid.methylester

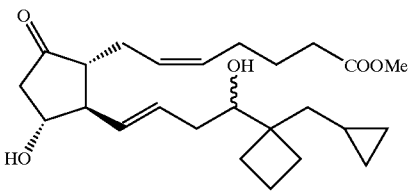

By the same procedure as provided in example 1, using the protected compound by TBS provided by the same procedure in reference example 1, reference example 2 or reference example 3, compounds of the present invention having the following physical data were obtained.

Less Polar

TLC: Rf 0.48 (hexane:ethyl acetate=1:2);

NMR (CDCl₃): δ5.73 (1H, ddd, J=15.2, 7.8, 5.8 Hz), 5.54–5.26 (3H, m), 4.17–4.01(1H, m), 3.74–3.63 (1H, m), 3.67 (3H, s), 2.75 (1H, ddd, J=18.4, 7.6 1.0 Hz), 2.50–1.60 (19H, m), 2.32 (2H, t, J=7.6 Hz), 1.54 (1H, dd, J=14.0, 6.8 Hz), 1.34 (1H, dd, J=14.0, 6.4 Hz), 0.90–0.68 (1H, m), 0.55–0.44 (2H, m), 0.16–0.05 (2H, m).

More Polar

TLC: Rf 0.38 (hexane:ethyl acetate=1:2);

NMR (CDCl₃): δ5.70 (1H, ddd, J=15.4, 8.2, 5.6 Hz), 5.50–5.25 (3H, m), 4.14–3.98 (1H, m), 3.74–3.62 (1H, m), 3.67 (3H, s), 3.34 (1H, br), 2.74 (1H, ddd, J=18.4, 7.4, 1.0 Hz), 2.50–1.60 (18H, m), 2.31(2H, t, J=7.4 Hz), 1.53 (1H, dd, J=14.0, 6.8 Hz), 1.36 (1H, dd, J=14.0, 6.4 Hz), 0.90–0.68 (1H, m), 0.56–0.45 (2H, m), 0.16–0.06 (2H, m).

Example 5(1)~5(7)

By the same procedure as provided in example 5, compounds of the present invention having the following physical data were obtained.

Example 5(1)

(5Z,11α,13E)-17,17-propano-20,20-methylene-11,16-dihydroxy-9-oxoprosta-5,13-dienoic acid.methylester

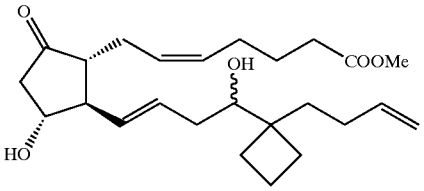

Less Polar

TLC: Rf 0.49 (hexane:ethyl acetate=1:2);

NMR (CDCl₃): δ5.86 (1H, ddt, J=17.0, 10.4, 6.5 Hz), 5.71(1H, ddd, J=15.2, 7.8, 5.8 Hz), 5.55–5.25 (3H, m), 5.10–4.90 (2H, m), 4.18–4.01(1H, m), 3.67 (3H, s), 3.57 (1H, dd, J=10.0, 2.6 Hz), 2.76 (1H, ddd, J=18.4, 7.4, 1.0 Hz), 2.50–1.40 (23H, m), 2.32 (2H, t, J=7.4 Hz).

More Polar

TLC: Rf 0.40 (hexane:ethyl acetate=1:2);

NMR (CDCl₃): δ5.86 (1H, ddt, J=17.2, 10.2, 6.4 Hz), 5.71 (1H, ddd, J=15.2, 8.0, 5.8 Hz), 5.50–5.25 (3H, m), 5.10–4.90 (2H, m), 4.14–3.98 (1H, m), 3.67 (3H, s), 3.57 (1H, dd, J=10.2, 2.4 Hz), 3.02 (1H, br), 2.74 (1H, ddd, J=18.4, 7.4, 1.0 Hz), 2.50–1.40 (22H, m), 2.32 (2H, t, J=7.5 Hz).

Example 5(2)

(5Z,11α,13E)-17,17-propano-20-methoxy-11,16-dihydroxy-9-oxoprosta-5,13-dienoic acid.methylester

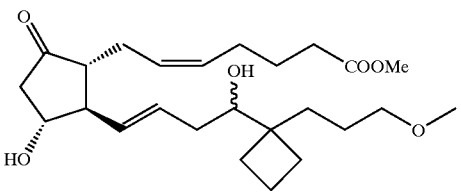

Less Polar

TLC: Rf 0.25 (hexane:ethyl acetate=1:3);

NMR (CDCl₃): δ5.71 (1H, ddd, J=15.4, 7.4, 6.4 Hz), 5.55–5.25 (3H, m), 4.16–4.00 (1H, m), 3.67 (3H, s), 3.57 (1H, dd, J=9.6, 2.6 Hz), 3.48–3.30 (2H, m) 3.35 (3H, s), 2.75 (1H, ddd, J=18.4, 8.0, 1.0 Hz), 2.70 (1H, br), 2.50–1.45 (22H, m), 2.32 (2H, t, J=7.5 Hz).

More Polar

TLC: Rf 0.17 (hexane:ethyl acetate=1:3);

NMR (CDCl₃): δ5.69 (1H, ddd, J=15.2, 8.4, 5.6 Hz), 5.50–5.25 (3H, m), 4.13–3.98 (1H, m), 3.67 (3H, s), 3.56 (1H, dd, J=10.0, 2.2 Hz), 3.46–3.32 (2H, m), 3.35 (3H, s), 2.74 (1H, ddd, J=18.4, 7.4, 1.0 Hz), 2.50–1.45 (23H, m), 2.31 (2H, t, J=7.3 Hz).

Example 5(3)

(5Z,11α,13E)-17,17-propano-20-fluoro-11,16-dihydroxy-9-oxoprosta-5,13-dienoic acid.methylester

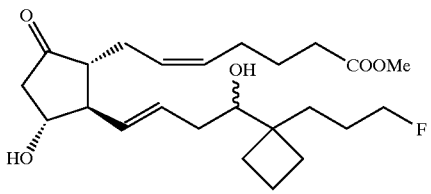

Less Polar

TLC: Rf 0.31(hexane:ethyl acetate=1:2);

NMR (CDCl$_3$): δ5.71(1H, ddd, J=15.4, 7.6, 5.8 Hz), 5.55–5.25 (3H, m), 4.47 (2H, dt, J=47.0, 5.2 Hz), 4.17–4.02 (1H, m), 3.67 (3H, s), 3.58 (1H, dd, J=10.0, 2.4 Hz), 2.76 (1H, ddd, J=18.6, 7.4, 1.2 Hz), 2.50–1.40 (23H, m), 2.32 (2H, t, J=7.3 Hz).

More Polar

TLC: Rf 0.24 (hexane:ethyl acetate=1:2);

NMR (CDCl$_3$): δ5.70 (1H, ddd, J=15.4, 8.2, 5.8 Hz), 5.52–5.25 (3H, m), 4.47 (2H, dt, J=46.8, 5.8 Hz), 4.14–3.98 (1H, m), 3.67 (3H, s), 3.58 (1H, dd, J=10.2, 2.2 Hz), 3.06 (1H, br), 2.74 (1H, ddd, J=18.4, 7.4, 1.0 Hz), 2.50–1.40 (22H, m), 2.32 (2H, J=7.5 Hz).

Example 5(4)

(5Z,11α,13E)-17,17-propano-19-methyl-11,16-dihydroxy-9-oxoprosta-5,13-dienoic acid.methylester

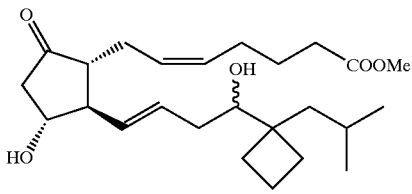

Less Polar

TLC: Rf 0.45 (hexane:ethyl acetate=1:2);

NMR (CDCl$_3$): δ5.73 (1H, ddd, J=15.2, 8.0, 6.0 Hz), 5.50–5.25 (3H, m), 4.17–4.02 (1H, m), 3.70–3.58 (1H, m), 3.67 (3H, s), 2.76 (1H, ddd, J=18.4, 7.6 1.0 Hz), 2.50–1.60 (20H, m), 2.33 (2H, t, J=7.4 Hz), 1.56 (1H, dd, J=14.2, 6.8 Hz), 1.33 (1H, dd, J=14.2, 6.2 Hz), 0.92 (6H, d, J=6.6 Hz).

More Polar

TLC: Rf 0.35 (hexane:ethyl acetate=1:2);

NMR (CDCl$_3$): δ5.72 (1H, ddd, J=15.2, 8.2, 5.8 Hz), 5.50–5.25 (3H, m), 4.14–3.98 (1H, m), 3.70–3.59 (1H, m), 3.67 (3H, s), 3.24 (1H, br), 2.74 (1H, ddd, J=18.4, 7.6, 1.0 Hz), 2.50–1.60 (19H, m), 2.32 (2H, t, J=7.4 Hz), 1.56 (1H, dd, J=14.2, 6.8 Hz), 1.34 (1H, dd, J=14.2, 6.4 Hz), 0.92 (6H, d, J=6.6 Hz).

Example 5(5)

(5Z,11α,13E)-17,17-propano-11,16-dihydroxy-9-oxo-20-norprosta-5,13,18-trienoic acid.methylester

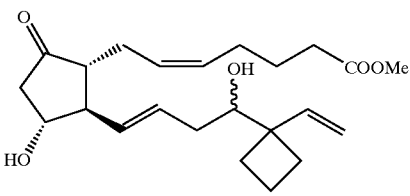

Less Polar

TLC: Rf 0.30 (hexane:ethyl acetate=1:2);

NMR (CDCl$_3$): δ5.95 (1H, dd, J=17.2, 10.7 Hz), 5.69 (1H, ddd, J=15.2, 7.6, 6.0 Hz), 5.49–5.29 (3H, m), 5.22 (1H, dd, J=10.7, 1.8 Hz), 5.15 (1H, dd, J=17.2, 1.8 Hz), 4.13–4.01 (1H, m), 3.67 (3H, s), 3.60 (1H, dd, J=10.0, 2.3 Hz), 2.74 (1H, ddd, J=18.4, 7.4, 1.2 Hz), 2.45–1.60 (19H, m), 2.30 (2H, t, J=7.0 Hz).

More Polar

TLC: Rf 0.22 (hexane:ethyl acetate=1:2);

NMR (CDCl$_3$): δ5.94 (1H, dd, J=17.0, 10.8 Hz), 5.67 (1H, ddd, J=15.2, 8.4, 5.8 Hz), 5.45–5.29 (3H, m), 5.23 (1H, dd, J=10.8, 1.6 Hz), 5.15 (1H, dd, J=17.0, 1.8 Hz), 4.13–3.97 (1H, m), 3.66 (3H, s), 3.59 (1H, dd, J=10.4, 2.2 Hz), 2.73 (1H, dd, J=18.2, 7.2 Hz), 2.44–1.60 (19H, m), 2.30 (2H, t, J=6.9 Hz).

Example 5(6)

(5Z,11α,13E)-17,17-propano-11,16-dihydroxy-9-oxo-19,20-dinorprosta-5,13-dienoic acid.methylester

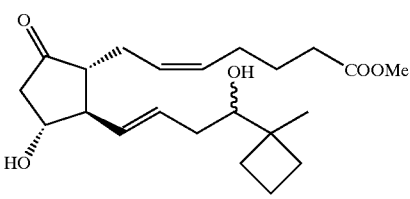

More Polar

TLC: Rf 0.30 (hexane:ethyl acetate=1:3);

NMR (CDCl$_3$): δ5.71(1H, ddd, J=15, 8, 6 Hz), 5.55–5.25 (3H, m), 4.18–4.02 (1H, m), 3.67 (3H, s), 3.56 (1H, dd, J=10, 2 Hz), 2.73 (1H, ddd, J=19, 7, 1 Hz), 2.50–1.60 (21H, m), 1.15 (3H, s).

Example 5(7)

(5Z,11α,13E)-17,17-propano-11,16-dihydroxy-9-oxo-18,19,20-trinorprosta-5,13-dienoic acid.methylester

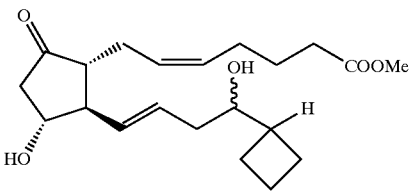

More Polar

TLC: Rf 0.25 (hexane:ethyl acetate=1:3);

NMR (CDCl₃): δ5.70 (1H, ddd, J=15, 8, 6 Hz), 5.54–5.26 (3H, m), 4.17–4.00 (1H, m), 3.66 (3H, s), 3.62–3.50 (1H, m), 2.74 (1H, ddd, J=18, 7, 1 Hz), 2.60–1.60 (22H, m).

Example 6

(5Z,11α,13E)-17,17-propano-19,20-methano-11,16-dihydroxy-9-oxoprosta-5,13-dienoic acid

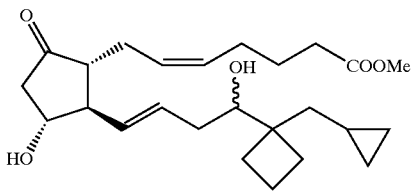

By the same procedure as provided in example 4, using each obtained the compound prepared in example 5, compounds of the present invention having the following physical data were obtained.

Less Polar

TLC: RF 0.31(hexane:ethyl acetate:acetic acid=1:2:0.03);

NMR (CDCl₃): δ5.83–5.66 (1H, m), 5.60–5.30 (3H, m), 5.40–4.20 (3H, br), 4.17–4.00 (1H, m), 3.77 (1H, dd, J=10.4, 2.2 Hz), 2.75 (1H, dd, J=18.4, 7.6 Hz), 2.50–1.60 (19H, m), 1.53 (1H, dd, J=14.2, 6.7 Hz), 1.35 (1H, dd, J=14.2, 6.4 Hz), 0.95–0.65 (1H, m), 0.60–0.45 (2H, m), 0.20–0.05 (2H, m).

More Polar

TLC: Rf 0.26 (hexane:ethyl acetate:acetic acid=1:2:0.03);

NMR (CDCl₃): δ6.00–4.00 (3H, br), 5.70 (1H, ddd, J=15.4, 7.8, 5.6 Hz), 5.50–5.25 (3H, m), 4.14–3.96 (1H, m), 3.73 (1H, dd, J=10.0, 2.0 Hz), 2.74 (1H, dd, J=18.4, 7.6 Hz), 2.50–1.60 (19H, m), 1.50 (1H, dd, J=14.2, 6.8 Hz), 1.37 (1H, dd, J=14.2, 6.3 Hz), 0.90–0.70 (1H, m), 0.60–0.45 (2H, m), 0.17–0.05 (2H, m).

Example 6(1)~6(8)

By the same procedure as provided in example 6, compounds of the present invention having the following physical data were obtained.

Example 6(1)

(5Z,11α,13E)-17,17-propano-20,20-methylene-11,16-dihydroxy-9-oxoprosta-5,13-dienoic acid

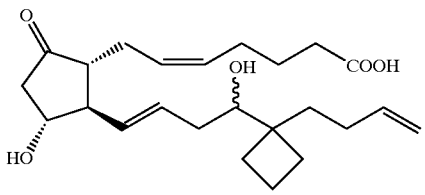

Less Polar

TLC: Rf 0.32 (hexane:ethyl acetate:acetic acid=1:2:0.03);

NMR (CDCl₃): δ5.86 (1H, ddt, J=17.0, 10.2, 6.8 Hz), 5.80–5.64 (1H, m), 5.55–5.30 (3H, m), 5.10–4.90 (2H, m), 5.00–4.00 (3H, br), 4.16–4.00 (1H, m), 3.64 (1H, dd, J=10.2, 2.4 Hz), 2.75 (1H, dd, J=18.4, 7.4 Hz), 2.50–1.40 (23H, m).

More Polar

TLC: Rf 0.27 (hexane:ethyl acetate:acetic acid=1:2:0.03);

NMR (CDCl₃): δ5.86 (1H, ddt, J=17.0, 10.2, 6.4 Hz), 5.78–5.60 (1H, m), 5.60–4.40 (3H, br), 5.55–5.25 (3H, m), 5.10–4.90 (2H, m), 4.12–3.96 (1H, m), 3.61(1H, dd, J=10.2, 1.8 Hz), 2.74 (1H, dd, J=18.6, 7.4 Hz), 2.50–1.40 (23H, m).

Example 6(2)

(5Z,11α,13E)-17,17-propano-20-methoxy-11,16-dihydroxy-9-oxoprosta-5,13-dienoic acid

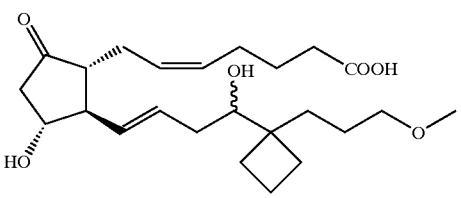

Less Polar

TLC: Rf 0.36 (ethyl acetate:acetic acid=100:1);

NMR (CDCl₃): δ5.72 (1H, dt, J=15.2, 6.6 Hz), 5.55–5.25 (3H, m), 5.60–4.40 (3H, br), 4.16–4.00 (1H, m), 3.61 (1H, dd, J=9.6, 2.2 Hz), 3.48–3.38 (2H, m), 3.37 (3H, s), 2.75 (1H, dd, J=18.2, 7.4 Hz), 2.50–1.40 (23H, m).

More Polar

TLC: Rf 0.27 (ethyl acetate:acetic acid=100:1);

NMR (CDCl₃): δ5.68 (1H, ddd, J=15.2, 8.0, 5.0 Hz), 5.50–5.20 (3H, m), 5.40–4.20 (3H, br), 4.13–3.97 (1H, m), 3.56 (1H, dd, J=10.4, 2.0 Hz), 3.55–3.55 (2H, m), 3.38 (3H, s), 2.75 (1H, dd, J=18.2, 7.4 Hz), 2.50–1.40 (23H, m).

Example 6(3)

(5Z,11α,13E)-17,17-propano-20-fluoro-11,16-dihydroxy-9-oxoprosta-5,13-dienoic acid

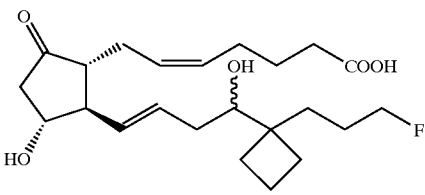

Less Polar

TLC: Rf 0.30 (hexane:ethyl acetate:acetic acid=1:3:0.04);

NMR (CDCl₃): δ5.72 (1H, ddd, J=15.5, 7.0, 6.0 Hz), 5.48 (1H, dd, J=15.5, 8.5 Hz), 5.46–5.36 (2H, m), 5.20–3.80 (3H, br), 4.55–4.48 and 4.46–4.38 (2H, m), 4.12–4.04 (1H, m), 3.64 (1H, dd, J=10.5, 2.0 Hz), 2.75 (1H, ddd, J=18.5, 7.5, 1.0 Hz), 2.43–2.26 (6H, m), 2.21 (1H, dd, J=18.5, 10.0 Hz), 2.15–1.95 (6H, m), 1.95–1.63 (9H, m), 1.57–1.48 (1H, m).

More Polar

TLC: Rf 0.23 (hexane:ethyl acetate:acetic acid=1:3:0.04);

NMR (CDCl₃): δ5.68 (1H, ddd, J=15.5, 8.0, 5.5 Hz), 5.46 (1H, dd, J=15.5, 8.5 Hz), 5.50–4.50 (3H, br), 5.45–5.33 (2H, m), 4.55–4.48 and 4.46–4.38 (2H, m), 4.10–4.02 (1H, m), 3.61 (1H, dd, J=10.5, 2.0 Hz), 2.73 (1H, dd, J=18.0, 7.0 Hz), 2.43–2.25 (6H, m), 2.20 (1H, dd, J=18.0, 10.0 Hz), 2.15–1.95 (6H, m), 1.95–1.62 (9H, m), 1.57–1.48 (1H, m).

Example 6(4)

(5Z,11α,13E)-17,17-propano-19-methyl-11,16-dihydroxy-9-oxoprosta-5,13-dienoic acid

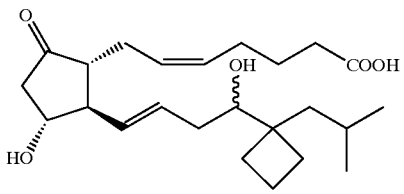

Less Polar

TLC: Rf 0.31(hexane:ethyl acetate:acetic acid=1:2:0.03);

NMR (CDCl$_3$): δ5.75 (1H, dt, J=15.2, 6.4 Hz), 5.55–5.30 (3H, m), 5.40–4.40 (3H, br), 4.17–4.00 (1H, m), 3.70 (1H, dd, J=10.2, 2.0 Hz), 2.76 (1H, ddd, J=18.6, 7.4, 1.0 Hz), 2.50–1.50 (20H, m), 1.55 (1H, dd, J=14.2, 6.8 Hz), 1.33 (1H, dd, J=14.2, 6.2 Hz), 0.92 (6H, d, J=6.6 Hz).

More Polar

TLC: Rf 0.24 (hexane:ethyl acetate:acetic acid=1:2:0.03);

NMR (CDCl$_3$): δ5.72 (1H, ddd, J=15.2, 8.0, 5.8 Hz), 5.55–5.25 (3H, m), 5.20–4.20 (3H, br), 4.14–3.98 (1H, m), 3.68 (1H, dd, J=10.0, 2.0 Hz), 2.74 (1H, ddd, J=18.0, 7.2, 1.0 Hz), 2.50–1.50 (20H, m), 1.55 (1H, dd, J=14.2, 7.2 Hz), 1.33 (1H, dd, J=14.2, 6.4 Hz), 0.92 (6H, d, J=6.4 Hz).

Example 6(5)

(5Z,11α,13E)-17,17-propano-11,16-dihydroxy-9-oxo-20-norprosta-5,13,18-trienoic acid

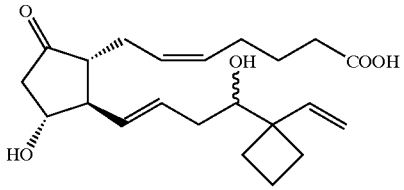

Less Polar

TLC: Rf 0.36 (ethyl acetate:acetic acid=50:1);

NMR (CDCl$_3$): δ5.93 (1H, dd, J=17.2, 10.6 Hz), 5.70 (1H, ddd, J=15.2, 7.2, 5.8 Hz), 5.49–5.38 (3H, m), 5.24 (1H, dd, J=10.6, 1.4 Hz), 5.16 (1H, dd, J=17.2, 1.4 Hz), 4.20–3.20 (3H, br), 4.13–4.00 (1H, m), 3.68 (1H, dd, J=10.4, 2.4 Hz), 2.74 (1H, ddd, J=18.4, 7.4, 1.2 Hz), 2.43–1.60 (19H, m).

More Polar

TLC: Rf 0.32 (ethyl acetate:acetic acid=50:1);

NMR (CDCl$_3$): δ5.93 (1H, dd, J=17.2, 10.6 Hz), 5.65 (1H, ddd, J=15.2, 8.2, 5.6 Hz), 5.28–5.15 (3H, m), 5.25 (1H, dd, J=10.6, 1.4 Hz), 5.16 (1H, dd, J=17.2, 1.4 Hz), 5.10–4.10 (3H, br), 4.08–3.95 (1H, m), 3.63 (1H, dd, J=10.6, 2.0 Hz), 2.70 (1H, ddd, J=19.2, 7.6, 1.1 Hz), 2.42–1.60 (19H, m).

Example 6(6)

(5Z,11α,13Z)-17,17-propano-11,16-dihydroxy-9-oxoprosta-5,13-dienoic acid

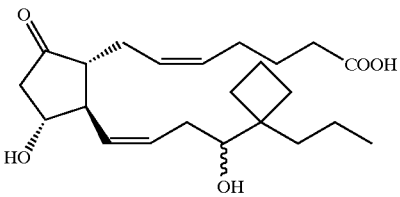

Less Polar

TLC: Rf 0.49 (hexane:ethyl acetate:acetic acid=1:2:0.03);

NMR (CDCl$_3$): δ6.00–4.00 (3H, br), 5.67 (1H, dt, J=5, 11 Hz), 5.46 (1H, t, J=11 Hz), 5.43–5.33 (2H, m), 4.08–4.00 (1H, m), 3.61 (1H, dd, J=10, 2 Hz), 2.83–2.72 (2H, m), 2.40–2.25 (3H, m), 2.33 (2H, t, J=7.5 Hz), 2.25 (1H, dd, J=19, 9.5 Hz), 2.15–2.03 (4H, m), 2.03–1.63 (8H, m), 1.60–1.53 (1H, m), 1.43–1.25 (3H, m), 0.95 (3H, t, J=7 Hz).

More Polar

TLC: Rf 0.45 (hexane:ethyl acetate:acetic acid=1:2:0.03);

NMR (CDCl$_3$): δ5.69 (1H, dt, J=11, 8 Hz), 5.47–5.35 (3H, m), 5.00–3.00 (3H, br), 4.10–4.03 (1H, m), 3.64 (1H, dd, J=7, 3 Hz), 2.84–2.73 (2H, m), 2.43–1.95 (9H, m), 2.33 (2H, t, J=7 Hz), 2.26 (1H, dd, J=18.5, 9.5 Hz), 1.92–1.55 (7H, m), 1.45–1.30 (3H, m), 0.95 (3H, t, J=7 Hz).

Example 6 (7)

(5Z,11α,13E)-17,17-propano-11,16-dihydroxy-9-oxo-19,20-dinorprosta-5,13-dienoic acid

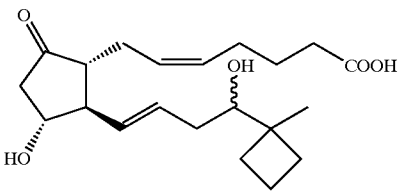

More Polar

TLC: Rf 0.19 (hexane:ethyl acetate:acetic acid=1:3:0.04);

NMR (CDCl$_3$): δ6.00–4.00 (3H, br), 5.71 (1H, ddd, J=15, 8, 6 Hz), 5.55–5.30 (3H, m), 4.15–3.95 (1H, m), 3.60 (1H, dd, J=10, 2 Hz), 2.73 (1H, ddd, J=18, 7, 1 Hz), 2.50–1.60 (19H, m), 1.15 (3H, s).

Example 6(8)

(5Z,11α,13E)-17,17-propano-11,16-dihydroxy-9-oxo-18,19,20-trinorprosta-5,13-dienoic acid

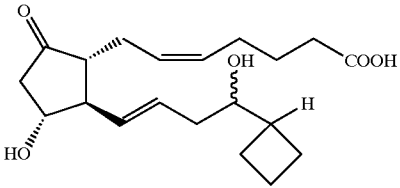

More Polar

TLC: Rf 0.16 (hexane:ethyl acetate:acetic acid=1:3:0.04);

NMR (CDCl$_3$): δ6.00–4.00 (3H, br), 5.70 (1H, ddd, J=15, 8, 6 Hz), 5.53–5.28 (3H, m), 4.13–3.96 (1H, m), 3.65–3.55 (1H, m), 2.74 (1H, ddd, J=18, 7, 1 Hz), 2.60–1.60 (20H, m).

Reference Example 12

(5Z,13E)-17,17-propano-16-hydroxy-9-oxoprosta-5,10,13-trienoic acid.methylester

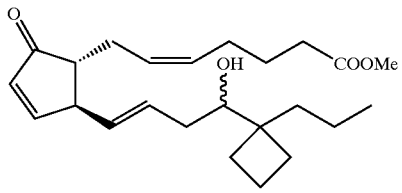

To a solution of the compound prepared in example 1 (more polar; 95 mg) in THF (5 ml) was added copper chloride (40 mg) and 1N aqueous solution of hydrochloric acid (5 ml). The reaction mixture was stirred at 60° C. for 4 hours. The reaction mixture was quenched by addition of a saturated aqueous solution of sodium hydrogencarbonate, extracted with ethyl acetate. The extract was washed with a saturated aqueous solution of sodium chloride, dried over anhydrous magnesium sulfate and concentrated. To the residue was dissolved into diethyl ether (5 ml) was added a solution of diazomethane in diethyl ether until the reaction solution became yellow color. The reaction mixture was concentrated with under reduced pressure. The residue was purified by column chromatography on silica gel (hexane-ethyl acetate) to give the tittle compound (65 mg) having the following physical data.

TLC: Rf 0.68 (hexane:ethyl acetate=1:1).

NMR (CDCl$_3$): δ7.49 (1H, dd, J=6.0, 2.8 Hz), 6.16 (1H, dd, J=6.0, 2.2 Hz), 5.67–5.24 (4H, m), 3.67 (3H, s), 3.54 (1H, dd, J=9.8, 2.8 Hz), 3.25–3.19 (1H, m), 2.30–1.25 (20H, m), 2.32 (2H, t, J=6.8 Hz), 0.92 (3H, t, J=7.0 Hz).

Reference Example 13

(5Z,13E)-17,17-propano-16-t-butyldimethylsilyloxy-9-oxoprosta-5,10,13-trienoic acid.methylester

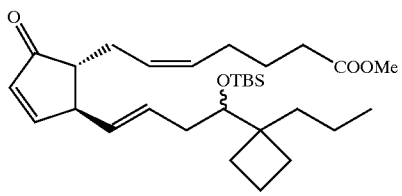

To a solution of the compound prepared in reference example 12 (60 mg) and 2,6-lutidine (116 μl) in anhydrous dichloromethane (5 ml) was added dropwise trifluoromethanesulfonic acid t-butyldimethylsilylester (190 μl) at 0° C. under an atmosphere of argon. The reaction mixture was stirred at 0° C. for 2 hours. The reaction mixture was quenched by addition of a saturated aqueous solution of sodium hydrogencarbonate, extracted with hexane (×2). The extract was washed with a saturated aqueous solution of sodium chloride, dried over anhydrous magnesium sulfate and concentrated. The residue was purified by column chromatography on silica gel (hexane-ethyl acetate) to give the title compound (44 mg) having the following physical data.

TLC: Rf 0.53 (hexane:ethyl acetate=4:1).

Reference Example 14

(5Z,13E)-17,17-propano-16-t-butyldimethylsilyloxy-9-oxoprosta-5,13-dienoic acid.methylester

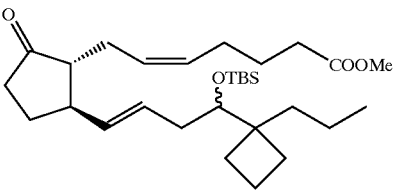

To a suspension of lithium aluminum hydride (48 mg) in anhydrous THF (1ml) was added a suspension of copper iodide (I) (190 mg) in THF-HMPA (1:1, 2 ml) at −78° C. under an atmosphere of argon. The mixture was stirred at same temperature for 30 min. To the mixture was added dropwise a solution of the compound prepared in reference example 13 (43 mg) in anhydrous THF (2 ml). The reaction mixture was stirred at same temperature for 30 min. To the reaction mixture was added a saturated aqueous solution of sodium ammonium, warmed up at room temperature, filtered. The precipitate was washed with ether. The water layer of the filtrate was extracted with ether. The extract was washed with a saturated aqueous solution of sodium chloride, dried over anhydrous magnesium sulfate and concentrated. The residue was purified by column chromatography on silica gel (hexane-ethyl acetate) to give the title compound (25 mg) having the following physical data.

Rf 0.41 (hexane:ethyl acetate=4:1);

NMR (CDCl$_3$): δ5.60–5.25 (4H, m), 3.66 (3H, s), 3.57 (1H, m), 2.50–1.20 (24H, m), 2.30 (2H, t, J=6.8 Hz), 0.98–0.85 (12H, m), 0.03 (6H, s).

Example 7

(5Z,13E)-17,17-propano-16-hydroxy-9-oxoprosta-5,13-dienoic acid.methylester

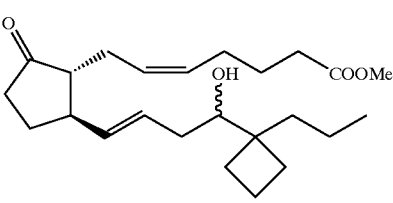

By the same procedure as provided in example 1, using the compound prepared in reference example 14, compounds of the present invention having the following physical data were obtained.

Less Polar

TLC: Rf 0.81 (hexane:ethyl acetate=1:1);

NMR (CDCl$_3$): δ5.58–5.33 (4H, m), 3.67 (3H, s), 3.51 (1H, dd, j=10.2, 2.6 Hz), 2.56–1.24 (25H, m), 2.33 (2H, t, J=7.6 Hz), 0.94 (3H, t, J=7.0 Hz).

More Polar

TLC: Rf 0.76(hexane:ethyl acetate=1:1);

NMR (CDCl$_3$): δ5.70–5.25 (4H, m), 3.67 (3H, s), 3.53 (1H, dd, J=10.0, 2.4 Hz), 2.58–1.22 (25H, m), 2.32 (2H, t, J=7.6 Hz), 0.94 (3H, t, J=6.8 Hz).

Example 8

(5Z,13E)-17,17-propano-16-hydroxy-9-oxoprosta-5,13-dienoic acid

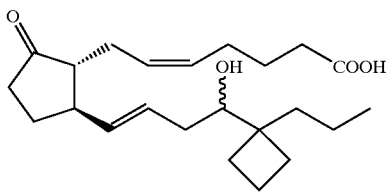

By the same procedure as provided in example 4, using the compound prepared in example 7, compounds of the present invention having the following physical data were obtained.

Less Polar

TLC: Rf 0.74 (hexane:ethyl acetate:acetic acid= 100:100:1);

NMR (CDCl$_3$): δ5.58–5.37 (4H, m), 5.40–3.40 (2H, br), 3.60 (1H, dd, J=10.2, 2.2 Hz), 2.53–1.20 (24H, m), 2.30 (2H, t, J=6.8 Hz), 0.93 (3H, t, J=6.8 Hz).

More Polar

TLC: Rf 0.71 (hexane:ethyl acetate:acetic acid= 100:100:1);

NMR (CDCl$_3$): δ5.62–5.37 (4H, m), 5.60–3.20 (2H, br), 3.64–3.53 (1H, m), 2.55–1.20 (24H, m), 2.30 (2H, t, J=6.8 Hz), 0.94 (3H, t, J=6.8 Hz).

Example 9

(5Z,11α,13E)-17,17-propano-11-methoxy-16-hydroxy-9-oxoprosta-5,13-dienoic acid.methylester

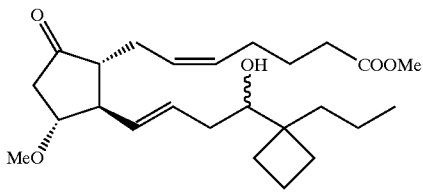

To a solution of the compound prepared in example 1 (more polar; 78 mg) in ether (5 ml) was added silica gel (kiesel gel) (4.7 g). To the mixture was added dropwise a solution of diazomethane in ether under cooling with ice. The suspension was concentrated under reduced pressure. The residue was purified by column chromatography on silica gel (kiesel gel 7734, 20 g, hexane:ethyl acetate= 5:1→3:1) to give the present invention compound (more polar: 45 mg) having the following physical data.

More Polar

Rf 0.57 (hexane:ethyl acetate=1:1);

NMR (CDCl$_3$): δ5.67 (1H, ddd, J=15.4, 7.6, 5.8 Hz), 5.51 (1H, dd, J=15.4, 7.8 Hz), 5.50–5.26 (2H, m), 3.77–3.63 (1H, m), 3.67 (3H, s), 3.53 (1H, dd, J=10.2, 2.4 Hz), 3.37 (3H, s), 2.76 (1H, ddd, J=18.6, 7.2, 1.2 Hz), 2.54 (1H, dt, J=11.8, 7.8 Hz), 2.45–1.20 (21H, m), 2.31 (2H, t, J=7.5 Hz), 0.94 (3H, t, J=6.9 Hz).

By the same reaction as provided in above method, using the less polar compound prepared in example 1, compound (less polar: 47 mg) of the present invention having the following physical data was obtained.

Less Polar

Rf 0.66 (hexane:ethyl acetate=1:1);

NMR (CDCl$_3$): δ5.74–5.26 (4H, m), 3.78–3.65 (1H, m), 3.67 (3H, s), 3.54 (1H, dd, J=10.0, 2.4 Hz), 3.38 (3H, s), 2.77 (1H, ddd, J=18.4, 7.0, 1.0 Hz), 2.55 (1H, dt, J=11.6, 7.4 Hz), 2.40–1.20 (21H, m), 2.32 (2H, t, J=7.4 Hz), 0.94 (3H, t, J=6.9 Hz).

Example 9(1)–9(4)

By the same procedure as provided in example 9, compounds of the present invention having the following physical data were obtained.

Example 9(1)

(5Z,11α,13E)-17,17-propano-11-methoxy-16-hydroxy-9-oxo-19-methylprosta-5,13-dienoic acid.methylester

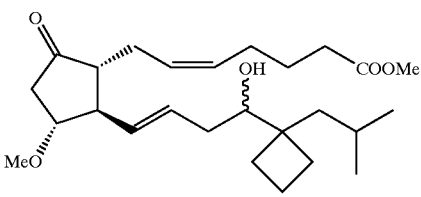

More Polar

TLC: Rf 0.72 (hexane:ethyl acetate=1:1);

NMR (CDCl$_3$): δ5.79–5.25 (4H, m), 3.77–3.60 (2H, m), 3.66 (3H, S), 3.37 (3H, s), 2.76 (1H, ddd, J=18.4, 7.6, 1.2 Hz), 2.61–1.20 (21H, m), 2.33 (2H, t, J=6.9 Hz), 0.93 (3H, d, J=1.0 Hz), 0.90 (3H, d, J=1.0 Hz).

Example 9(2)

(5Z,11α,13E)-17,17-propano-11-methoxy-16-hydroxy-9-oxo-19,20-methanoprosta-5,13-dienoic acid.methylester

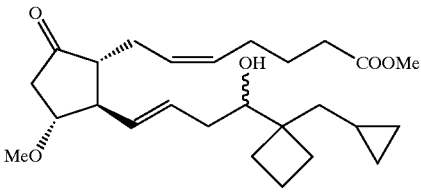

More Polar

TLC: Rf 0.63 (hexane:ethyl acetate=1:1);

NMR (CDCl$_3$): δ5.77–5.23 (4H, m), 3.76–3.64 (2H, m), 3.66 (3H, S), 3.37 (3H, s), 2.76 (1H, ddd, J=18.4, 7.0, 1.2 Hz), 2.61–1.23 (20H, m), 2.33 (2H, t, J=6.9 Hz), 0.90–0.70 (1H, m), 0.55–0.45 (2H, m), 0.15–0.05 (2H, m).

Example 9(3)

(5Z,11α,13E)-17,17-propano-11-methoxy-16-hydroxy-9-oxo-20-norprosta-5,13-dienoic acid.methylester

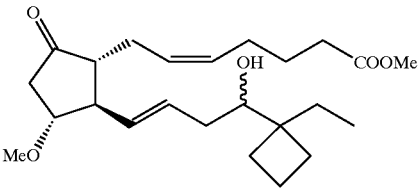

More Polar

TLC: Rf 0.56 (hexane:ethyl acetate=1:1);

NMR (CDCl$_3$): δ5.75–5.27 (4H, m), 3.76–3.64 (1H, m), 3.66 (3H, s), 3.54 (1H, dd, J=10.0, 2.4 Hz), 3.37 (3H, s), 2.76 (1H, ddd, J=18.4, 7.0, 1.2 Hz), 2.60–1.35 (20H, m), 2.31 (2H, t, J=6.8 Hz), 0.92 (3H, t, J=7.2 Hz).

Example 9(4)

(5Z,11α,13E)-17,17-propano-11-methoxy-16-hydroxy-9-oxoprosta-5,13,19-trienoic acid.methylester

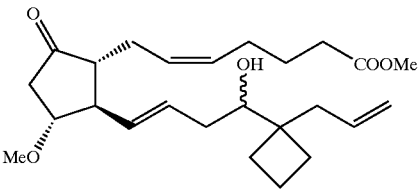

More Polar

TLC: Rf 0.53 (hexane:ethyl acetate=1:1);

NMR (CDCl$_3$): δ6.03–5.81 (1H, m), 5.75–5.23 (4H, m), 5.15–5.06 (2H, m), 3.76–3.64 (1H, m), 3.54 (1H, dd, J=10.4, 2.2 Hz), 3.37 (3H, s), 2.76 (1H, ddd, J=18.4, 7.0, 1.4 Hz), 2.60–1.50 (20H, m), 2.31 (2H, t, J=6.9 Hz).

Example 10

(5Z,11α,13E)-17,17-propano-11-methoxy-16-hydroxy-9-oxoprosta-5,13-dienoic acid

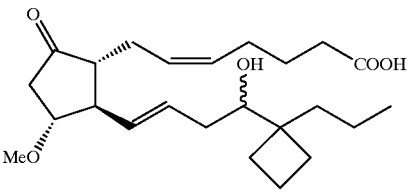

By the same procedure as provided in example 4, using the compound prepared in example 9 (less polar or more polar), compounds of the present invention having the following physical data were obtained.

Less Polar

TLC: Rf 0.40 (hexane:ethyl acetate:methanol=1:1:0.02);

NMR (CDCl$_3$): δ5.66 (1H, ddd, J=15.4, 7.6, 5.4 Hz), 5.50 (1H, dd, J=15.4, 7.2 Hz), 5.50–5.30 (2H, m), 4.50–2.50 (2H, br), 3.78–3.63 (1H, m), 3.63 (1H, dd, J=10.4, 2.4 Hz), 3.38 (3H, s), 2.77 (1H, ddd, J=18.2, 7.0, 1.0 Hz), 2.51 (1H, dt, J=11.4, 7.8 Hz), 2.40–1.20 (20H, m), 2.34 (2H, t, J=6.8 Hz), 0.94 (3H, t, J=6.7 Hz).

More Polar

TLC: Rf 0.36 (hexane:ethyl acetate:methanol=1:1:0.02);

NMR (CDCl$_3$): δ5.69 (1H, ddd, J=15.4, 6.6, 6.0 Hz), 5.54 (1H, dd, J=15.4, 7.2 Hz), 5.50–5.30 (2H, m), 5.00–3.00 (2H, br), 3.77–3.63 (1H, m), 3.60 (1H, dd, J=10.0, 2.4 Hz), 3.37 (3H, s), 2.77 (1H, ddd, J=18.2, 7.2, 1.2 Hz), 2.53 (1H, dt, J=11.2, 7.8 Hz), 2.42–1.20 (20H, m), 2.34 (2H, t, J=7.1 Hz), 0.94 (3H, t, J=6.8 Hz).

Example 10(1)~10(4)

By the same procedure as provided in example 10, compounds of the present invention having the following physical data were obtained.

Example 10(1)

(5Z,11α,13E)-17,17-propano-11-methoxy-16-hydroxy-19-methyl-9-oxoprosta-5,13-dienoic acid

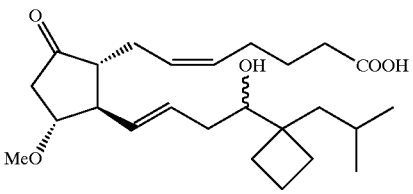

More Polar

TLC: Rf 0.28 (hexane:ethyl acetate=1:1);

NMR (CDCl$_3$): δ5 5.78–5.28 (4H, m), 5.00–4.00 (2H, br), 3.77–3.64 (2H, m), 3.37 (3H, s), 2.77 (1H, dd, J=18.4, 7.4 Hz), 2.60–1.22 (20H, m), 2.34 (2H, t, J=6.9 Hz), 0.93 (3H, d, J=1.2 Hz), 0.90 (3H, d, J=1.0 Hz).

Example 10(2)

(5Z,11α,13E)-17,17-propano-11-methoxy-16-hydroxy-9-oxo-19,20-methanoprosta-5,13-dienoic acid

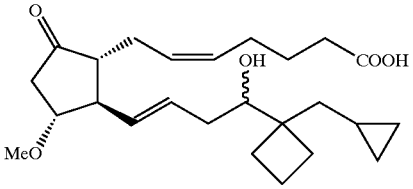

More Polar

TLC: Rf 0.29 (hexane:ethyl acetate 1:1);

NMR (CDCl$_3$): δ5.80–5.30 (4H, m), 3.79–3.64 (2H, m), 3.38 (3H, s), 2.77 (1H, dd, J=18.2, 7.2 Hz), 2.59–1.10 (23H, m), 0.95–0.70 (1H, m), 0.55–0.45 (2H, m), 0.15–0.05 (2H, m).

Example 10(3)

(5Z,11α,13E)-17,17-propano-11-methoxy-16-hydroxy-9-oxo-20-norprosta-5,13-dienoic acid

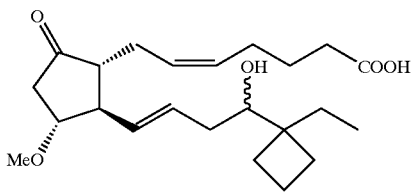

More Polar

TLC: Rf 0.27 (hexane:ethyl acetate 1:1);
NMR (CDCl₃): δ5.78–5.30 (4H, m), 3.76–3.58 (2H, m), 3.60–2.60 (2H, br), 3.37 (3H, s), 2.77 (1H, ddd, J=18.4, 7.0, 1.4 Hz), 2.60–1.32 (19H, m), 2.33 (2H, t, J=7.0 Hz), 0.92 (3H, t, J=7.4 Hz).

Example 10(4)

(5Z,11α,13E)-17,17-propano-11-methoxy-16-hydroxy-9-oxoprosta-5,13,19-trienoic acid

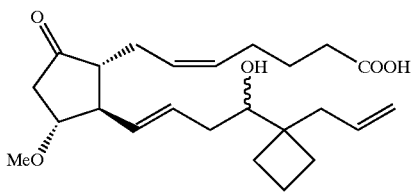

More Polar

TLC: Rf 0.25 (hexane:ethyl acetate=1:1);
NMR (CDCl₃): δ6.03–5.82 (1H, m), 5.77–5.30 (4H, m), 5.17–5.07 (2H, m), 4.40–1.40 (2H, br), 3.76–3.59 (2H, m), 3.37 (3H, s), 2.77 (1H, ddd, J=18.4, 7.2, 1.2 Hz), 2.59–1.60 (19H, m), 2.33 (2H, t, J=7.0 Hz).

Reference Example 15

(5Z,11α,13E)-17,17-propano-11,16-bis(t-butyldimethylsilyloxy)-9,9-methyleneprosta-5,13-dienoic acid.methylester

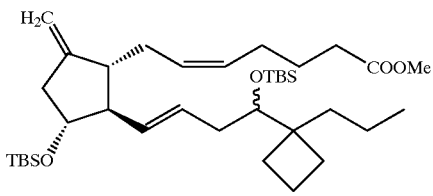

To a stirred suspension of zinc powder (2.875 g) in THF (25 ml) was added dropwise dibromomethane (1.01 ml) at room temperature under an atmosphere of argon. After the reaction mixture cooled at −40° C., to the mixture was slowly added dropwise titanium tetrachloride (1.13 ml). The mixture was stirred at 5° C. for 3 days, Nozaki-Lombardo reagent was obtained as a grayish suspension.

To a stirred solution of the compound prepared in reference example 3 (150 mg) in dichloromethane (3 ml) was added the aboved obtained Nozaki-Lombardo reagent (3 ml) at 0° C. The reaction mixture was stirred at room temperature for 1.5 hours. The reaction mixture was quenched by addition of ice and a saturated aqueous solution of sodium hydrogencarbonate, extracted with ether (×3). The extract was washed with water (×2), a saturated aqueous solution of sodium chloride, successively, dried over anhydrous magnesium sulfate and concentrated. The residue was purified by column chromatography on silica gel (Merck Kiesel gel 7734, 20 ml, ethyl acetate:hexane=1:40) to give the tittle compound (120 mg) as a colorless oil having the following physical data.

TLC: Rf 0.47 (ethyl acetate:hexane=1:20);
NMR (CDCl₃): δ5.65–5.15 (4H, m), 4.88 (1H, brs), 4.83 (1H, brs), 3.77 (1H, q, J=7.5 Hz), 3.66 (3H, s), 3.56 (1H, t, J=5.0 Hz), 2.60 (1H, dd, J=16.5, 7.0 Hz), 2.40–1.15 (23H, m), 0.90 (9H, s), 0.87 (9H, s), 1.00–0.80 (3H, m), 0.05 (6H, s), 0.02 (6H, s).

Example 11

(5Z,11α,13E)-17,17-propano-11,16-dihydroxy-9,9-methyleneprosta-5,13-dienoic acid.methylester

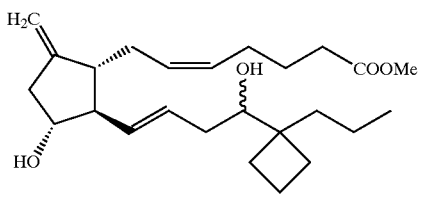

By the same procedure as provided in example 1, using the compound prepared in reference example 15, compounds of the present invention having the following physical data were obtained.

Less Polar

TLC: Rf 0.39 (ethyl acetate:hexane=1:2);
NMR (CDCl₃): δ5.70–5.30 (4H, m), 4.96 (1H, brs), 4.88 (1H, brs), 3.83 (1H, q, J=7.5 Hz), 3.67 (3H, s), 3.52 (1H, dd, J=10.0, 2.0 Hz), 2.76 (1H, dd, J=16.0, 7.0 Hz), 2.40–1.20 (25H, m), 0.93 (3H, t, J=7.0 Hz).

More Polar

TLC: Rf 0.33 (ethyl acetate:hexane=1:2);
NMR (CDCl₃): δ5.70–5.30 (4H, m), 4.95 (1H, brs), 4.88 (1H, brs), 3.82 (1H, q, J=7.0 Hz), 3.70 (3H, s), 3.53 (1H, dd, J=10.0, 2.5 Hz), 2.75 (1H, dd, J=16.0, 7.0 Hz), 2.40–1.20 (25H, m), 0.94 (3H, t, J=7.0 Hz).

Example 12

(5Z,11α,13E)-17,17-propano-11,16-dihydroxy-9,9-methyleneprosta-5,13-dienoic acid

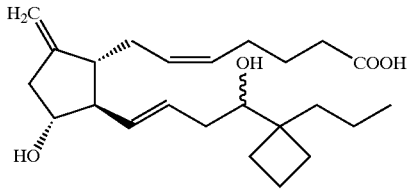

By the same procedure as provided in example 4, using the compound prepared in example 11, compounds of the present invention having the following physical data were obtained.

Less Polar

TLC: Rf 0.52 (ethyl acetate:hexane:acetic acid=9:10:1);

NMR (CDCl$_3$): δ5.70–5.30 (4H, m), 4.96 (1H, brs), 4.89 (1H, brs), 3.82 (1H, q, J=8.5 Hz), 3.61 (1H, dd, J=10, 2.5 Hz), 2.74 (1H, dd, J=15.5, 7.0 Hz), 2.40–1.20 (25H, m), 0.93 (3H, t, J=7.0 Hz).

More Polar

TLC: Rf 0.52 (ethyl acetate:hexane:acetic acid=9:10:1);

NMR (CDCl$_3$): δ5.70–5.20 (4H, m), 4.95 (1H, brs), 4.88 (1H, brs), 3.81 (1H, q, J=6.5 Hz), 3.59 (1H, dd, J=10, 2.5 Hz), 2.73 (1H, dd, J=16.0, 7.0 Hz), 2.40–1.20 (25H, m), 0.94 (3H, t, J=7.0 Hz).

Example 13

(5Z,11α,13E)-17,17-propano-11,16-dihydroxy-9-oxoprosta-5,13-dienoic acid amide

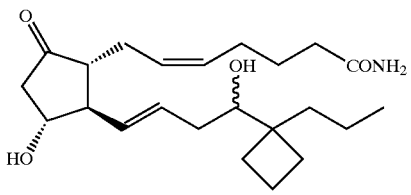

To a stirred solution of the compound prepared in example 4 (less polar; 42 mg) in dichloromethane (1 ml) was added triethylamine (81 ml) and isobutyl chloroformate (60 ml) at 0° C. After the mixture was stirred for 30 min, to the mixture was added ammonia in water solution (0.5 ml). The reaction mixture was stirred for 10 min. The reaction mixture was quenched by addition of 1N aqueous solution of hydrochloric acid, extracted with ethyl acetate (×3). The extract was washed with water (×2), 1N aqueous solution of hydrochloric acid (×2) and a saturated aqueous solution of sodium chloride, successively, dried over anhydrous magnesium sulfate and concentrated. The residue was purified by column chromatography on silica gel (Merck Kiesel gel 7734, 5 ml, ethyl acetate:hexane=3:2→MeOH:CHCl$_3$=1:19→1:9) to give the present invention compound (32 mg) as a pale yellow oil having the following physical data.

Less Polar

TLC: Rf 0.52 (methanol:chloroform=1:9);

NMR (CDCl$_3$): δ5.90–5.20 (6H, m), 4.10 (1H, q, J=9.0 Hz), 3.55 (1H, d, J=8.0 Hz), 2.73 (1H, dd, J=11.0, 7.5 Hz), 2.75–2.55 (1H, m), 2.55–1.20 (24H, m), 0.94 (3H, t, J=6.5 Hz).

By the same procedure as provided in above example, using the compound prepared in example 4 (more polar), compound of the present invention having the following physical data was obtained.

More Polar

TLC: Rf 0.52 (methanol:chloroform=1:9);

NMR (CDCl$_3$): δ5.90–5.60 (2H, m), 5.60–5.20 (4H, m), 4.07 (1H, q, J=8.5 Hz), 3.55 (1H, dd, J=10.0, 2.0 Hz), 3.04 (1H, brs), 2.74 (1H, ddd, J=18.0, 7.0, 1.0 Hz), 2.75–2.50 (1H, m), 2.50–1.20 (23H, m), 0.94 (3H, t, J=7.0 Hz).

Reference Example 16

(5Z,9α,11α,13E)-17,17-propano-11,16-bis(t-butyldimethylsilyloxy)-9-hydroxy-prosta-5,13-dienoic acid.methylester

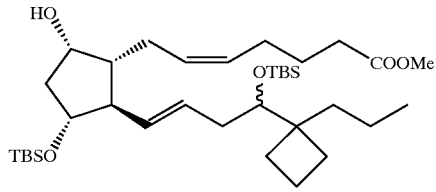

To a solution of (5Z,11α,13E)-17,17-propano-11,16-bis(t-butyldimethylsilyloxy)-9-oxoprosta-5,13-dienoic acid.methylester (740 mg, the compound prepared in reference example 3) in THF (20 ml) was added dropwise L-Selectride (1.76 ml; 1.0 M in THF solution) at −78° C. under an atmosphere of argon. After the mixture was stirred at same temperature for 30 min, to the solution was added dropwise a 30% aqueous solution of hydroperoxide (1 ml) at same temperature. The reaction mixture was warmed up to 0° C. The reaction mixture was quenched by addition of 2N aqueous solution of hydrochloric acid (1 ml), extracted with ethyl acetate. The extract was washed with water and a saturated aqueous solution of sodium chloride, successively, dried over anhydrous magnesium sulfate and concentrated. The residue was purified by column chromatography on silica gel (Merck Kiesel gel 7734, 30 g, hexane:ethyl acetate=9:1) to give the title compound (558 mg) as a pale yellow oil having the following physical data.

TLC: Rf 0.35 (hexane:ethyl acetate=9:1);

NMR (CDCl$_3$): δ5.60–5.10 (4H, m), 4.15–3.90 (2H, m), 3.66 (3H, s), 3.55 (1H, t, J=5 Hz), 2.70–2.50 (1H, m), 2.40–1.20 (24H, m), 1.00–0.80 (21H, m), 0.10–0.00 (12H, m).

Reference Example 17

(5Z,9α,11α,13E)-17,17-propano-11,16-bis(t-butyldimethylsilyloxy)-9-acetyloxy-prosta-5,13-dienoic acid.methylester

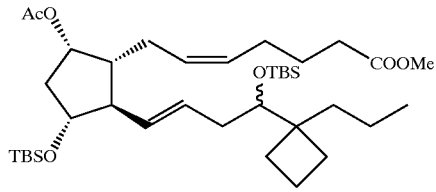

To a solution of the compound prepared in reference example 16 (518 mg) in pyridine (1 ml) was added acetic anhydride (0.15 ml) and dimethylaminopyridine (catalytic amount). The reaction mixture was stirred at room temperature overnight. The reaction mixture was quenched by addition of water, extracted with ethyl acetate. The extract was washed with dilute hydrochloric acid, water and a saturated aqueous solution of sodium chloride, successively, dried, filtered, and concentrated to give the title compound having the following physical data.

TLC: Rf 0.42 (hexane:ethyl acetate=9:1).

Reference Example 18

(5Z,9α,11α,13E)-17,17-propano-11,16-dihydroxy-9-acetyloxy-prosta-5,13-dienoic acid.methylester

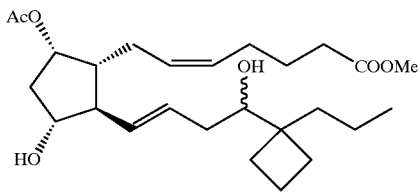

To a solution of the compound prepared in reference example 17 in acetonitrile (10 ml) was added dropwise 48% aqueous solution of hydrofluoric acid (0.5 ml) under cooling with ice. The reaction mixture was stirred at room temperature for 1.5 hours. The reaction mixture was quenched by addition of a saturated aqueous solution of sodium hydrogencarbonate, extracted with ethyl acetate. The extract was washed with a saturated aqueous solution of sodium hydrogencarbonate and a saturated aqueous solution of sodium chloride, successively, dried over anhydrous magnesium sulfate and concentrated. The residue was purified by Lobar column chromatography (size B, hexane:ethyl acetate=2:3) to give the title two compounds (less polar; 142 mg, more polar; 148 mg) having the following physical data.

Less Polar

TLC: Rf 0.30 (hexane:ethyl acetate=1:1);

NMR (CDCl$_3$): δ5.66 (1H, ddd, J=15.0, 7.8, 6.0 Hz), 5.45–5.30 (3H, m), 5.15–5.05 (1H, m), 4.00–3.85 (1H, m), 3.67 (3H, s), 3.55 (1H, dd, J=10.0, 2.4 Hz), 2.58–2.40 (1H, m), 2.40–1.30 (23H, m), 2.31 (2H, t, J=7.4 Hz), 2.06 (3H, s), 0.94 (3H, t, J=7.2 Hz).

More Polar

TLC: Rf 0.23 (hexane:ethyl acetate=1:1);

NMR (CDCl$_3$): δ5.65 (1H, ddd, J=14.8, 8.0, 6.2 Hz), 5.43–5.25 (3H, m), 5.15–5.05 (1H, m), 3.95–3.82 (1H, m), 3.67 (3H, s), 3.55 (1H, dd, J=10.0, 2.4 Hz), 2.60–2.40 (1H, m), 2.40–1.20 (23H, m), 2.30 (2H, t, J=7.4 Hz), 2.06 (3H, s), 0.94 (3H, t, J=6.7 Hz).

Reference Example 19

(5Z,9α,11α,13E)-17,17-propano-11,16-bis(2-tetrahydropyranyloxy)-9-acetyloxy-prosta-5,13-dienoic acid.methylester

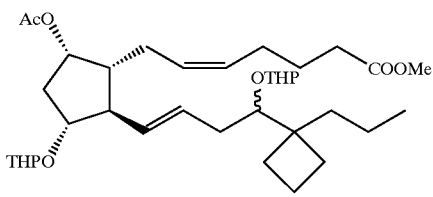

To a stirred solution of the compound prepared in reference example 18 (less polar; 64 mg) in dichloromethane (1 ml) was added dihydropyran (400 ml) and PPTS (pyridinium p-toluenesulfonate; 4 mg) at room temperature under an atmosphere of argon. The reaction mixture was stirred at room temperature for 6 hours. The reaction mixture was quenched by addition of water and a saturated aqueous solution of sodium hydrogencarbonate, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Fuji Silysia BW-300 20 ml, ethyl acetate:hexane= 1:7→1:5) to give the title compound (77.5 mg) as a colorless oil having the following physical data.

TLC: Rf 0.37 (ethyl acetate:hexane=1:4);

NMR (CDCl$_3$): δ5.85–5.45 (1H, m), 5.45–5.20 (3H, m), 5.10–4.98 (1H, m), 4.75–4.55 (2H, m), 4.05–3.70 (3H, m), 3.67 (3H, s), 3.65–3.38 (3H, m), 2.0–1.20 (36H, m), 2.04 (3H, s), 1.00–0.85 (3H, m).

Reference Example 20

(5Z,9α,11α,13E)-17,17-propano-11,16-bis(2-tetrahydropyranyloxy)-9-hydroxy-prosta-5,13-dienoic acid.methylester

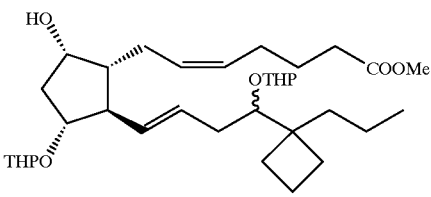

To a stirred solution of the compound prepared in reference example 19 (77 mg) in methanol (2 ml) was added potassium carbonate (15 mg) at room temperature under an atmosphere of argon. The reaction mixture was stirred at room temperature for 1 day. The reaction mixture was quenched by addition of water and 1N aqueous solution of hydrochloric acid, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Merck 7734, 20 ml, ethyl acetate:hexane=1:4→1:3) to give the title compound (70 mg) as a colorless oil having the following physical data.

TLC: Rf 0.39 (ethyl acetate:hexane=1:2);

NMR (CDCl$_3$): δ5.75 (4H, m), 4.75–4.55 (2H, m), 4.20–3.75 (4H, m), 3.67 (3H, s), 3.62–3.38 (3H, m), 2.60–1.20 (34H, m), 2.32 (2H, t, J=7.5 Hz), 0.93 (3H, t, J=7.5 Hz).

Reference Example 21

(5Z,9β,11α,13E)-17,17-propano-11,16-bis(2-tetrahydropyranyloxy)-9-fluoro-prosta-5,13-dienoic acid.methylester

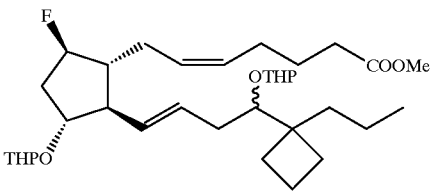

To a stirred solution of the compound prepared in reference example 20 (70 mg) in dichloromethane (2 ml) was added DAST (20 ml, diethylaminosulfurtrifluoride) at −78° C. under an atmosphere of argon. The reaction mixture was stirred for 20 min. The reaction mixture was quenched by addition of water and a saturated aqueous solution of sodium hydrogencarbonate, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Fuji Silysia BW-300 20 ml, ethyl acetate:hexane=1:10) to give the title compound (36 mg) as a colorless oil having the following physical data.

TLC: Rf 0.46 (ethyl acetate:hexane=1:5);

NMR (CDCl$_3$): δ5.90–5.20 (4H, m), 4.75–4.55 (2H, m), 4.40–3.75 (3H, m), 3.67 (3H, s), 3.67–3.40 (3H, m), 2.60–1.20 (35H, m), 2.32 (2H, t, J=7.5 Hz), 0.93 (3H, t, J=6.5 Hz).

Example 14

(5Z,9β,11α,13E)-17,17-propano-11,16-dihydroxy-9-fluoro-prosta-5,13-dienoic acid.methylester

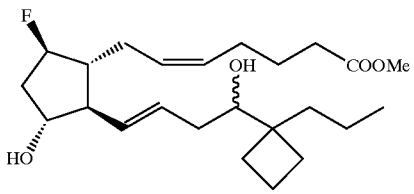

To a stirred mixture of the compound prepared in reference example 21 (36 mg) in THF (1 ml) and water (0.5 ml) was added acetic acid (2 ml) at room temperature. The reaction mixture was stirred at 45° C. The reaction mixture was quenched by addition of water, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Merck 7734, 20 ml, ethyl acetate:hexane= 1:2→1:1) and (Merck Lobar prepackaged column size A, ethyl acetate:hexane=2:1) to give the present invention compound (12 mg) having the following physical data.
Less Polar TLC: Rf 0.54 (ethyl acetate:hexane=1:1);

NMR (CDCl$_3$): δ5.80–5.40 (4H, m), 4.95–4.55 (1H, m), 4.20–4.00 (1H, m), 3.67 (3H, s), 3.54 (1H, dd, J=10.0, 2.5 Hz), 2.40–1.20 (24H, m), 2.33 (2H, t, J=7.5 Hz), 0.94 (3H, t, J=7.0 Hz).

By the same procedure as provided in reference example 19, 20 21 and example 14, using the compound prepared in reference example 18 (more polar), compound of the present invention having the following physical data was obtained.
More Polar TLC: Rf 0.48 (ethyl acetate:hexane=1:1);

NMR (CDCl$_3$): δ5.80–5.30 (4H, m), 4.95–4.55 (1H, m), 4.20–4.00 (1H, m), 3.67 (3H, s), 3.53 (1H, dd, J=10.0, 2.0 Hz), 3.00–1.20 (24H, m), 2.32 (2H, t, J=7.5 Hz), 0.94 (3H, t, J=6.5 Hz).

Example 15

(5Z,9β,11α,13E)-17,17-propano-11,16-dihydroxy-9-fluoro-prosta-5,13-dienoic acid

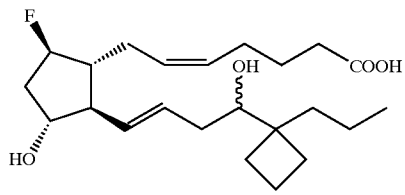

To a stirred solution of the compound prepared in example 14 (10 mg) in methanol (1 ml) was added 2N aqueous solution of sodium hydroxide (0.3 ml) at room temperature under an atmosphere of argon. The reaction mixture was stirred for 2 hours. The reaction mixture was quenched by addition of water and 1N aqueous solution of hydrochloric acid, extracted with ethyl acetate (×3). The extract was washed with water (×2) and a saturated aqueous solution of sodium chloride, successively, dried over anhydrous magnesium sulfate and concentrated to give the present invention compound (10 mg) as a colorless oil having the following physical data.
Less Polar TLC: Rf 0.38 (ethyl acetate:hexane=3:1);

NMR (CDCl$_3$): δ5.80–5.30 (4H, m), 5.00–4.60 (1H, m), 4.20–4.00 (1H, m), 3.62 (1H, dd, J=10.0, 2.0 Hz), 2.34 (2H, t, J=6.5 Hz), 2.40–1.20 (24H, m), 0.94 (3H, t, J=6.5 Hz).

By the same procedure as provided in example 15, using the compound prepared in example 14 (more polar), compound of the present invention having the following physical data was obtained.
More Polar TLC: Rf 0.35 (ethyl acetate:hexane=3:1);

NMR (CDCl$_3$): δ5.80–5.30 (4H, m), 5.00–4.80 (1H, m), 4.20–4.00 (1H, m), 3.59 (1H, d, J=10.5 Hz), 2.35 (2H, t, J=7.0 Hz), 2.40–1.20 (24H, m), 0.94 (3H, t, J=6.5 Hz).

Reference Example 22

(5Z,9α,11α,13E)-17,17-propano-11,16-bis(t-butyldimethylsilyloxy)-9-acetyloxy-20-norprosta-5,13-dienoic acid.methylester

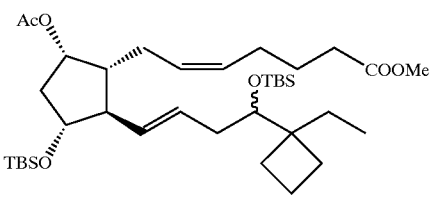

To a stirred solution of (5Z,9α,11α,13E)-17,17-propano-11,16-dihydroxy-9-acetyloxy-20-norprosta-5,13-dienoic acid.methylester (119 mg; more polar; the compound prepared in same method by reference example 18) in dichloromethane (2 ml) was added 2,6-lutidine (0.26 ml) and trifluoromethanesulfonic acid t-butyldimethylsilylester (0.26 ml) at 0° C. under an atmosphere of argon. The reaction mixture was stirred at 0° C. for 3 hours. The reaction mixture was quenched by addition of water, extracted with ethyl acetate (×3). The extract was washed with 0.1 N aqueous solution of hydrochloric acid (×2), water and a saturated aqueous solution of sodium chloride, successively, dried over anhydrous magnesium sulfate and concentrated to give the tittle compound (211 mg) as a colorless oil having the following physical data.

TLC: Rf 0.45 (ethyl acetate:hexane=1:8);

NMR (CDCl₃): δ5.70–5.45 (1H, m), 5.32 (1H, t, J=4.5 Hz), 5.25–5.05 (1H, m), 5.05–4.95 (1H, m), 3.90–3.70 (1H, m), 3.6 (3H, s), 358 (1H, t, J=5.0 Hz), 2.50–1.35 (21H, m), 2.29 (2H, t, J=7.5 Hz), 2.04 (3H, s), 1.00–0.80 (3H, m), 0.91 (9H, s), 0.86 (9H, s), 0.06 (3H, s), 0.05 (3H, s), 0.01 (6H, s)

Reference Example 23

(5Z,9α,11α,13E)-17,17-propano-11,16-bis(t-butyldimethylsilyloxy)-9-hydroxy-20-norprosta-5,13-dienoic acid.methylester

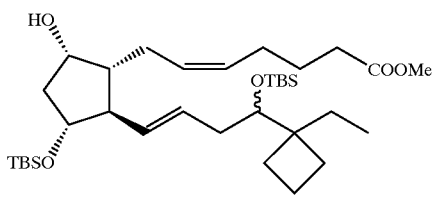

To a stirred solution of the compound prepared in reference example 22 (211 mg) in methanol (3 ml) was added potassium carbonate (60 mg) under an atmosphere of argon. The reaction mixture was stirred at room temperature for 1 day. The reaction mixture was quenched by addition of water and 1N aqueous solution of hydrochloric acid, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Merck 7734, 20 ml, ethyl acetate:hexane=1:8) to give the title compound (161 mg) as a colorless oil having the following physical data.

TLC: Rf 0.35 (ethyl acetate:hexane=1:8);

NMR (CDCl₃): δ5.60–5.15 (4H, m), 4.20–4.00 (1H, m), 4.00–3.95 (1H, m), 3.66 (3H, s), 3.57 (1H, t, J=5.0 Hz), 2.61 (1H, d, J=9.0 Hz), 2.42–1.35 (20H, m), 2.31 (2H, t, J=7.5 Hz), 1.00–0.80 (3H, m), 0.90 (9H, s), 0.87 (9H, s), 0.07 (3H, s), 0.05 (3H, s), 0.04 (6H, s).

Reference Example 24

(5Z,9α,11α,13E)-17,17-propano-11,16-bis(t-butyldimethylsilyloxy)-9-tosyloxy-20-norprosta-5,13-dienoic acid.methylester

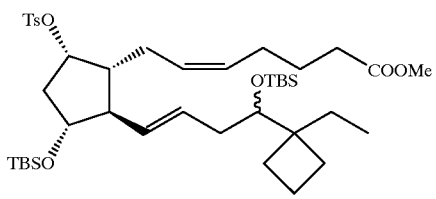

To a stirred solution of the compound prepared in reference example 23 (161 mg) in pyridine (1 ml) was added tosyl chloride (102 mg) at 0° C. under an atmosphere of argon. The reaction mixture, was stirred at room temperature for 9 hours. the reaction mixture was quenched by addition of water, extracted with ethyl acetate (×3). The extract was washed with a saturated aqueous solution of sodium hydrogencarbonate (×2), water and a saturated aqueous solution of sodium chloride, successively, dried over anhydrous magnesium sulfate and concentrated to give the title compound (194 mg) having the following physical data.

TLC: Rf 0.64 (ethyl acetate:hexane=1:19).

Reference Example 25

(5Z,9β,11α,13E)-17,17-propano-11,16-bis(t-butyldimethylsilyloxy)-9-chloro-20-norprosta-5,13-dienoic acid.methylester

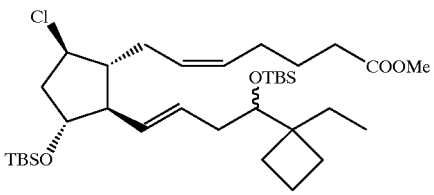

To a stirred solution of tetrabutylammonium chloride (742 mg) was added dropwise a solution of the compound prepared in reference example 24 (194 mg) in toluene (4 ml) under an atmosphere of argon. The reaction mixture was stirred at 40° C. for 12 hours. The reaction solution was changed to white suspension. The reaction mixture was quenched by addition of water, extracted with ethyl acetate (×3). The extract was washed with water (×2), a saturated aqueous solution of sodium hydrogencarbonate (×2) and a saturated aqueous solution of sodium chloride, successively, dried over anhydrous magnesium sulfate and concentrated to give the title compound (95 mg) having the following physical data.

TLC: Rf 0.67 (ethyl acetate:hexane=1:8).

Example 16

(5Z,9β,11α,13E)-17,17-propano-11,16-dihydroxy-9-chloro-20-norprosta-5,13-dienoic acid.methylester

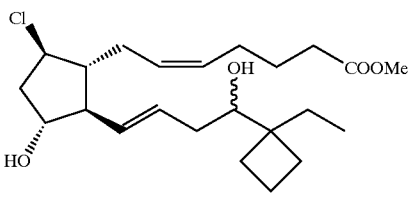

By the same procedure as provided in example 14, using the compound prepared in reference example 25, compound of the present invention having the following physical data was obtained.

More Polar

TLC: Rf 0.49 (ethyl acetate:hexane=1:1);

NMR (CDCl₃): δ5.60 (1H, ddd, J=15, 8, 6 Hz), 5.50–5.33 (3H, m), 4.20–3.95 (2H, m), 3.67 (3H, s), 3.53 (1H, dd, J=10.5, 2.5 Hz), 2.32 (2H, t, J=7.0 Hz), 2.40–1.50 (21H, m), 1.45 (1H, sept, J=7.0 Hz), 0.91 (3H, t, J=7.5 Hz).

Example 16(1)~16(6)

By the same procedure as provided in example 16, using the compound prepared in reference example 22, 23, 24, 25 or example 16, compounds of the present invention having the following physical data were obtained.

Example 16(1)

(5Z,9β,11α13E)-17,17-propano-11,16-dihydroxy-9-chloroprosta-5,13,19-trienoic acid.methylester

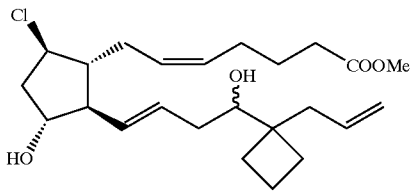

More Polar

TLC: Rf 0.49 (ethyl acetate:hexane=1:1);
NMR (CDCl$_3$): δ6.06–5.83 (1H, m), 5.67–5.23 (4H, m), 5.20–5.04 (2H, m), 4.20–3.95 (2H, m), 3.67 (3H, s), 3.53 (1H, dd, J=10.0, 2.5 Hz), 2.60–1.50 (22H, m), 2.32 (2H, t, J=8.0 Hz).

Example 16(2)

(5Z,9β,11α,13E)-17,17-propano-19,20-methano-11,16-dihydroxy-9-chloroprosta-5,13-dienoic acid.methylester

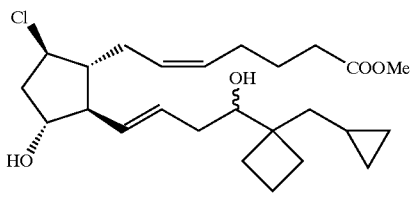

More Polar

TLC: Rf 0.25 (hexane:ethyl acetate=2:1);
NMR (CDCl$_3$): δ5.61 (1H, ddd, J=15.4, 7.8, 5.4 Hz), 5.52–5.35 (3H, m), 4.18–3.94 (2H, m), 3.67 (3H, s), 3.67 (1H, dd, J=10.0, 2.2 Hz), 2.40–1.60 (20H, m), 2.33 (2H, t, J=7.4 Hz), 1.52 (1H, dd, J=14.4, 6.6 Hz), 1.35 (1H, dd, J=14.4, 6.2 Hz), 0.90–0.68 (1H, m), 0.55–0.45 (2H, m), 0.15–0.05 (2H, m).

Example 16(3)

(5Z,9β,11α,13E)-17,17-propano-11,16-dihydroxy-9-chloro-19-methylprosta-5,13-dienoic acid.methylester

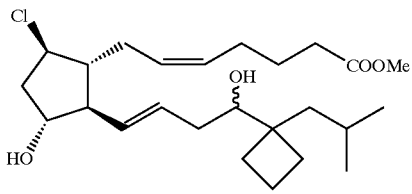

More Polar

TLC: Rf 0.32 (hexane:ethyl acetate=2:1);
NMR (CDCl$_3$): δ5.62 (1H, ddd, J=15.4, 7.8, 5.4 Hz), 5.52–5.35 (3H, m), 4.18–3.94 (2H, m), 3.67 (3H, s), 3.61 (1H, dd, J=10.4, 2.2 Hz), 2.40–1.60 (21H, m), 2.33 (2H, t, J=7.4 Hz), 1.55 (1H, dd, J=14.2, 6.6 Hz), 1.33 (1H, dd, J=14.2, 6.6 Hz), 0.918 (3H, d, J=6.6 Hz), 0.915 (3H, d, J=6.6 Hz).

Example 16(4)

(5Z,9β,11α,13E)-17,17-propano-11,16-dihydroxy-9-chloroprosta-5,13-dienoic acid.methylester

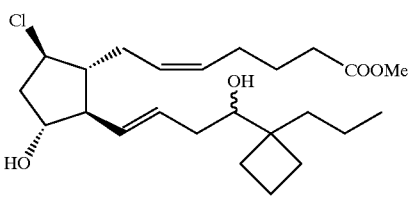

Less Polar

TLC: Rf 0.29 (hexane:ethyl acetate=2:1);
NMR (CDCl$_3$): δ5.61 (1H, ddd, J=15.4, 7.6, 5.8 Hz), 5.55–5.35 (3H, m), 4.20–3.95 (2H, m), 3.68 (3H, s), 3.53 (1H, dd, J=9.8, 2.2 Hz), 2.40–1.20 (24H, m), 2.33 (2H, t, J=7.6 Hz), 0.94 (3H, t, J=6.8 Hz).

More Polar

TLC: Rf 0.26 (hexane:ethyl acetate=2:1);
NMR (CDCl$_3$): δ5.58 (1H, ddd, J=15.0, 8.2, 5.6 Hz), 5.50–5.32 (3H, m), 4.18–3.95 (2H, m), 3.67 (3H, s), 3.53 (1H, dd, J=10.4, 2.2 Hz), 2.76 (1H, br), 2.40–1.20 (23H, m), 2.33 (2H, t, J=7.3 Hz), 0.94 (3H, t, J=6.8 Hz).

Example 16(5)

(5Z,9β,11α,13E)-17,17-propano-11,16-dihydroxy-9-chloro-19,20-dinorprosta-5,13-dienoic acid.methylester

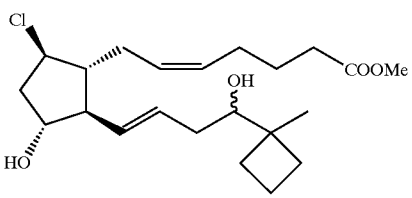

More Polar

TLC: Rf 0.30 (hexane:ethyl acetate=1:1);
NMR (CDCl$_3$): δ5.59 (1H, ddd, J=15, 8, 6 Hz), 5.47–5.30 (3H, m), 4.18–3.95 (2H, m), 3.67 (3H, s), 3.53 (1H, dd, J=10, 2 Hz), 2.40–1.55 (22H, m), 1.14 (3H, s).

Example 16(6)

(5Z,9β,11α,13E)-17,17-propano-11,16-dihydroxy-9-chloro-18,19,20-trinorprosta-5,13-dienoic acid.methylester

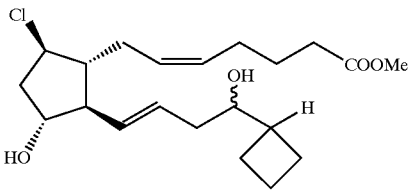

More Polar

TLC: Rf 0.26 (hexane:ethyl acetate=1:1);
NMR (CDCl$_3$): δ5.60 (1H, ddd, J=15, 8, 6 Hz), 5.49–5.31 (3H, m), 4.19–3.95 (2H, m), 3.67 (3H, s), 3.62–3.48 (1H, m), 2.60–1.60 (23H, m).

Example 17

(5Z,9β,11α,13E)-17,17-propano-11,16-dihydroxy-9-chloro-20-norprosta-5,13-dienoic acid

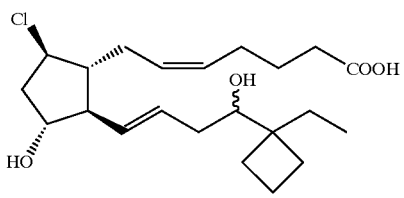

By the same procedure as provided in example 15, using the compound prepared in example 16, compound of the present invention having the following physical data was obtained.

More Polar

TLC: Rf 0.44 (ethyl acetate:hexane:acetic acid=6:3:0.1);
NMR (CDCl$_3$): δ5.80–5.35 (4H, m), 4.20–4.00 (2H, m), 3.59 (1H, dd, J=10.5, 2.5 Hz), 2.36 (2H, t, J=7.0 Hz), 2.40–1.60 (19H, m), 1.45 (1H, sept, J=7.5 Hz), 0.92 (3H, t, J=7.5 Hz).

Example 17(1)~17(6)

By the same procedure as provided in example 17, using the compound prepared in example 16(1)–16(6), compounds of the present invention having the following physical data were obtained.

Example 17(1)

(5Z,9β,11α,13E)-17,17-propano-11,16-dihydroxy-9-chloroprosta-5,13,19-trienoic acid

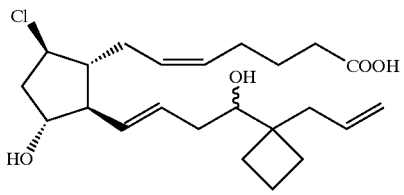

More Polar

TLC: Rf 0.44 (ethyl acetate:hexane:acetic acid=6:3:0.1);
NMR (CDCl$_3$): δ6.95 (1H, ddt, J=17.0, 10.0, 2.0 Hz), 5.70–5.32 (4H, m), 5.20–5.00 (2H, m), 4.20–4.00 (2H, m), 3.59 (1H, dd, J=10.0, 2.0 Hz), 2.36 (2H, t, J=7.0 Hz), 2.40–1.60 (20H, m).

Example 17(2)

(5Z,9β,11α,13E)-17,17-propano-19,20-methano-11,16-dihydroxy-9-chloroprosta-5,13-dienoic acid

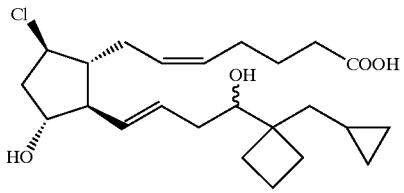

More Polar

TLC: Rf 0.31 (hexane:ethyl acetate:acetic acid=3:2:0.05);
NMR (CDCl$_3$): δ5.60 (1H, ddd, J=15.4, 7.6, 5.4 Hz), 5.55–5.35 (3H, m), 4.20–3.98 (2H, m), 4.20–3.00 (3H, br), 3.71 (1H, dd, J=10.4, 2.2 Hz), 2.40–1.60 (18H, m), 2.36 (2H, t, J=6.9 Hz), 1.51 (1H, dd, J=14.2, 6.8 Hz), 1.37 (1H, dd, J=14.2, 6.2 Hz), 0.90–0.65 (1H, m), 0.57–0.45 (2H, m), 0.15–0.05 (2H, m).

Example 17(3)

(5Z,9β,11α,13E)-17,17-propano-11,16-dihydroxy-9-chloro-19-methylprosta-5,13-dienoic acid

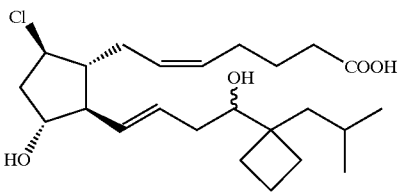

More Polar

TLC: Rf 0.34 (hexane:ethyl acetate:acetic acid=3:2:0.05);

NMR (CDCl$_3$): δ5.60 (1H, ddd, J=15.4, 8.2, 5.6 Hz), 5.55–5.35 (3H, m), 4.20–3.98 (2H, m), 4.20–3.00 (3H, br), 3.65 (1H, dd, J=10.2, 2.2 Hz), 2.40–1.65 (19H, m), 2.36 (2H, t, J=7.1 Hz), 1.55 (1H, dd, J=14.2, 6.6 Hz), 1.33 (1H, dd, J=14.2, 6.2 Hz), 0.92 (3H, d, J=6.6 Hz), 0.91 (3H, d, J=6.6 Hz).

Example 17(4)

(5Z,9β,11α,13E)-17,17-propano-11,16-dihydroxy-9-chloroprosta-5,13-dienoic acid

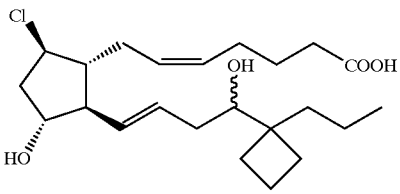

Less Polar

TLC: Rf 0.33 (hexane:ethyl acetate:acetic acid=3:2:0.05);

NMR (CDCl$_3$): δ5.60 (1H, ddd, J=15.4, 7.8, 5.6 Hz), 5.55–5.37 (3H, m), 4.20–4.00 (2H, m), 4.20–3.00 (3H, br), 3.60 (1H, dd, J=10.0, 2.2 Hz), 2.40–1.20 (22H, m), 2.35 (2H, t, J=6.9 Hz), 0.94 (3H, t, J=6.8 Hz).

More Polar

TLC: Rf 0.31 (hexane:ethyl acetate:acetic acid=3:2:0.05);

NMR (CDCl$_3$): δ5.58 (1H, ddd, J=15.4, 7.6, 5.4 Hz), 5.55–5.35 (3H, m), 4.20–4.00 (2H, m), 4.00–3.00 (3H, br), 3.57 (1H, dd, J=10.2, 2.2 Hz), 2.40–1.20 (22H, m), 2.36 (2H, t, J=6.9 Hz), 0.94 (3H, t, J=6.8 Hz).

Example 17(5)

(5Z,9β,11α,13E)-17,17-propano-11,16-dihydroxy-9-chloro-19,20-dinorprosta-5,13-dienoic acid

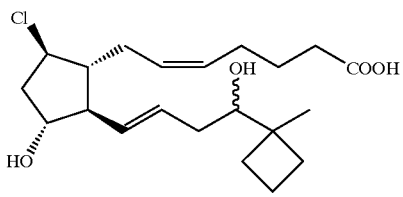

More Polar

TLC: Rf 0.32 (hexane:ethyl acetate:acetic acid=2:3:0.04);
NMR (CDCl$_3$): δ5.60 (1H, ddd, J=15, 8, 6 Hz), 5.55–5.35 (3H, m), 4.20–4.00 (2H, m), 4.00–3.00 (3H, br), 3.57 (1H, dd, J=10, 2 Hz), 2.40–1.50 (20H, m), 1.14 (3H, s).

Example 17(6)

(5Z,9β,11α,13E)-17,17-propano-11,16-dihydroxy-9-chloro-18,19,20-trinorprosta-5,13-dienoic acid

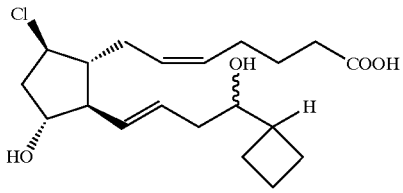

More Polar

TLC: Rf 0.25 (hexane:ethyl acetate:acetic acid=2:3:0.04);
NMR (CDCl$_3$): δ5.59 (1H, ddd, J=15, 8, 6 Hz), 5.54–5.33 (3H, m), 4.20–3.98 (2H, m), 4.00–3.00 (3H, br), 3.62–3.50 (1H, m), 2.60–1.55 (21H, m).

Reference Example 26

(5Z,9β,11α,13E)-17,17-propano-11,16-bis(t-butyldimethylsilyloxy)-9-formyloxy-prosta-5,13-dienoic acid.methylester

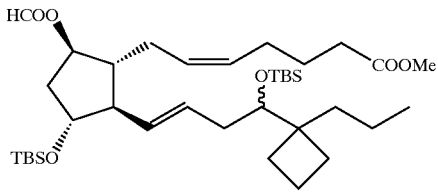

To a stirred solution of the compound prepared in reference example 16 (330 mg) in THF (1.5 ml) was added formic acid (25 ml) and triphenylphosphine (160 mg) under an atmosphere of argon. To the mixture was added dropwise DEAD (0.1 ml; diethylazodicarboxylate) at 0° C. The reaction mixture was stirred for 30 min. The reaction mixture was quenched by addition of water, extracted with ethyl acetate (×3). The extract was washed with water (×2) and a saturated aqueous solution of sodium chloride, successively, dried over anhydrous magnesium sulfate and concentrated. The residue was purified by column chromatography on silica gel (Merck 7734, 15 ml, ethyl acetate:hexane= 0:1→1:20) to give the title compound (20 mg) as a yellow oil having the following physical data.

TLC: Rf 0.56 (ethyl acetate:hexane=1:8);
NMR (CDCl$_3$): δ7.99 (1H, s), 5.65–5.17 (4H, m), 5.04–4.90 (1H, m), 3.94 (1H, q, J=7.5 Hz), 3.66 (3H, s), 3.56 (1H, t, J=5.5 Hz), 2.30 (2H, J=7.5 Hz), 2.40–1.20 (23H, m), 0.91 and 0.90 (9H, each-s), 0.86 (9H, s), 1.00–0.80 (3H, m), 0.06 (3H, s), 0.05 (3H, s), 0.01 (6H, s).

Reference Example 27

(5Z,9β,11α,13E)-17,17-propano-11,16-bis(t-butyldimethylsilyloxy)-9-hydroxy-prosta-5,13-dienoic acid.methylester

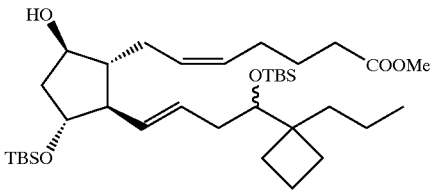

To a stirred solution of the compound prepared in reference example 26 (20 mg) in methanol (1 ml) was added ammonia in water solution (0.1 ml) at room temperature under an atmosphere of argon. The reaction mixture was stirred for 30 min. the reaction mixture was quenched by addition of a saturated aqueous solution of ammonium chloride, extracted with ethyl acetate. The extract was washed with water (×2) and a saturated aqueous solution of sodium chloride, successively, dried over anhydrous magnesium sulfate and concentrated. The residue was purified by column chromatography on silica gel (Merck 7734, 15 ml, ethyl acetate:hexane=1:8→1:4) to give the title compound (15 mg) as a colorless oil having the following physical data.

TLC: Rf 0.18 (ethyl acetate:hexane=1:8);
NMR (CDCl$_3$): δ5.62–5.18 (4H, m), 4.10–3.90 (2H, m), 3.67 (3H, s), 3.55 (1H, t, J=5.5 Hz), 2.32 (2H, t, J=8.0 Hz), 2.40–1.20 (23H, m), 1.00–0.80 (3H, m), 0.90 and 0.89 (9H, each-s), 0.86 (9H, s), 0.06 (3H, s), 0.04 (3H, s), 0.01 (6H, s).

Reference Example 28

(5Z,9β,11α,13E)-17,17-propano-11,16-bis(t-butyldimethylsilyloxy)-9-tosyloxy-prosta-5,13-dienoic acid.methylester

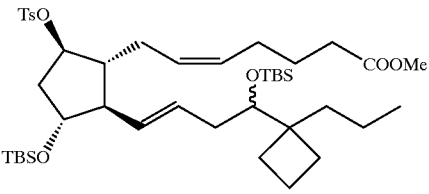

By the same procedure as provided in reference example 24, using the compound prepared in reference example 27, title compound having the following physical data was obtained.

TLC: Rf 0.47(ethyl acetate:hexane=6:1).

Reference Example 29

(5Z,9α,11α,13E)-17,17-propano-11,16-bis(t-butyldimethylsilyloxy)-9-chloro-prosta-5,13-dienoic acid.methylester

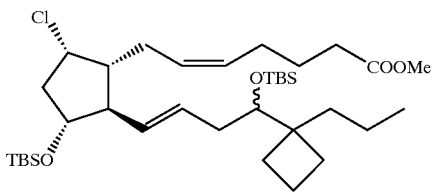

By the same procedure as provided in reference example 25, using the compound prepared in reference example 28, title compound having the following physical data was obtained.

TLC: Rf 0.45(ethyl acetate:hexane=1:20);

NMR (CDCl$_3$): δ5.72–5.10 (4H, m), 4.35–4.25 (1H, m), 3.95–3.75 (1H, m), 3.66 (3H, s), 3.57 (1H, t, J=5.5 Hz), 2.54 (2H, ddd, J=15.0, 9.0, 6.0 Hz), 2.50–1.20 (21H, m), 2.31 (2H, t, J=8.0 Hz), 1.00–0.80 (3H, m), 0.91 and 0.90 (9H, each s), 0.86 (9H, s), 0.10–0.00 (6H, m), 0.01 (6H, s).

Example 18

(5Z,9α,11α,13E)-17,17-propano-11,16-dihydroxy-9-chloro-prosta-5,13-dienoic acid.methylester

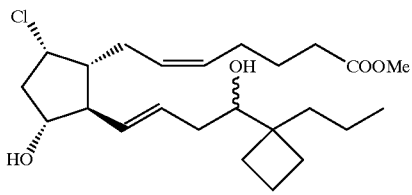

By the same procedure as provided in example 1, using the compound prepared in reference example 25, compound of the present invention having the following physical data was obtained.

Less Polar

TLC: Rf 0.56(ethyl acetate:hexane=1:1);

NMR (CDCl$_3$): δ5.66 (1H, ddd, J=15.5, 8.0, 6.0 Hz), 5.50–5.30 (3H, m), 4.38 (1H, t, J=5.0 Hz), 4.10–3.90 (1H, m), 3.67 (3H, s), 3.56 (1H, dd, J=10.0, 2.0 Hz), 2.70–1.20 (22H, m), 2.33 (2H, t, J=8.0 Hz), 0.94 (3H, t, J=7.0 Hz).

More Polar

TLC: Rf 0.47(ethyl acetate:hexane=1:1);

NMR (CDCl$_3$): δ5.66 (1H, ddd, J=15.5, 8.0, 5.5 Hz), 5.50–5.30 (3H, m), 4.38 (1H, t, J=5.0 Hz), 3.98 (1H, ddd, J=9.0, 6.0, 2.5 Hz), 3.67 (3H, s), 3.56 (1H dd, J=10.0, 2.0 Hz), 2.70–1.20 (22H, m), 2.32 (2H, t, J=7.5 Hz), 0.94 (3H, t, J=7.0 Hz).

Example 19

(5Z,9α,11α,13E)-17,17-propano-11,16-dihydroxy-9-chloro-prosta-5,13-dienoic acid

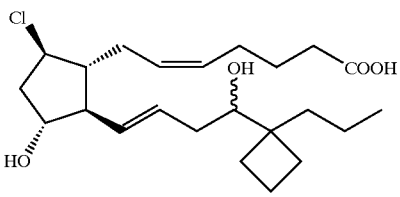

By the same procedure as provided in example 15, using the compound prepared in example 18, compound of the present invention having the following physical data was obtained.

Less Polar

TLC: Rf 0.47 (ethyl acetate:hexane=2:1);

NMR (CDCl$_3$): ≡5.75–5.30 (4H, m), 4.44 (1H, t, J=4.5 Hz), 3.97 (1H, ddd, J=9.0, 6.0, 3.5 Hz), 3.68 (1H, dd, J=10.0, 2.0 Hz), 2.70–1.20 (22H, m), 2.34 (2H, t, J=6.5 Hz), 0.94 (3H, t, J=6.5 Hz).

More Polar

TLC: Rf 0.47 (ethyl acetate:hexane=2:1);

NMR (CDCl$_3$): δ5.67 (1H, dt, J=15.5, 6.5 Hz), 5.60–5.30 (3H, m), 4.42 (1H, t, J=5.0 Hz), 4.03 (1H, ddd, J=9.0, 6.0, 3.0 Hz), 3.66 (1H, dd, J=9.5, 2.5 Hz) 2.70–1.20 (22H, m), 2.34 (2H, t, J=7.0 Hz), 0.94 (3H, t, J=6.5 Hz).

Reference Example 30

(5Z,8Z,11α,13E)-17,17-propano-11,16-bis(t-butyldimethylsilyloxy)-9-acetyloxy-prosta-5,8,13-trienoic acid.methylester

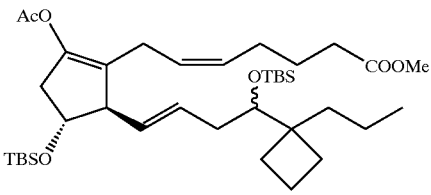

To a solution of (1E,4RS)-1-iodo-4-t-butyldimethylsilyloxy-5,5-propanoocta-1-ene (407 mg) in an hydrous ether (3 ml) was added dropwise t-butyllithium (1.21 ml; 1.7 M pentane solution) at −78° C. After the mixture was stirred for 60 min, to the mixture was added dropwise lithium 2-thienylcyanocuprate (4.8 ml; 0.25 M tetrahydrofuran solution) at same temperature. After the mixture was stirred for 20 min, to the mixture was added dropwise a solution of (5Z)-7-((3R)-3-t-butyldimethylsilyloxy-5-oxocyclopenta-1-ene (234 mg) in ether (4 ml). After the mixture was warmed up to −20° C. for 45 min, to the mixture was added acetic anhydride (1.88 ml). The reaction mixture was stirred at 0° C. for 30 min. The reaction mixture was quenched by addition of a saturated aqueous solution of ammonium chloride, extracted with hexane. The extract was washed with a saturated aqueous solution of sodium chloride, dried over anhydrous magnesium sulfate and concentrated. The residue was purified by column chromatography on silica gel (Wako gel C-200, 40 ml, hexane:ethyl acetate=1:0→50:1→20:1) to give the title compound (324 mg) having the following physical data.

TLC: Rf 0.50 (hexane:ethyl acetate=9:1);

NMR (CDCl$_3$): δ5.70–5.45 (1H, m), 5.45–5.15 (3H, m), 4.14–4.02 (1H, m), 3.66 (3H, s), 3.55 (1H, t, J=5.1 Hz), 3.05–2.92 (1H, m), 2.99–2.68 (2H, m), 2.60–2.30 (2H, m), 2.30 (2H, t, J=7.6 Hz), 2.20–1.20 (16H, m), 2.13 (3H, s), 1.00–0.90 (21H, m), 0.10–0.00 (12H, m).

Example 20

(5Z,8Z,11α,13E)-17,17-propano-11,16-dihydroxy-9-acetyloxy-prosta-5,8,13-trienoic acid.methylester

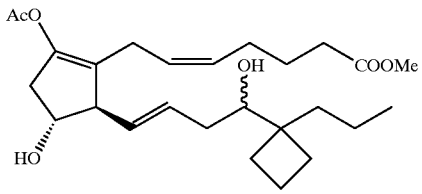

By the same procedure as provided in example 1, using the compound prepared in reference example 30, compounds of the present invention having the following physical data were obtained.

Less Polar

TLC: Rf 0.44 (hexane:ethyl acetate=1:1);

NMR (CDCl$_3$): δ5.63 (1H, ddd, J=15.4, 7.4, 6.0 Hz), 5.50–5.25 (3H, m), 4.18–4.02 (1H, m), 3.67 (3H, s), 3.52 (1H, dd, J=9.6, 2.4 Hz), 3.10–3.00 (1H, m), 3.00–2.72 (2H, m), 2.66–2.40 (2H, m), 2.40–1.20 (18H, m), 2.32 (2H, t, J=7.2 Hz), 2.16 (3H, s), 0.93 (3H, t, J=6.8 Hz).

More Polar

TLC: Rf 0.39 (hexane:ethyl acetate=1:1);

NMR (CDCl$_3$): δ5.62 (1H, ddd, J=15.4, 7.8, 6.2 Hz), 5.50–5.25 (3H, m), 4.18–4.02 (1H, m), 3.67 (3H, s), 3.52 (1H, dd, J=9.6, 2.2 Hz), 3.10–3.00 (1H, m), 2.98–2.72 (2H, m), 2.66–2.40 (2H, m), 2.40–1.20 (18H, m), 2.31 (2H, t, J=7.4 Hz), 2.16 (3H, s), 0.93 (3H, t, J=6.9 Hz).

Reference Example 31

(5Z,11α,13E)-17,17-propano-11,16-bis(t-butyldimethylsilyloxy)-1,9-dihydroxy-prosta-5,13-diene

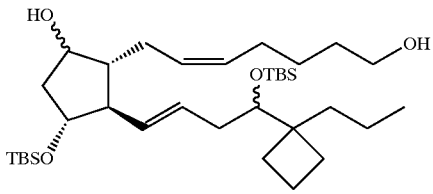

To a solution of the compound prepared in reference example 3 (174 mg) in THF (3 ml) was added dropwise DIBAL (1.16 ml; 0.95 M hexane solution) at −78° C. The reaction mixture was stirred at 0° C. for 30 min, and stirred at room temperature for 30 min. To the reaction mixture was added dropwise a saturated aqueous solution of sodium sulfate (0.3 ml), diluted with ether. The mixture was stirred at room temperature for 30 min. the reaction mixture was dried over anhydrous magnesium sulfate and concentrated to give the title compound (160 mg) having the following physical data.

TLC: Rf 0.40 (9α-OH form) and 0.24 (9β-OH form) (hexane:ethyl acetate=3:1).

Reference Example 32

(5Z,11α,13E)-17,17-propano-1,11,16-tris(t-butyldimethylsilyloxy)-9-hydroxy-prosta-5,13-diene

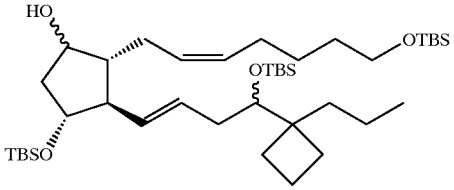

To a solution of the compound prepared in reference example 31 (160 mg) and pyridine (44 ml) in dichloromethane (3 ml) was added TBSCI (45 mg; t-butyidimethylsilyl chloride) under cooling with ice. The reaction mixture was stirred at room temperature for overnight. To the reaction mixture was added pyridine (50 ml) and TBSCI (50 mg). The reaction mixture was stirred at room temperature for 3 hours. The reaction mixture was quenched by addition of a saturated aqueous solution of sodium hydrogencarbonate, extracted with hexane. The extract was dried over anhydrous magnesium sulfate and concentrated. The residue was purified by column chromatography on silica gel (Merck 7734, 20 g, hexane:ethyl acetate=1:0→20:1→10:1) to give the title compound (total 142 mg) having the following physical data.

TLC: Rf 0.62 (9α-OH form) and 0.46 (9β-OH form) (hexane:ethyl acetate=9:1);

NMR (CDCl$_3$): δ5.60–5.15 (4H, m), 4.10–3.90 (2H, m), 3.65–3.45 (3H, m), 2.40–1.20 (24H, m), 1.00–0.90 (30H, m), 0.10–0.00 (18H, m).

Reference Example 33

(5Z,11α,13E)-17,17-propano-1,11,16-tris(t-butyidimethylsilyloxy)-9-oxoprosta-5,13-diene

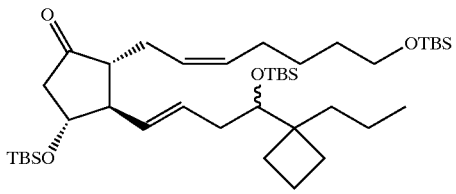

To a solution of oxalyl chloride (33 ml) in dichloromethane (0.5 ml) was added dropwise dimethylsulfoxide (55 ml) at −78° C. After the mixture was stirred for 10 min, to the mixture was added dropwise a solution of the compound prepared in reference example 32 (140 mg) in dichloromethane (3 ml). After the mixture was warmed up to −40° C. for 1 hour, to the mixture added dropwise triethylamine (0.22 ml). The reaction mixture was warmed up to −10° C. for 1 hour. The reaction mixture was quenched by addition of water and 2N aqueous solution of hydrochloric acid (0.7 ml), extracted with hexane. The extract was washed with a saturated aqueous solution of sodium chloride, dried over anhydrous magnesium sulfate and concentrated. The residue was purified by column chromatography on silica gel (Wako gel C-200, 15 g, hexane:ethyl acetate=1:0→30:1) to give the title compound (112 mg) having the following physical data.

TLC: Rf 0.80 (hexane:ethyl acetate=9:1);

NMR (CDCl$_3$): δ5.70–5.20 (4H, m), 4.05–3.90 (1H, m), 3.59 (2H, t, J=6.3 Hz), 3.58–3.50 (1H, m), 2.65–1.20 (24H, m), 1.00–0.90 (30H, m), 0.10–0.00 (18H, m).